(12) United States Patent
Carter et al.

(10) Patent No.: US 11,980,768 B2
(45) Date of Patent: May 14, 2024

(54) THERAPEUTIC SYSTEMS USING MAGNETIC AND ELECTRIC FIELDS

(71) Applicant: University of Iowa Research Foundation, Iowa City, IA (US)

(72) Inventors: Calvin S. Carter, Iowa City, IA (US); Sunny C. Huang, Iowa City, IA (US); Michael J. Miller, Iowa City, IA (US); Charles C. Searby, Iowa City, IA (US); Val C. Sheffield, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 171 days.

(21) Appl. No.: 17/369,784

(22) Filed: Jul. 7, 2021

(65) Prior Publication Data

US 2021/0339035 A1 Nov. 4, 2021

Related U.S. Application Data

(63) Continuation of application No. 16/280,551, filed on Feb. 20, 2019, now Pat. No. 11,071,875.
(Continued)

(51) Int. Cl.
*A61N 2/00* (2006.01)
*A61B 5/145* (2006.01)
(Continued)

(52) U.S. Cl.
CPC .......... *A61N 2/002* (2013.01); *A61B 5/14532* (2013.01); *A61N 1/0484* (2013.01);
(Continued)

(58) Field of Classification Search
CPC ................................................. A61N 2/00–12
See application file for complete search history.

(56) References Cited

U.S. PATENT DOCUMENTS 3,915,151 A 10/1975 Kraus
4,428,366 A 1/1984 Findl et al.
(Continued)

FOREIGN PATENT DOCUMENTS

AU 2019223992 B2 3/2022
EP 0279779 A1 * 2/1988
(Continued)

OTHER PUBLICATIONS

"U.S. Appl. No. 16/280,551, Non Final Office Action mailed Dec. 11, 2020", 16 pgs.
(Continued)

*Primary Examiner* — Thaddeus B Cox
(74) *Attorney, Agent, or Firm* — Schwegman Lundberg & Woessner, P.A.

(57) ABSTRACT

An example of subject may deliver a therapy by delivering energy to tissue. The system may comprise a magnetic field system and an electric field system. The magnetic field system may be configured to provide a magnetic field in a first direction to the tissue. The magnetic field system may include at least one magnetic field source to produce the magnetic field. The magnetic field produced by the at least one magnetic field source may include a magnetic field produced by at least one of a permanent magnet, a temporary magnet or electric current flow through a conductor. The electric field system may be configured to provide an electric field in a second direction to the tissue. The electric field system may include at least one electric field source to provide the electric field and the second direction is non-parallel to the first direction.

22 Claims, 30 Drawing Sheets

Related U.S. Application Data

(60) Provisional application No. 62/632,540, filed on Feb. 20, 2018.

(51) Int. Cl.
    *A61N 1/04*           (2006.01)
    *A61N 1/10*           (2006.01)
    *A61N 1/36*           (2006.01)
    *A61N 1/40*           (2006.01)
    *A61N 2/06*           (2006.01)

(52) U.S. Cl.
    CPC ........... *A61N 1/10* (2013.01); *A61N 1/36002* (2017.08); *A61N 1/36034* (2017.08); *A61N 1/40* (2013.01); *A61N 2/00* (2013.01); *A61N 2/06* (2013.01)

(56) References Cited

U.S. PATENT DOCUMENTS

| | | |
|---|---|---|
| 4,556,051 A | 12/1985 | Maurer |
| 4,838,850 A | 6/1989 | Rosengart |
| 4,850,959 A | 7/1989 | Findl |
| 5,267,152 A | 11/1993 | Yang et al. |
| 5,267,252 A | 11/1993 | Amano |
| 5,803,896 A | 9/1998 | Chen |
| 6,210,317 B1 | 4/2001 | Bonlie |
| 6,652,444 B1 | 11/2003 | Ross |
| 6,751,506 B2 | 6/2004 | Shealy |
| 6,856,839 B2 | 2/2005 | Litovitz |
| 8,700,161 B2 | 4/2014 | Harel et al. |
| 8,825,174 B2 | 9/2014 | Panting |
| 11,071,875 B2 | 7/2021 | Carter et al. |
| 2001/0044643 A1 | 11/2001 | Litovitz |
| 2002/0198567 A1 | 12/2002 | Keisari et al. |
| 2003/0055464 A1 | 3/2003 | Darvish et al. |
| 2004/0176805 A1 | 9/2004 | Whelan et al. |
| 2005/0267535 A1 | 12/2005 | Tofani |
| 2006/0167499 A1 | 7/2006 | Palti |
| 2008/0057556 A1 | 3/2008 | Miyakoshi et al. |
| 2008/0087288 A1 | 4/2008 | Wun |
| 2008/0125618 A1* | 5/2008 | Anderson ............... A61N 2/02 607/51 |
| 2009/0131993 A1 | 5/2009 | Rousso et al. |
| 2011/0230939 A1 | 9/2011 | Weinstock |
| 2012/0302821 A1 | 11/2012 | Burnett |
| 2013/0178910 A1 | 7/2013 | Azamian et al. |
| 2014/0296948 A1 | 10/2014 | Sluijter |
| 2018/0221656 A1 | 8/2018 | Garcia Perez et al. |
| 2019/0126036 A1* | 5/2019 | Franco-Obregon .... A61N 1/326 |
| 2019/0255344 A1 | 8/2019 | Carter et al. |
| 2022/0118269 A1 | 4/2022 | Carter et al. |

FOREIGN PATENT DOCUMENTS

| | | |
|---|---|---|
| WO | WO-02098501 A2 | 12/2002 |
| WO | WO-2008019710 A1 | 2/2008 |
| WO | WO-2009061142 A2 | 5/2009 |
| WO | WO-2009090440 A1 | 7/2009 |
| WO | WO-2010067180 A2 | 6/2010 |
| WO | WO-2012083259 A2 | 6/2012 |
| WO | WO-2014070287 A1 | 5/2014 |
| WO | WO-2015069446 A1 | 5/2015 |
| WO | WO-2019164903 A1 | 8/2019 |

OTHER PUBLICATIONS

"U.S. Appl. No. 16/280,551, Notice of Allowance mailed Mar. 24, 2021", 11 pgs.
"U.S. Appl. No. 16/280,551, Response filed Mar. 11, 2021 to Non Final Office Action mailed Dec. 11, 2020", 10 pgs.
"Australian Application Serial No. 2019223992, First Examination Report mailed Mar. 6, 2021", 6 pgs.
"Effect of Intensive Therapy on Residual B-Cell Function in Patients with Type 1 Diabetes in the Diabetes Control and Complications Trial—A Randomized, Controlled Trial", Annals of Internal Medicine, 128(7), (1998), 517-523.
"European Application Serial No. 19709259.6, Response filed Mar. 23, 2021 to Communication pursuant to Rules 161(2) and 162 EPC", 30 pgs.
"Far Infrared Radiation Treatment for Diabetes", [online], Retrieved from the Internet: <URL: https://clinicaltrials.gov/ct2/show/NCT00573456>, (Aug. 2009), 5 pgs.
"Guidance for Industry—Diabetes Mellitus: Developing Drugs and Therapeutic Biologics for Treatment and Prevention", U. S. Department of Health and Human Services, Food and Drug Administration, (Feb. 2008), 34 pgs.
"International Application Serial No. PCT/US2019/018716, International Preliminary Report on Patentability mailed Sep. 3, 2020", 9 pgs.
"International Application Serial No. PCT/US2019/018716, International Search Report mailed Jun. 6, 2019", 6 pgs.
"International Application Serial No. PCT/US2019/018716, Written Opinion mailed Jun. 6, 2019", 9 pgs.
Ahmad, Waqar, et al., "Oxidative toxicity in diabetes and Alzheimer's disease: mechanisms behind ROS/RNS generation", Journal of Biomedical Science, 24: 76, (2017), 1-10.
Alfaras, Irene, et al., "Health benefits of late-onset metformin treatment every other week in mice", npj Aging and Mechanisms of Disease, 3: 16, (2017), 1-13.
Barber, Sian, et al., "Oxidative stress in ALS: Key role in motor neuron injury and therapeutic target", Free Radical Biology & Medicine, 48, (2010), 629-641.
Birch-Machin, Mark A., et al., "An Evaluation of the Measurement of the Activities of Complexes I-IV in the Respiratory Chain of Human Skeletal Muscle Mitochondria", Biochemical Medicine and Metabolic Biology, 51, (1994), 35-42.
Blaser, Heiko, et al., "TNF and ROS Crosstalk in In?ammation", Trends in Cell Biology, 26(4), (Apr. 2016), 249-261.
Bouzid, Mohamed A., et al., "Radical Oxygen Species, Exercise and Aging: An Update", Sports Med, 45, (2015), 1245-1261.
Buckingham, Bruce, et al., "Effectiveness of Early Intensive Therapy on B-Cell Preservation in Tpe 1 Diabetes", Diabetes Care. published online Oct. 15, 2013, (2013), 1-6.
Caduff, A., et al., "First human experiments with a novel non-invasive, non-optical continuous glucose monitoring system", Biosensors & Bioelectronics, 19(3), (2003), 209-217.
Carter, Calvin S., et al., "Abnormal development of NG2+PDGFR-a+ neural progenitor cells leads to neonatal hydrocephalus in a ciliopathy mouse model", Nature Medicine, 18(12), (2012), 1797-1804 (9 pgs.).
Curry, Daniel W., et al., "Targeting AMPK Signaling as a Neuroprotective Strategy in Parkinson's Disease", Journal of Parkinson's Disease, 8, (2018), 161-181.
Devos, David, et al., "Targeting Chelatable Iron as a Therapeutic Modality in Parkinson's Disease", Antioxidants & Redox Signaling, 21(2), (2014), 195-210.
El-Kenawi, Asmaa, et al., "Inflammation, ROS, and Mutagenesis", Cancer Cell, 32, (2017), 727-729.
Finkel, Toren, "Signal transduction by reactive oxygen species", J. Cell Biol., 194(1), (2011), 7-15.
Fisher-Wellman, Kelsey H., et al., "Linking mitochondrial bioenergetics to insulin resistance via redox biology", Trends in Endocrinology and Metabolism, 23(3), (Mar. 2012), 142-153.
Foretz, Marc, et al., "Metformin inhibits hepatic gluconeogenesis in mice independently of the LKB1/AMPK pathway via a decrease in hepatic energy state", The Journal of Clinical Investigation, 120(7), (Jul. 2010), 2355-2369.
Furman, Brian L., et al., "Streptozotocin-Induced Diabetic Models in Mice and Rats", Curr. Protoc. Pharmacol., Suppl. 70, (Sep. 2015), 5.47.1-5.47.20.
Glasauer, Andrea, et al., "Targeting antioxidants for cancer therapy", Biochemical Pharmacology, 92, (2014), 90-101.
Havas, Magda, "Dirty Electricity Elevates Blood Sugar Among Electrically Sensitive Diabetics and May Explain Brittle Diabetes", Electromagnetic Biology and Medicine, 27, (2008), 135-146.

(56) References Cited

OTHER PUBLICATIONS

Hwang, Onyou, et al., "Role of Oxidative Stress in Parkinson's Disease", Experimental Neurobiology, 22(1), (2013), 11-17.
Jin, Huajun, et al., "Mitochondria-Targeted Antioxidants for Treatment of Parkinson's Disease: Preclinal and Clinical Outcomes", NIH Public Access, Author manuscript, published in final edited form as: Biochim Biophys Acta., 1842(8), (2014), 1282-1294, (2014), 33 pgs.
Keymeulen, B., et al., "Four-year metabolic outcome of a randomised controlled CD3-antibody trial in recent-onset type 1 diabetic patients depends on their age and baseline residual beta cell mass", Diabetologia, 53, (2010), 614-623.
King, Aileen J. F., et al., "The use of animal models in diabetes research", British Journal of Pharmacology, 166, (2012), 877-894.
Kirillov, I. B., et al., "[Magentotherapy in the comprehensive treatment of vascular complications of diabetes mellitus]", Klin Med (Mosk), 74(5), (1996), 39-41, (1996), 1 pg.
Kobayashi, Kunihisa, et al., "The db/db Mouse, a Model for Diabetic Dyslipidemia: Molecular Characterization and Effects of Western Diet Feeding", Metabolism, 49(1), (2000), 22-31.
Kumar, Anil, et al., "A review on mitochondrial restorative mechanism of antioxidants in Alzheimer's disease and other neurological condictions", Frontiers in Pharmacology, vol. 6, Article 206, (Sep. 2015), 1-13.
Lee, Sihoon, et al., "Comparison between surrogate indexes of insulin sensitivity and resistance and hyperinsulinemic euglycemic clamp estimates in mice", Am J Physiol Endocrinol Metab, 294, (2008), E261-E270.
Leloup, Corinne, et al., "Mitochondrial Reactive Oxygen Species Are Obligatory Signals for Glucose-Induced Insulin Secretion", Diabetes, vol. 58, (Mar. 2009), 673-681.
Liochev, Stefan I., et al., "Reactive oxygen species and the free radical theory of aging", Free Radical Biology and Medicine, 60, (2013), 1-4.
Livingstone, Shona J., et al., "Estimated Life Expectancy in a Scottish Cohort With Type 1 Diabetes, 2008-2010", JAMA, 313(1), (2015), 37-44.
Loh, Kim, et al., "Reactive Oxygen Species Enhances Insulin Sensitivity", Cell Metabolism, 10, (2009), 260-272.
Madiraju, Anila K., et al., "Metformin suppresses gluconeogenesis by inhibiting mitochondrial glycerophosphate dehydrogenase", Nature, 510, (2014), 542-546 (17 pgs.).
Mahadev, Kalyankar, et al., "The NAD(P)H Oxidase Homolog Nox4 Modulates Insulin-Stimulated Generation of H202 and Plays an Integral Role in Insulin Signal Transduction", Molecular and Cellular Biology, 24(5), (Mar. 2004), 1844-1854.
Markesbery, William R., "The Role of Oxidative Stess in Alzheimer's Disease", Arch Neurol, 56, (1999), 1449-1452.
Martin-Montalvo, Alejandro, et al., "Metformin improves healthspan and lifespan in mice", HHS Public Access, Author manuscript, published in final edited form as: Nat Commun., 4, (2013), 2192, (2013), 23 pgs.
Mittal, Manish, et al., "Reactive Oxygen Species in Inflammation and Tissue Injury", Antioxidants & Redox Signaling, 20(7), (2014), 1126-1167.
Mogavero, Angelo, et al., "Metformin transiently inhibits colorectal cancer cell proliferation as a result of either AMPK activation or increased ROS production", Scientific Reports, 7: 15992, (2017), 1-12.
Owen, Mark R., et al., "Evidence that metformin exerts its antidiabetic effects through inhibition of complex 1 of the mitochondrial respiratory chain", Biochem. J., 348, (2000), 607-614.
Poprac, Patrik, et al., "Targeting Free Radicals in Oxidative Stress-Related Human Diseases", Trends in Pharmacological Sciences, 38(7), (Jul. 2017), 592-607.
Puspita, Lesly, et al., "Oxidative stress and cellular pathologies in Parkinson's disease", Molecular Brain, 10: 53, (2017), 12 pgs.
Qinna, Nidal A., et al., "Impact of streptozotocin on altering normal glucose homeostasis during insulin testing in diabetic rats compared to normoglycemic rats", Drug Design, Development and Therapy, 9, (2015), 2515-2525.
Raza, Muhammad H., et al., "ROS-modulated therapeutic approaches in cancer treatment", J. Cancer Res Clin Oncol, 143, (2017), 1789-1809.
Sherifali, Diana, et al., "The Effect of Oral Antidiabetic Agents on Glycated Hemoglobin Levels: A Systematic Review and Meta-Analysis", Diabetes Care, (2010), 1-11.
Sieron, A., "Effect of Low Frequency Electromagnetic Fields on [3H]Glucose Uptake in Rat Tissues", Polish J. of Environ. Stud., 16(2), (2007), 309-312.
Simm, Andreas, et al., "Reactive oxygen species (ROS) and aging: Do we need them can we measure them should we block them?", Signal Transduction, 3, (2005), 115-125.
Song, Chang W., et al., "Metformin kills and radiosensitizes cancer cells and preferentially kills cancer stem cells", Scientific Reports, 2: 362, (2012), 1-9.
Steffes, Michael W,, et al., "B-Cell Function and the Development of Diabetes-Related Complications in the Diabetes Control and Complications Trial", Diabetes Care, 26(3), (Mar. 2003), 832-836.
Tonnies, Eric, et al., "Oxidative Stress, Synaptic Dysfunction, and Alzheimer's Disease", Journal of Alzheimer's Disease, 57, (2017), 1105-1121.
Valencia, Willy M., et al., "Metformin and ageing: improving ageing outcomes beyond glycaemic control", HHS Public Access, Author manuscript, published in final edited form as: Diabetologia, 60(9), (2017), 1630-1638, (2017), 16 pgs.
Vetere, Amedeo, et al., "Targeting the pancreatic ß-cell to treat diabetes", Nature Reviews Drug Discovery, 13, (Aoeil 2014), 278-289.
Wang, G, J., et al., "Low-dose radiation and its clinical implications: diabetes", Hum Exp Toxicol, 27(2), (2008), 135-142.
Wang, Huizhen, et al., "Magnetic Fields and Reactive Oxygen Species", Int. J. Mol. Sci., 18, 2175, (2017), 20 pgs.
Wang, Jian, "Mitochondria as a therapeutic target in Alzheimer's disease", Genes & Diseases, 3, (2016), 220-227.
Wheaton, William W., et al., "Metformin inhibits mitochondrial complex I of cancer cells to reduce tumorigenesis", eLife, 3:e02242, (2014), 18 pgs.
Yang, Xiangjun, et al., "Antioxidant Treatment Limits Neuroin? ammation in Experimental Glaucoma", IOVS, 57(4), (Apr. 2016), 2344-2354.
Zhang, Hui-Hui, et al., "Combinational strategies of metformin and chemotherapy in cancers", Cancer Chemother Pharmacol, 78, (2016), 13-26.
"Australian Application Serial No. 2019223992, Response filed Feb. 9, 2022 to First Examination Report mailed Mar. 6, 2021", 21 pgs.
"Australian Application Serial No. 2022204053, First Examination Report mailed Aug. 22, 2023", 6 pgs.
"European Application Serial No. 19709259.6, Communication Pursuant to Article 94(3) EPC mailed Aug. 8, 2023", 5 pgs.

\* cited by examiner

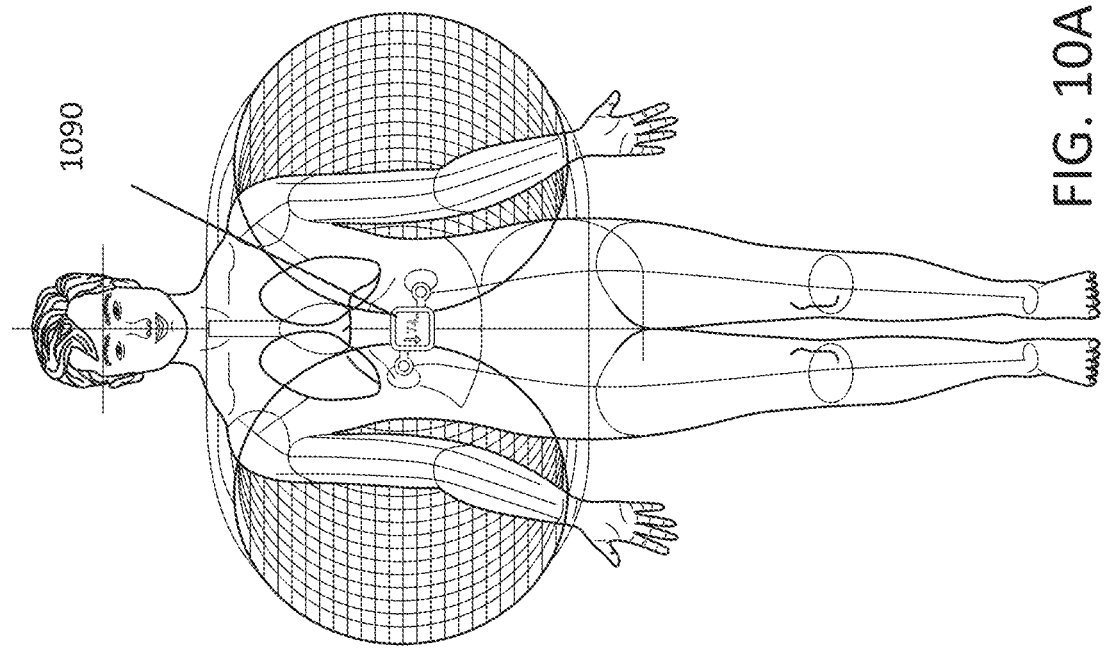
FIG. 10A
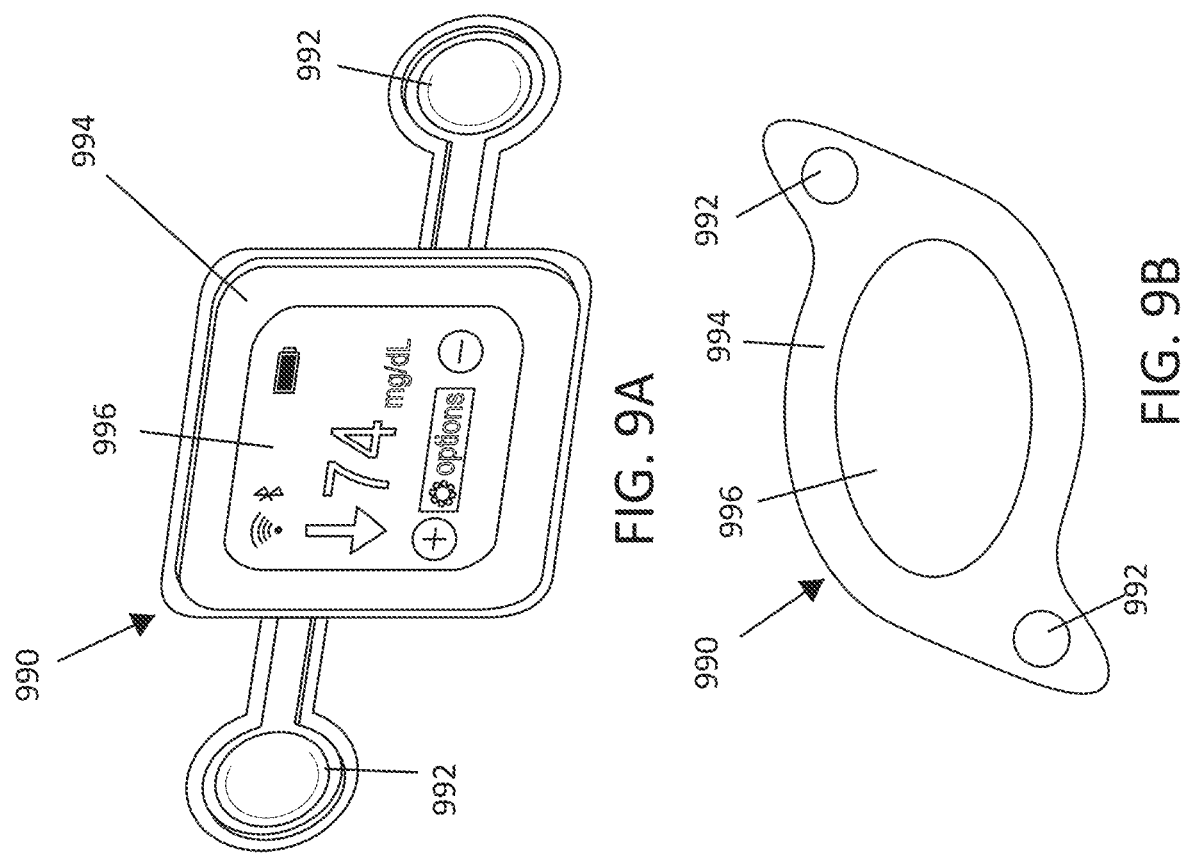
FIG. 9A
FIG. 9B

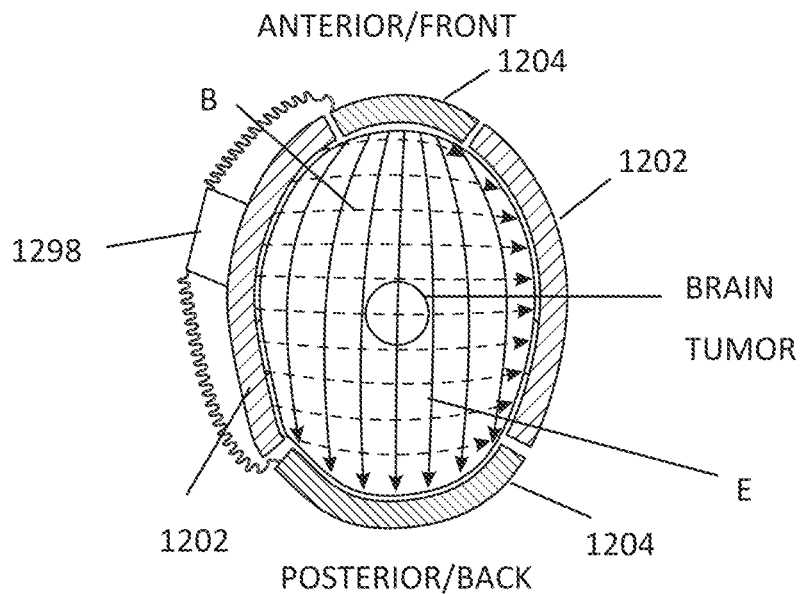
FIG. 12
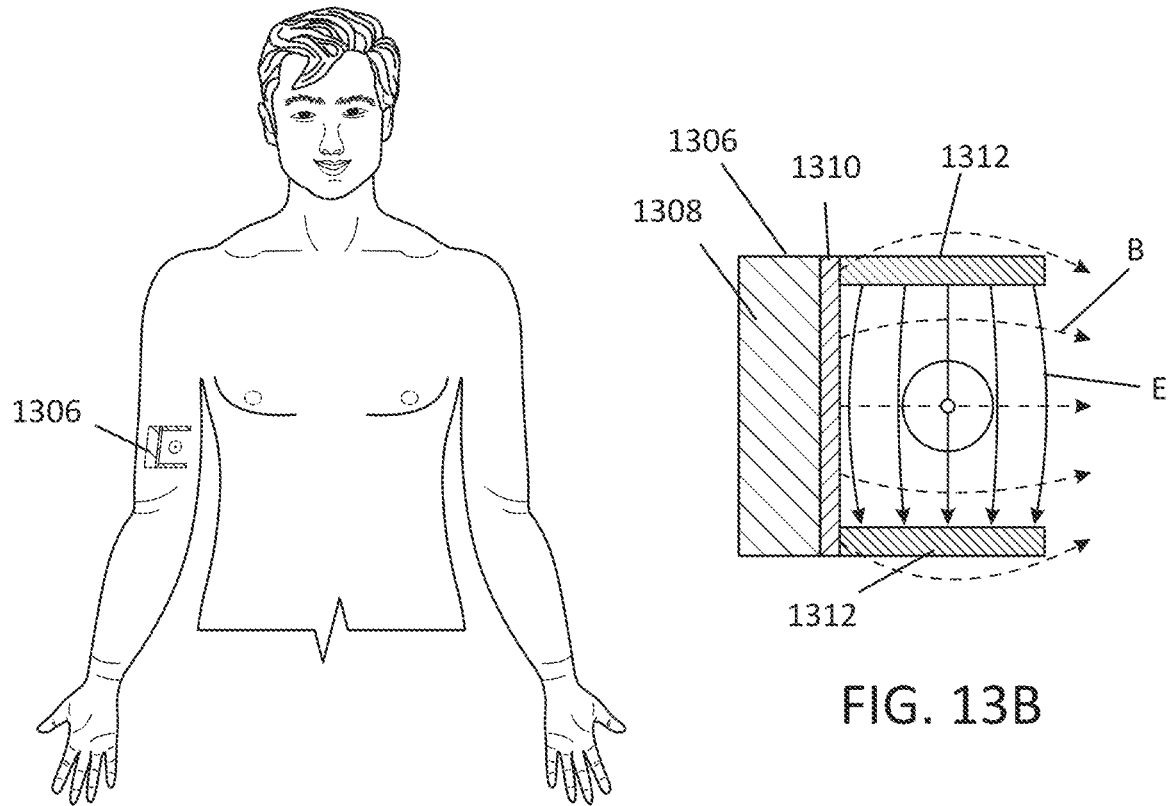
FIG. 13A
FIG. 13B

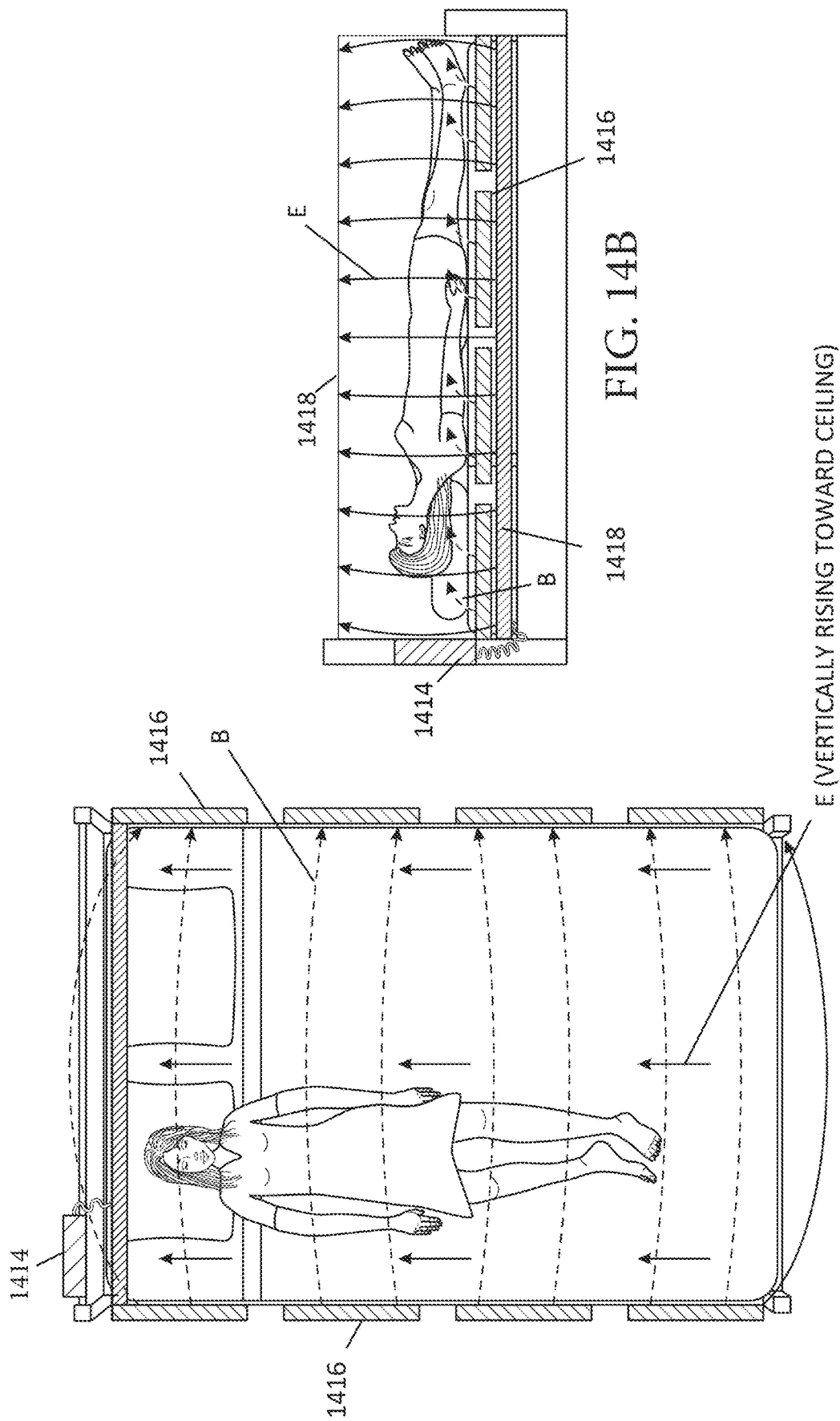

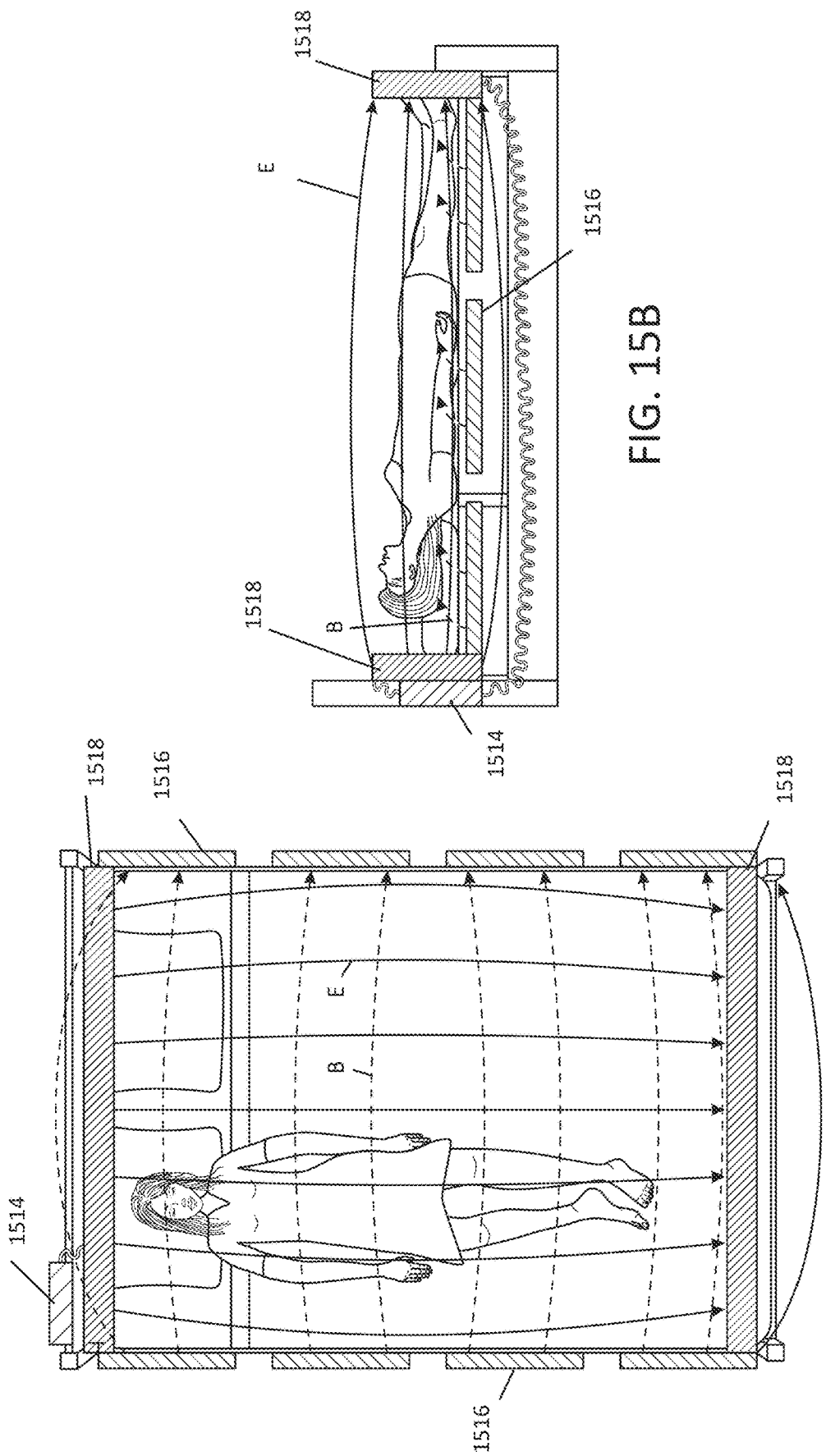

THERAPEUTIC SYSTEMS USING MAGNETIC AND ELECTRIC FIELDS

CLAIM OF PRIORITY

This application is a continuation of U.S. application Ser. No. 16/280,551, filed on Feb. 20, 2019, now U.S. Pat. No. 11,071,875, and titled "THERAPEUTIC SYSTEMS USING MAGNETIC AND ELECTRIC FIELDS," and claims the benefit of priority under 35 U.S.C. § 119(e) of U.S. Provisional Patent Application Ser. No. 62/632,540, filed on Feb. 20, 2018, and titled "TREATMENT OF DIABETES USING MAGNETIC AND NON-PARALLEL ELECTROSTATIC FIELDS," which applications are incorporated by reference herein in their entirety.

STATEMENT OF GOVERNMENT INTEREST

This invention was made with government support under 1RO1 NS083543 awarded by the National Institutes of Health. The government has certain rights in the invention.

TECHNICAL FIELD

The present disclosure relates generally to medical systems, and more particularly, to systems, devices, and methods for delivering therapy by delivering energy to tissue.

BACKGROUND

Existing therapies for chronic diseases, such as but not limited diabetes, cancer, neurological and immune diseases, have significant challenges. For example, existing therapies may only treat symptoms of the disease, may be invasive, and/or may have relatively low patient adherence.

By way of a non-limiting example, many diabetic patients have failed to achieve a healthy glycemic range and have a significantly greater risk of premature death in spite of the medications that are available to manage the disease. Patients may fail to adhere to their therapy because of the complexity of the dosing regimen for their prescribed medication, the discomfort of testing and insulin injections, and drug intolerability. Conventional diabetic care and the cost of treating complications resulting from poorly-managed diabetes is very costly.

What is needed is an improved therapy for treating chronic diseases that addresses some of these shortcomings of existing therapies.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example of subject matter (such as a system, a device, apparatus or machine) may deliver a therapy by delivering energy to tissue. The system may comprise a magnetic field system and an electric field system. The magnetic field system may be configured to provide a magnetic field in a first direction to the tissue. The magnetic field system may include at least one magnetic field source to produce the magnetic field. The magnetic field produced by the at least one magnetic field source may include a magnetic field produced by at least one of a permanent magnet, a temporary magnet or electric current flow through a conductor. The electric field system may be configured to provide an electric field in a second direction to the tissue. The electric field system may include at least one electric field source to provide the electric field and the second direction is non-parallel to the first direction. By way of example and not limitation, the therapy may include a therapy for diabetes, cancer, obesity, inflammation, or glaucoma. Other chronic diseases and conditions may be treated.

An example of subject matter (e.g. a method, a means for performing acts, or a machine-readable medium including instructions that, when performed by the machine, cause the machine to perform acts) may include delivering a therapy by delivering energy to tissue. Delivering energy to the tissue may include providing a magnetic field in a first direction to the tissue using a magnetic field system including a magnetic field source to produce the magnetic field. The magnetic field produced by the magnetic field source may include a magnetic field produced by at least one of a permanent magnet, a temporary magnet or electric current flow through a conductor. Delivering energy to the tissue may further include providing an electric field in a second direction to the tissue using an electric field system including an electric field source to produce the electric field, wherein the second direction is non-parallel to the first direction. Target tissues may include, but are not limited to, liver or pancreatic tissue, tumor(s), visceral muscle, white fat, brown fat, gall bladder, stomach, large and small intestines, kidney, heart, spleen, appendix, retina or optic nerve or brain.

An example of subject matter (e.g. a method, a means for performing acts, or a machine-readable medium including instructions that, when performed by the machine, cause the machine to perform acts) may prevent, inhibit or treat one or more symptoms of a disease associated with aberrant reactive oxygen species levels in a mammal. The subject matter may include applying to one or more organs or tissues of the mammal, a magnetic field in a first direction and an electric field in a second direction. The magnetic field may be provided by at least one magnetic field source that includes at least one permanent magnet, a temporary magnet or electric current flow through a conductor to produce the magnetic field. The electric field may be provided by at least one electric field source to provide the electric field and the second direction is non-parallel to the first direction. The electric and magnetic fields are effective to prevent, inhibit or treat the one or more symptoms of the disease in the mammal associated with aberrant reactive oxygen species levels.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9A-9B illustrate, by way of example and not limitation, embodiments of a system in the form of a patch-like device.

FIGS. 10A-10B illustrate the patch-like device of FIG. 9A implemented as a wearable device adhered or otherwise attached directly or indirectly to the patient and as an environmental device under the bed mattress, respectively.

FIG. 12 illustrates an embodiment of a wearable MNPEF system as an article to be worn on the head.

FIGS. 13A-B illustrate an embodiment of an implantable MNPEF system, illustrated by way of example and not limitation, around a tumor in an arm.

FIGS. 14A-B illustrate an embodiment of an environmental MNPEF system, illustrated by way of example and not limitation, around a patient's bed.

FIGS. 15A-B illustrate an embodiment of an environmental MNPEF system, illustrated by way of example and not limitation, around a patient's bed.

DETAILED DESCRIPTION

Figure 1:
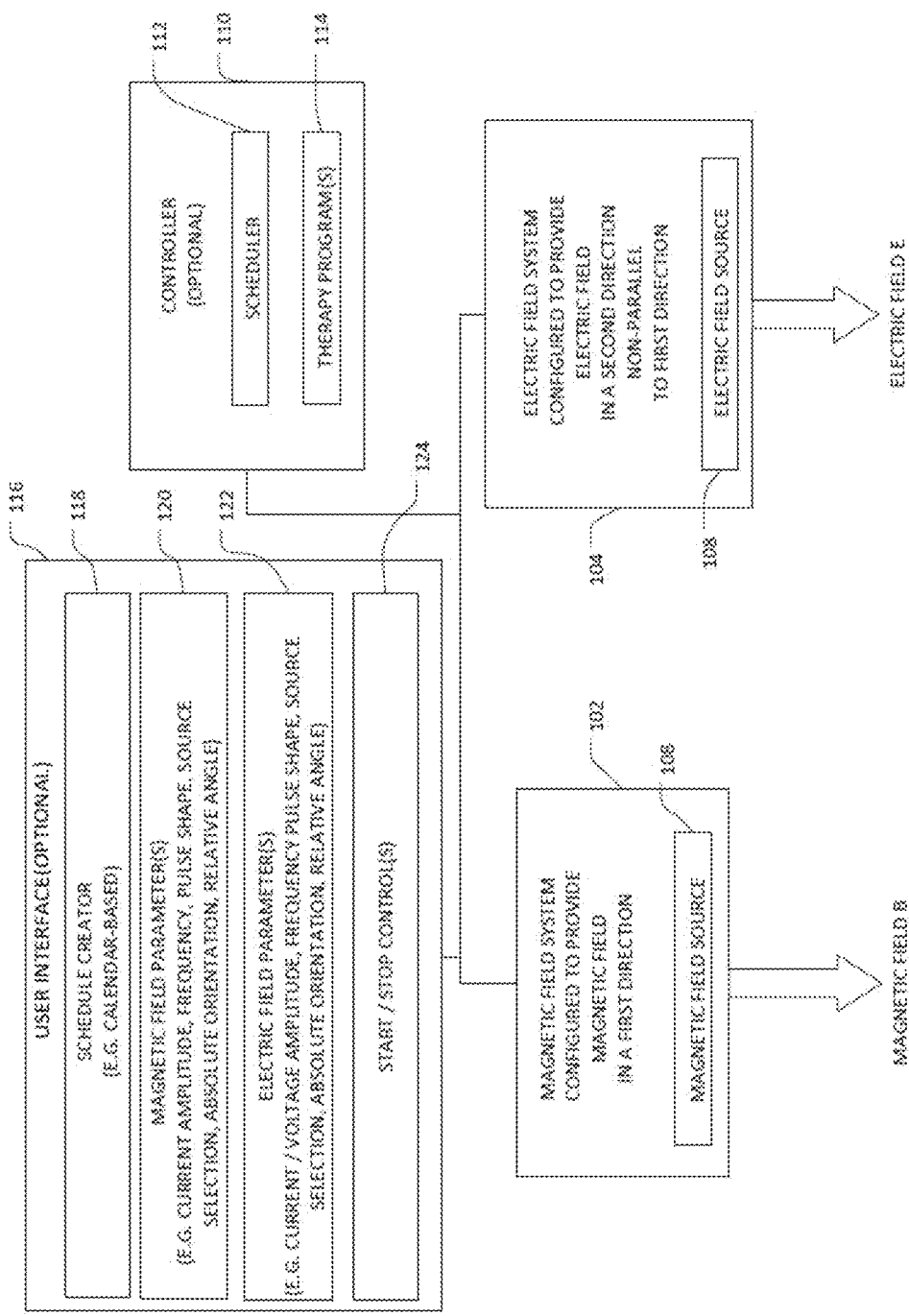
FIG. 1 illustrates, by way of example and not limitation, a system configured to deliver energy (e.g. MNPEF) to tissue as part of a therapy.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Many diseases are caused by an imbalance of free radicals. Free radicals, including reactive oxygen species (ROS) and reactive nitrogen species (RNS), have been implicated in the pathogenesis of a wide range of chronic diseases. The majority of free radicals are produced in the mitochondria as a result of cellular respiration. Free radicals are also generated in other cellular compartments by various enzymes and biological processes. Although free radicals were once thought to be destructive to the cell, there is a growing body of evidence demonstrating that free radicals act as signaling molecules, transmitting crucial information that contributes to the health state of the cell. The therapy protocol disclosed herein has been shown, through experiment, to increase free radicals (e.g. ROS). It has also been shown, through experiment, that at least some of the therapeutic benefits of the therapy are mediated by free radicals (e.g. ROS). Therefore, the present subject matter is believed to provide an effective therapy for diabetes and cancer, as well as for other diseases and conditions such as but not limited to neurological and immune related disorders (e.g. inflammation), and retinovascular disease. The present subject matter is also believed to provide therapeutic benefits against the aging process.

This disclosure is organized to discuss various embodiments for delivering therapy using non-parallel magnetic fields and electric fields, followed by a discussion of applications for magnetic field and non-orthogonal electric fields, and experiment results.

Embodiments for Delivering Therapy Using Non-Parallel Magnetic Field(s) and Electric Field(s)

Various embodiments of the present subject matter deliver a therapy by delivering energy to tissue. A magnetic field system may be configured to provide a magnetic field in a first direction to the tissue. The magnetic field system includes at least one magnetic field source to produce the magnetic field. The magnetic field produced by the at least one magnetic field source may include a magnetic field produced by at least one of a permanent magnet, a magnetic field produced by a temporary magnet or a magnetic field produced by electric current flow through a conductor. An electric field system configured to provide an electric field in a second direction to the tissue, wherein the magnetic field system includes at least one electric field source to provide the electric field and the second direction is non-parallel to the first direction.

The phrase "non-parallel" is defined as neither in the same direction nor in the opposite direction. Thus, directions that are non-parallel form an angle greater than 0 degrees and less than 180 degrees. For example, angles such as less than 170, 160, 150, 140, 130, 120, 110, 100, 90, 80, 70, 60, 50, 40, 30, 20 and 10 degrees can be used. The term "orthogonal" indicates that the directions form an angle that is 90 degrees, and substantially orthogonal indicates that the directions for an angle that is close to 90 degrees (e.g. 80 to 100 degrees, or 85 to 95 degrees). In some embodiments the angle between the electric field (e.g. DC electric field) and the magnetic field (e.g. DC magnetic field) can be described as orthogonal (90 degrees) or substantially orthogonal (such as between 80 and 100 degrees or between 85 and 95 degrees).

The term MNPEF refers to "Magnetic Non-Parallel Electric Field" and is defined as a magnetic field generated by a magnetic field system with at least one magnetic field source and an electric field generated by an electric field system with at least one electric field source. Both the magnetic field and the electric field are delivered to targeted tissue (e.g. a volume of tissue). The vector direction of the magnetic field is non-parallel to the vector direction of the electric field within the targeted tissue. The term MOEF refers to "Magnetic Orthogonal Electric Field" and is a more specific embodiment of MNPEF, where the vector direction of the magnetic field is orthogonal or substantially orthogonal to the vector direction of the electric field within the targeted tissue.

The term patient includes non-human animals and humans. Using the teachings provided herein the devices and methods described can readily be applied to a variety of patients, including for example, humans and companion animals such as dogs, cats, rabbits, hamsters, guinea pigs, pigs, horses and the like.

For purposes of this disclosure, the terms "treatment" and "management" (and similar references) may be used interchangeably. One of ordinary skill in the art will appreciate that treatment regimens include doses given over a period of days, weeks, months or throughout a patient's life time. A dose can be described as the amount of time (duration) that a patient is exposed to MNPEF that has a specified intensity (strength of the non-parallel magnetic and electric fields) during a specified time period. For example, a patient can be exposed to a dose that is 10 hours in duration using a MNPEF of 3 mT and 7 kilivolts/meter (kV/m) every 24 hours. That dose can be given every day for 1 week, 2 weeks, three weeks or longer. One of ordinary skill in the art will appreciate that the treatment regime can be designed by iteratively testing one or more of the physiological parameters described herein to assess the patient's response and then altering the regime as needed.

A magnetic field produced by an alternating current is a changing magnetic field as its direction and magnitude changes with time, whereas a magnetic field produced by a direct current is constant both in magnitude and direction. Similarly, an electric field produced by an alternating current is a changing electric field as its direction and magnitude changes with time, whereas an electric field produced a direct current is constant both in magnitude and direction. The terms $MNPEF^{DC/DC}$ refers to a static or non-varying magnetic field such as a magnetic field generated by a direct current in a wire, and a static or non-varying electric field; and $MNPEF^{AC/DC}$ refers to a magnetic field that varies such as a magnetic field generated by an alternating current in a wire, and a static or non-varying electric field. The first superscript refers to the type of magnetic field used (DC, AC or a combination of the two) and the second term refers to the type of substantially orthogonal electric field (DC, AC or a combination of the two). For example, in some embodiments, a male patient is exposed to $MNPEF^{AC/DC}$ and a female patient is exposed to $MNPEF^{DC/DC}$ (when treating males and/or females) for from about 2-12 hours in a 24 hour period, or from about 3-10 hours, or from about 4-10 hours, or from about 6-8 hours in a 24 hour period. One of ordinary skill in the art will appreciate that the strength of the magnetic field and the electric field can also vary depending upon duration of the treatment and the overall physiological status of the patient. Initial dose ranging treatments can be used to establish the desired duration and intensity of the dose needed to achieve a desired outcome for an individual patient. Also, for purposes of this disclosure, the term "electrostatic" and phrase "direct current electric" (or "DC electric") may be used interchangeably. Throughout this disclosure, "MNPEF" or "MOEF" (i.e., without superscripts) may refer generally to any MNPEF or MOEF (e.g. $MNPEF^{DC/DC}$, $MNPEF^{DC/AC}$, $MNPEF^{AC/DC}$ or $MNPEF^{AC/AC}$.

FIG. 1 illustrates, by way of example and not limitation, a system 100 configured to deliver energy (e.g. MNPEF) to tissue as part of a therapy. The illustrated system includes a magnetic field system 102 and an electric field system 104. The magnetic field system 102 may be configured to provide a magnetic field B to targeted tissue, where a vector direction of the magnetic field in the targeted tissue is in at least a first direction. The letter B is conventionally used to denote a magnetic field or flux density, as illustrated in FIGS. 2B-2G for example. The term "magnetic" is also abbreviated herein with the letter M as used in the MNPEF or MOEF terms. It is noted that the magnetic field may, but need not be, uniform in direction throughout the tissue. That is, the magnetic field may have a complex shape within the tissue, such that the vector direction of the magnetic field within the tissue may vary depending on the position within the tissue. The magnetic field system 102 includes at least one magnetic field source 106 to produce the magnetic field. The magnetic field source(s) 106 may include permanent magnet(s). The magnetic field source(s) 106 may include temporary magnet(s). If a temporary magnet is used, the system will include means to magnetize the temporary magnet via another magnetic source. The magnetic field source(s) 106 may include conductor(s) through which electric current flows to create the magnetic field. The conductor may be a simple wire, a wire loop, or a coil of wire (such as a solenoid). The coil of wire may include a core to enhance the magnetic field generated by the electric current. For example, the magnetic field source(s) may include only one permanent or temporary magnet to produce the magnetic field, and the magnetic field source(s) may include at least two magnets (permanent or temporary), which may be located on opposing sides of the targeted tissue to produce the magnetic field in the first direction to the tissue. More complex arrangement are also contemplated. The magnetic field source(s) may include a conductor which is configured to generate the magnetic field in the first direction to the tissue when current flows through the conductor. The conductor may be a variety of shapes (e.g. line, loop, coil). The conductor may form part of a solenoid. A magnetic core within the coil may be used to strengthen the field. The current in the conductor which forms the magnetic field may be a direct current (DC) or alternating current (AC). Magnetic material with a high magnetic permeability may be used to confine and guide magnetic fields.

The electric field system 104 may include at least one electric field source 108 to provide the electric field and the second direction is non-parallel to the first direction. The electric field source(s) includes an energy source electrically connected to at least one electrode. The energy source may include at least one a voltage source or at least one a current source used to source and/or sink electrical charges onto the electrode(s). The energy source may be configured to provide charge to the electrode(s) via direct current or alternating current. The electrode(s) may include only one electrode (e.g. monopolar), where a reference potential is provided remote to the electrode, or may include multiple electrodes of the same charge polarity. The electrode(s) may include electrodes of opposing polarity (e.g. bipolar or multipolar). For example, electrodes of opposing polarity may be positioned on opposing sides of the tissue to produce the electric field in the second direction to the tissue. The electrodes may have a variety of shapes. An electrode shape may be selected or engineered for use to provide a desired electric field. Multiple electrodes may be used to shape the electric field by controlling an amount of energy provided to individual ones of the electrodes. The electrode(s) may, by way of example and not limitation, include a circular electrode or a plate-shaped electrode. For example, two plate-shaped electrodes of opposing electrical polarity may be on opposing sides of the targeted tissue to provide a relatively uniform electrical field through the targeted tissue.

The electrical field system and/or magnetic field system may be relatively simple systems that are always providing their respective fields. For example, a system may be designed using permanent magnets and an electric field generator that continuously generates an electric field when powered. The electrical field system and/or magnetic field system may be more complex. By way of example, some system embodiments may include sensor(s) that may detect the presence of the patient in an environment (e.g. bed, chair, workstation), and turn on the system in response to detecting the patient's presence near the system. Some embodiments may turn on the system based on a clock/timer (e.g. 10:00 PM), and some embodiments may turn on the system in response to a detecting the patient's presence within a time window (e.g. 10:00 PM to 6:00 AM indicating the patient is in bed, or 9:00 AM to 5:00 PM indicating the patient is at a workstation). Sensor(s) may include a variety of position or motion sensor(s), such as a load sensor to register pressure changes that may be used to detect a patient lying in bed. Sensor(s) may also detect the physiological condition of the patient, which may be used to determine that the patient is in position for the therapy. Other examples may include a temperature sensor, an accelerometer to detect motion or posture, an impedance sensor, a sound sensor, a heart rate sensor, a respiration sensor and activity sensor.

Some system embodiments may include a controller 110 operably connected to at least one of the magnetic field system 102 or electric field system 104. The controller 110 may include a scheduler 112 configured to control timing for generating at least one of the magnetic field or electric field. The controller 110 may include one or more therapy programs 114 used to generate the MNPEF therapy. Each program may include a set of parameters used to generate the magnetic and/or electric field. The set of parameter(s) may include one or more of an amplitude, frequency, pulse shape or source selection. Each of these parameter(s) may affect the resultant fields generated by the electric field system and/or magnetic field system. Source selection for the electric field system may involve selecting different active electrode(s) from a plurality of electrodes to change a field shape and vector direction of the field. Source selection for the magnetic field system may involve changing a location of a magnet or magnet(s), or energizing different conductor(s) from a plurality of conductors to change the field shape and vector direction of the field. Some embodiments may include mechanism(s) to physically move, rotate or re-orientate the magnetic source of the magnetic field system and/or electrode(s) of the electric field system; and the therapy program(s) may implement processes to control those mechanism(s). Various programs may implement protocol(s) to adjust the absolute directions of magnetic field vector direction and/or electric field vector direction, and/or adjust the relative angle between the magnetic and electric field vector directions.

Some system embodiments may include a user interface 116. The user interface 116 may be configured for use by the user to create and/or modify one or more schedules 118 implemented by the controller 110. The user interface may be configured for use by the user to enter, select or adjust various magnetic field parameters 120 such as parameter of the current used to create the magnetic field. These parameters may include amplitude, frequency, pulse shape. Other parameters may include duty cycle, duration, etc. The selectable parameters may include direction (e.g. source selection where selected sources control direction). The user interface may be configured for use by the user to enter, select or adjust various electric field parameters 122. These parameters may include the amplitude of the current or voltage, the frequency and pulse shape. The selectable parameters may include direction (e.g. source selection). The user interface may be configured for use by a user to control the start and/or end of the MNPEF therapy or portions thereof (e.g. start the magnetic field, start electric field, stop the magnetic field and/or stop the electric field) 124. The user interface may be configured for use by a user to control motion, rotation or orientation of the magnetic source(s) and/or electrode(s) so as to enable user control of the absolute directions of magnetic field vector direction and/or electric field vector direction and/or the relative angle of the magnetic and electric field vector directions. The start/stop control may be provided using, by way of example and not limitation, a mechanical button or switch or a selectable graphical user element on a display of the controller 110.

Figure 2A:
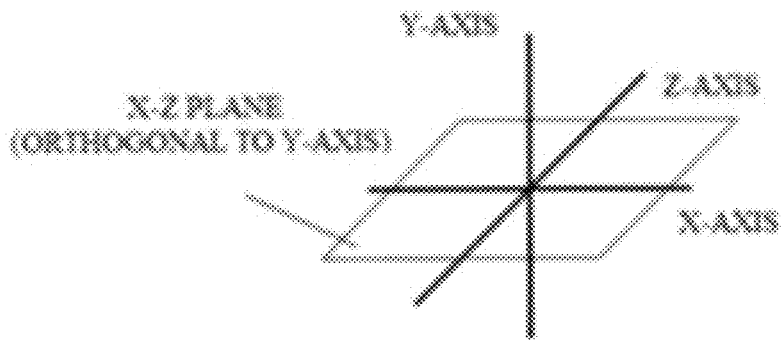
FIGS. 2A-2G illustrates, by way of example and not limitation, some non-parallel vector directions for the electric field E and magnetic field B.

FIGS. 2A-2G illustrates, by way of example and not limitation, some non-parallel vector directions for the electric field E and magnetic field B. FIG. 2A illustrates a 3-dimensional cartesian coordinate system with an X-axis, Y-axis, and Z-axis. In the illustrated figures, the vector direction of the electrical field E is used as the reference and is placed along the Y axis. Of course, vector direction of the magnetic field B may be used as the reference, and the vector direction used as the reference may be placed in any orientation (e.g. on any of the axes). The X-axis and Z-axis define an X-Z plane that is orthogonal to the Y-axis direction.

Figure 2B:
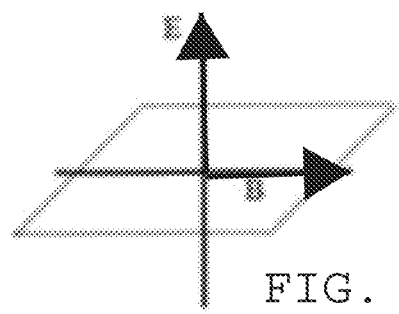
Figure 2C:
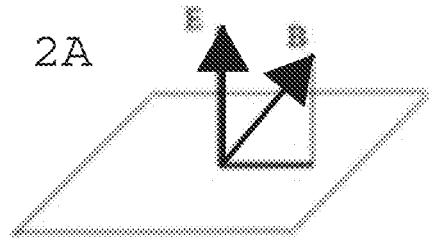

FIG. 2B illustrates an example in which the vector direction of the electric field E is along the Y-axis and the vector direction of the magnetic field B is along the X-axis. This is an example of a MOEF as the vector direction of the magnetic field is orthogonal to the vector direction of the electric field E. FIG. 2C illustrates an example of a MNPEF, where the vector direction of the electric field E is along the Y-axis and the vector direction of the magnetic field B is in the X-Y plane. The vector projection of the magnetic field on the X-Z plane is also illustrated. Since the vector projection is orthogonal to the Y-axis, this may be considered to be the contribution of the magnetic field to an MOEF. This also may be considered to be an indicator for a non-parallel and non-orthogonal field for a MNPEF therapy. Since there is a vector projection on the X-Z plane, the vector direction of the magnetic field B may be considered non-parallel to the vector direction of the electric field E.

Figure 2D:
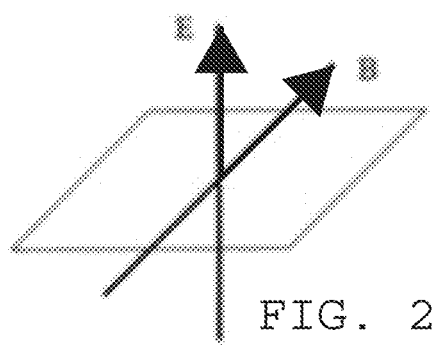
Figure 2E:
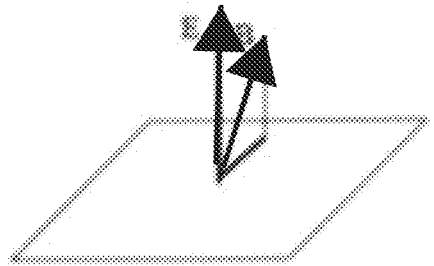

FIG. 2D illustrates an example in which the vector direction of the electric field E is along the Y-axis and the vector direction of the magnetic field B is along the Z-axis. This is another example of a MOEF as the vector direction of the magnetic field B is orthogonal to the vector direction of the electric field E. FIG. 2E illustrates an example of a MNPEF, where the vector direction of the electric field E is along the Y-axis and the vector direction of the magnetic field B is in the Y-Z plane. The vector projection of the magnetic field on the X-Z plane is also illustrated. Since the vector projection is orthogonal to the Y-axis, this may be considered to be the contribution of the magnetic field to an MOEF, and an indicator for a non-parallel and non-orthogonal field for a MNPEF therapy. Since there is a vector projection on the X-Z plane, the vector direction of the magnetic field B may be considered non-parallel to the vector direction of the electric field E.

Figure 2F:
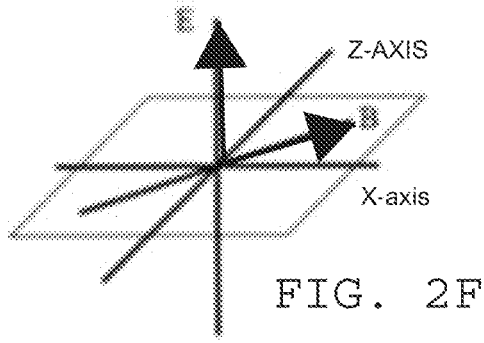
Figure 2G:
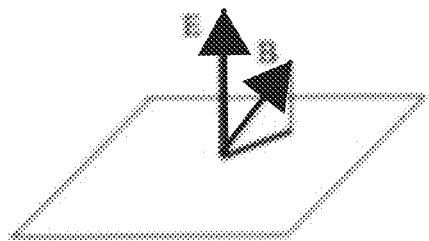

FIG. 2F illustrates an example in which the vector direction of the electric field E is along the Y-axis and the vector direction of the magnetic field B is in the X-Z plane. This is another example of a MOEF as the vector direction of the magnetic field B is orthogonal to the vector direction of the electric field E. FIG. 2F illustrates an example of a MNPEF, where the vector direction of the electric field E is along the Y-axis and the vector direction of the magnetic field B is not in either the X-Y or Y-Z plane. The vector projection of the magnetic field on the X-Z plane is also illustrated. Since the vector projection is orthogonal to the Y-axis, this may be considered to be the contribution of the magnetic field to an MOEF, and an indicator for a non-parallel and non-orthogonal field for a MNPEF therapy. Since there is a vector projection on the X-Z plane, the vector direction of the magnetic field B may be considered non-parallel to the vector direction of the electric field E.

All of the illustrated examples provide an acute angle between the vector directions that is more than 0 degrees and less than or equal to 90 degrees. The electric field E may be in the opposite direction such that the angle between the vector directions is less than 180 degrees but greater than or equal to 90 degrees.

According to various embodiments, the magnitude of the angle $\theta$ between the vector directions of the magnetic field B and the electric field E is within a range where the range may be defined as: 0 degrees<$\theta$<180 degrees; 1 degrees$\leq\theta\leq$179 degrees; 5 degrees$\leq\theta\leq$175 degrees; 10 degrees$\leq\theta\leq$170 degrees; 15 degrees$\leq\theta\leq$165 degrees; 30 degrees$\leq\theta\leq$150 degrees; 45 degrees $\leq<\theta\leq$135 degrees; 60 degrees$\leq\theta\leq$120 degrees; 80 degrees$\leq\theta\leq$100 degrees; and 85 degrees$\leq\theta\leq$95 degrees. According to various embodiments, the magnitude of the angle $\theta$ between the vector directions of the magnetic field B and the electric field E is within a range where the range may be defined as: 0 degrees<$0\leq$90 degrees; 30 degrees$\leq\theta\leq$90 degrees; 1 degree$\leq\theta\leq$90 degrees; 5 degrees$\leq\theta\leq$90 degrees; 10 degrees$\leq\theta\leq$90 degrees; 15 degrees$\leq\theta\leq$90 degrees; 30 degrees$\leq\theta\leq$90 degrees; 45 degrees$\leq\theta\leq$90 degrees; 60 degrees$\leq\theta\leq$90 degrees; 80 degrees$\leq\theta\leq$90 degrees; and 85 degrees$\leq\theta\leq$90 degrees. According to various embodiments, the magnitude of the angle $\theta$ between the vector directions of the magnetic field B and the electric field E is within a range where the range may be defined as: 90 degrees$\leq\theta<$180 degrees; 90 degrees$\leq\theta\leq$179 degrees; 90 degrees$\leq\theta\leq$175 degrees; 90 degrees$\leq\theta\leq$170 degrees; 90 degrees$\leq\theta\leq$165 degrees; 90 degrees$\leq\theta\leq$150 degrees; 90 degrees$\leq\theta\leq$135 degrees; 90 degrees$\leq\theta\leq$120 degrees; 90 degrees$\leq\theta\leq$100 degrees; and 90 degrees$\leq\theta\leq$95 degrees.

According to various embodiments, the strength of the magnetic field may be within a range where: the range is 0 to 0.1 mT, the range is 0.1 mT to 1 mT, the range is 1 mT to 10 mT or the range is 10 mT to 100 mT. In some embodiments, the strength of the magnetic field may be in the range from 0 to 100 mT, the range from 0.1 mT to 10 mT, the range from 0.1 mT to 1 mT or the range from 1 mT to 10 mT. According to various embodiments, the strength of the magnetic field may be at least 0.5 mT, or within a range from 0.5 mT to 5 mT.

According to various embodiments, the strength (amplitude) of an externally-applied electric field may be within a range where: the range is 0 to 100 V/m, the range is 100 V/m to 1000 V/m, the range is 1 kV/m to 10 kV/m, the range is 10 kV/m to 100 kV/m, or the range is 100 kV/m to 1000 kV/m. In some embodiments, the range is from 0 to 1000 kV/m, the range is from 100 V/m to 1000 kV/m, the range is from 100 V/m to 100 kV/m, the range is from 1 kV/m to 1000 kV/m, the range is from 1 kV/m to 100 kV/m, and the range is from 10 kV/m to 1000 kV/m. According to various embodiments, the strength (amplitude) of an externally-applied electric field may be at least 1 V/m, within a range from 0.1 to 6 kV/m, or with in a range from 0.1 to 20 kV/m. According to various embodiments, the strength (amplitude) of an externally-applied electric field may be between 2 kV/m to 30 kV/m. Such a range may be beneficial for a therapy to treat diabetes. According to various embodiments, the strength (amplitude) of an externally-applied electric field may be between 2 kV/m to 60 kV/m. Such a range may be beneficial for a therapy to treat cancer.

Weaker field may be applied when an electric field is applied directly to a body. For example, some embodiments that includes a patch for application to a body may be configured to deliver up to a 500 V/m electric field. According to various embodiments, the strength (amplitude) of an externally-applied electric field applied directly to tissue may be within a range where: the range is between 0 to 10 uV/mm; the range is between 10 uV/mm to 100 uV/mm; the range is between 100 uV/mm to 1000 uV/mm; the range is between 1 mV/mm to 10 mV/mm; the range is between 10 mV/mm to 100 mV/mm; or the range is between 100 mV/mm to 1000 mV/mm. In some embodiments, the range is from 0 to 1000 mV/mm, the range is from 10 uV/mm to 1000 mV/mm, the range is from 100 uV/mm to 1000 mV/mm, the range is from 1 mV/mm to 1000 mV/mm, the range is from 10 mV/mm to 1000 mV/mm, the range is from 100 mV/mm to 1000 mV/mm, the range is from 10 uV/mm to 100 mV/mm, the range is from 100 uV/mm to 100 mV/mm, the range is from 1 mV/mm to 100 mV/mm, the range is from 10 mV/mm to 100 mV/mm, the range is from 10 uV/mm to 10 mV/mm, the range is from 100 uV/mm to 10 mV/mm, the range is from 1 mV/mm to 10 mV/mm, the range is from 10 uV/mm to 1 mV/mm, or the range is from 100 uV/mm to 1m V/mm. For example, cells appear to be treated when an electric field of around 1 V/m (or 1 mV/mm) is directly applied using stainless steel or titanium electrodes which have a similar conductivity. Thus, ranges of 0.1 mV/mm to 10 mV/mm, ranges of 0.5 mV/mm to 5 mV/mm or ranges of 0.8 mV/mm to 2 mV/mm may be desirable for some applications.

It is believed that there may be patient-to-patient variations, as body type (e.g. obese v. slender) and environment (e.g. number of conductors near patient) may affect the fields.

According to various embodiments, magnetic fields and/or electric fields may have a frequency within a range from 0 to 100 Hz, 100 Hz to 1000 Hz, 1 kHz to 10 kHz, 10 kHz to 1000 kHz, and 1 MHz to 1000 MHz. It is noted that a frequency of 0 is constant field, and may be referred to as a DC (Direct Current) field. According to various embodiments, magnetic fields and/or electric fields may have a frequency within a range from 0 to 1000 MHz, within a range from 100 Hz to 1000 MHz, within a range from 1 kHz to 1000 MHz, within a range from 10 kHz to 1000 MHz, within a range from 100 kHz to 1000 MHz, within a range from 100 Hz to 1 MHz, within a range from 1 kHz to 1 MHz, within a range from 10 kHz to 1 MHz, within a range from 100 kHz to 1 MHz, within a range from 100 Hz to 100 kHz, within a range from 1 kHz to 100 kHz, within a range from 10 kHz to 100 kHz, within a range from 100 Hz to 10 kHz, or within a range from 1 kHz to 10 kHz.

Figure 3:
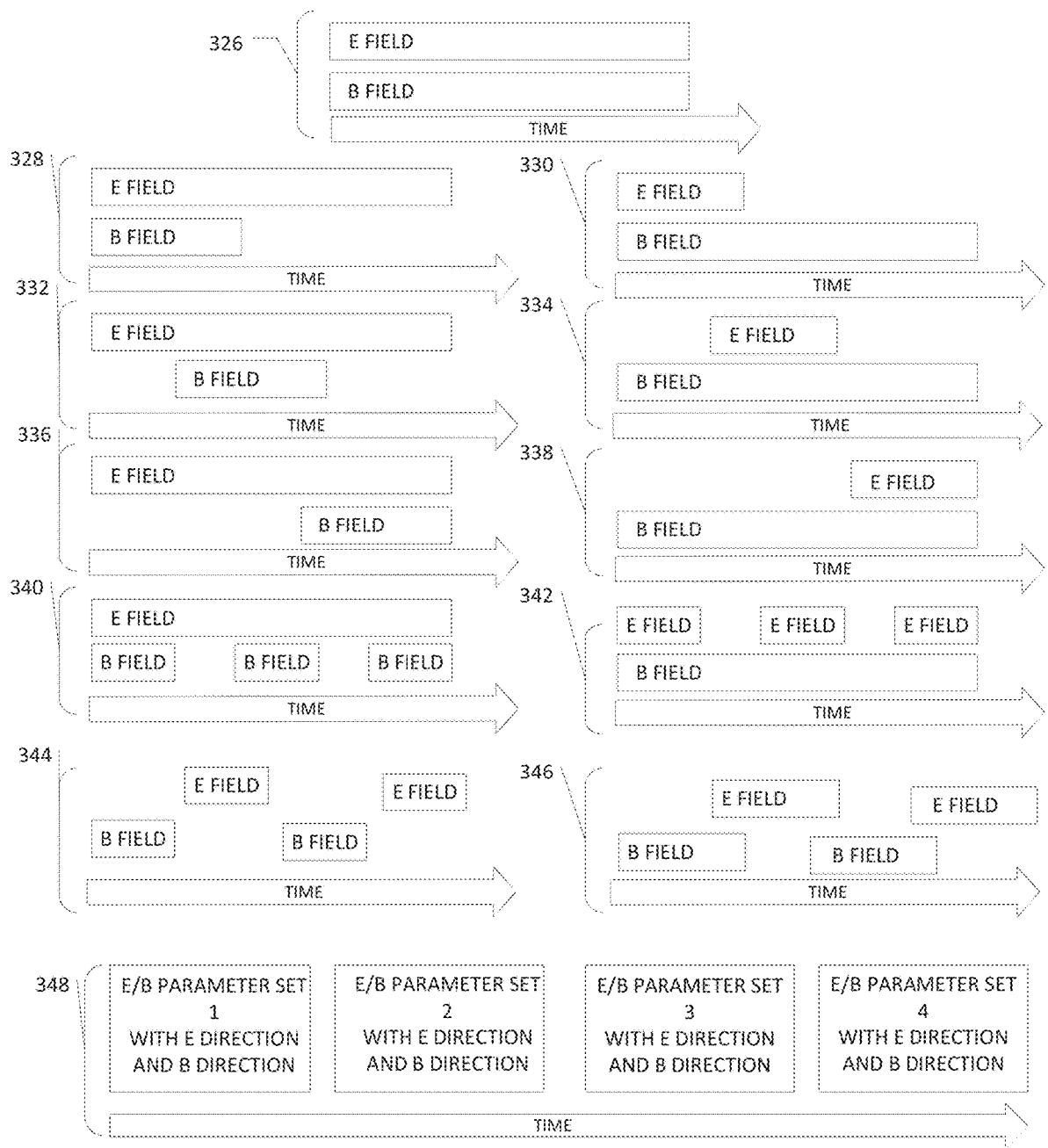
FIG. 3 illustrates, by way of example and not limitation, various timing diagrams for delivering the magnetic field ("magnetic field component") and delivering the electric field ("electric field component") for the MNPEF therapy.

FIG. 3 illustrates, by way of example and not limitation, various timing diagrams for delivering the magnetic field ("magnetic field component") and delivering the electric field ("electric field component") for the MNPEF therapy. These therapies may be initiated, for example, by manually or automatically switching on the electric field system and/or magnetic field system. For example, some embodiments may be worn such as embodiments incorporated into articles of clothing (e.g. vests, caps, and the like) Some embodiments provide magnetic field components that are always on (e.g. permanent magnets). Some embodiments may provide magnetic field components and/or electric field components that are always one or nearly always one upon set up, such as a system set up to deliver MNPEF therapy whenever the patient is in a certain environment (e.g. bed, chair, work station, under blanket, etc.). Some embodiments are programmed or otherwise automated to schedule delivery of at least one of the magnetic field component or the electric field component of the MNPEF therapy. Some embodiments operate only upon enabling conditions (e.g. at least one of time of day, detected patient location, detected patient posture, or detected patient activity or inactivity).

Timing diagram 326 illustrates concurrent delivery of the magnetic field B component and electric field E component. The illustrated timing diagram 326 may, but does not necessarily, represent a dose (e.g. daily dose) of MNPEF. Both fields may be automatically or manually started and stopped at, or nearly at, the same times. As is also illustrated, the duration of the electric field E component may be the same or approximately the same as the duration for the magnetic field B component for a dose of MNPEF.

Timing diagram 328 illustrates that the magnetic field B component and electric field E component are initiated at, or nearly at, the same time, but that the magnetic field B is terminated earlier than the electric field E. The illustrated timing diagram 328 may, but does not necessarily, represent a dose (e.g. daily dose) of MNPEF. As is also illustrated, the duration of the electric field E component may be longer than the duration for the magnetic field B component for a dose of MNPEF.

Timing diagram 330 illustrates that the magnetic field B component and electric field E component are initiated at, or nearly at, the same time, but that the electric field E component is terminated earlier than the magnetic field B component. The illustrated timing diagram 330 may, but does not necessarily, represent a dose (e.g. daily dose) of MNPEF. As is also illustrated, the duration of the magnetic field B component may be longer than the duration for the electric field E component for a dose of MNPEF.

Timing diagram 332 illustrates that the magnetic field B component is initiated after the electric field E component and is terminated before the electric field E component. The illustrated timing diagram 332 may, but does not necessarily, represent a dose (e.g. daily dose) of MNPEF. As is also illustrated, the duration of the magnetic field B component may be shorter than the duration for the electric field E component for a dose of MNPEF.

Timing diagram 334 illustrates that the electric field E component is initiated after the magnetic field B component and is terminated before the magnetic field B component. The illustrated timing diagram 334 may, but does not necessarily, represent a dose (e.g. daily dose) of MNPEF. As is also illustrated, the duration of the magnetic field B component may be longer than the duration for the electric field E component for a dose of MNPEF.

Timing diagram 336 illustrates that the magnetic field B component is initiated after the electric field E component and is terminated when, or nearly when, the electric field E component is terminated. The illustrated timing diagram 336 may, but does not necessarily, represent a dose (e.g. daily dose) of MNPEF. As is also illustrated, the duration of the magnetic field B component may be shorter than the duration for the electric field E component for a dose of MNPEF.

Timing diagram 338 illustrates that the electric field E component is initiated after the magnetic field B component and is terminated when, or nearly when, the magnetic field B component is terminated. The illustrated timing diagram 338 may, but does not necessarily, represent a dose (e.g. daily dose) of MNPEF. As is also illustrated, the duration of the magnetic field B component may be longer than the duration for the electric field E component for a dose of MNPEF.

Timing diagram 340 illustrates that more than one instance of the magnetic field B component may be provided when one instance of the electric field E component is provided. One of the magnetic field B components may, but need not, be initiated when the electric field component is initiated. Other embodiments initiate the magnetic field B component before or after the electric field E component is initiated. The illustrated timing diagram 340 may, but does not necessarily, represent a dose (e.g. daily dose) of MNPEF. The magnetic field B components may be periodically delivered, or may be scheduled or otherwise intermittently delivered for a dose of MNPEF.

Timing diagram 342 illustrates that more than one instance of the electric field E component may be provided when one instance of the magnetic field B component is provided. One of the electric field E components may, but need not, be initiated when the magnetic field component is initiated. Other embodiments initiate the electric field E component before or after the magnetic field B component is initiated. The illustrated timing diagram 342 may, but does not necessarily, represent a dose (e.g. daily dose) of MNPEF. The electric field E components may be periodically delivered, or may be scheduled or otherwise intermittently delivered for a dose of MNPEF.

Both timing diagram 344 and timing diagram 346 illustrate that multiple instances of the magnetic field B component and electric field E component may be delivered an interleaved with each other. Timing diagram 344 illustrates that the magnetic field B component and electric field component E do not overlap, whereas timing diagram 346 illustrates that the magnetic field B component and electric field component E do overlap. Each of the illustrated timing diagrams 334 and 336 may, but does not necessarily, represent a dose (e.g. daily dose) of MNPEF. Also, it is noted that interleaved instances of the magnetic field B components and electric field E components do not have to have a 1:1 ratio. That is, magnetic field B components may be interleaved with electric field E components where there are fewer magnetic field B components than electric field E components, and electric field E components may be interleaved with magnetic field B component where there are fewer electric field E components.

Timing diagram 348 illustrates that multiple programs may be delivered over a time period. A programmed schedule may control when each program is initiated and terminated. within each program, there timing between the electric field E component(s) and magnetic field component(s) may be controlled, such as illustrated in but not limited to timing diagrams 326, 328, 330, 332, 334, 336, 338, 340, 342, 344 and 346. Each program may be considered to be a distinct parameter set for at least one of the electric field E component or magnetic field B component. Each of the programs may keep the same vector directions for the electric field component and magnetic field component, but change other parameters such as amplitude, pulse shape, frequency, etc. In some embodiments, at least some of the programs change the vector direction for at least one of the electric field E component or the magnetic field B component, with or without other parameter changes. The vector direction changes may cause the relative angle between the vector direction of the magnetic field B and the vector direction of the electric field E to change. In some embodiments, the vector direction changes are designed to change the absolute angle with respect to the targeted tissue, but keep the same or nearly the same relative angle between the vector direction of the magnetic field B and the vector direction of the electric field E. Vector directions may be changed by selecting different magnetic field source(s) and/or electric field source(s). By way of example and not limitation, differently-positioned and/or shaped electrode(s) may be energized to change the vector direction of the electric field E. Similarly, differently-positioned and/or shaped conductor(s) may be energized to conduct current to change the vector direction of the magnetic field B. Some embodiments may include mechanism(s) to physically move, rotate or re-orientate the magnetic source of the magnetic field system and/or electrode(s) of the electric field system; and the therapy program(s) may implement processes to control those mechanism(s).

Figure 4:
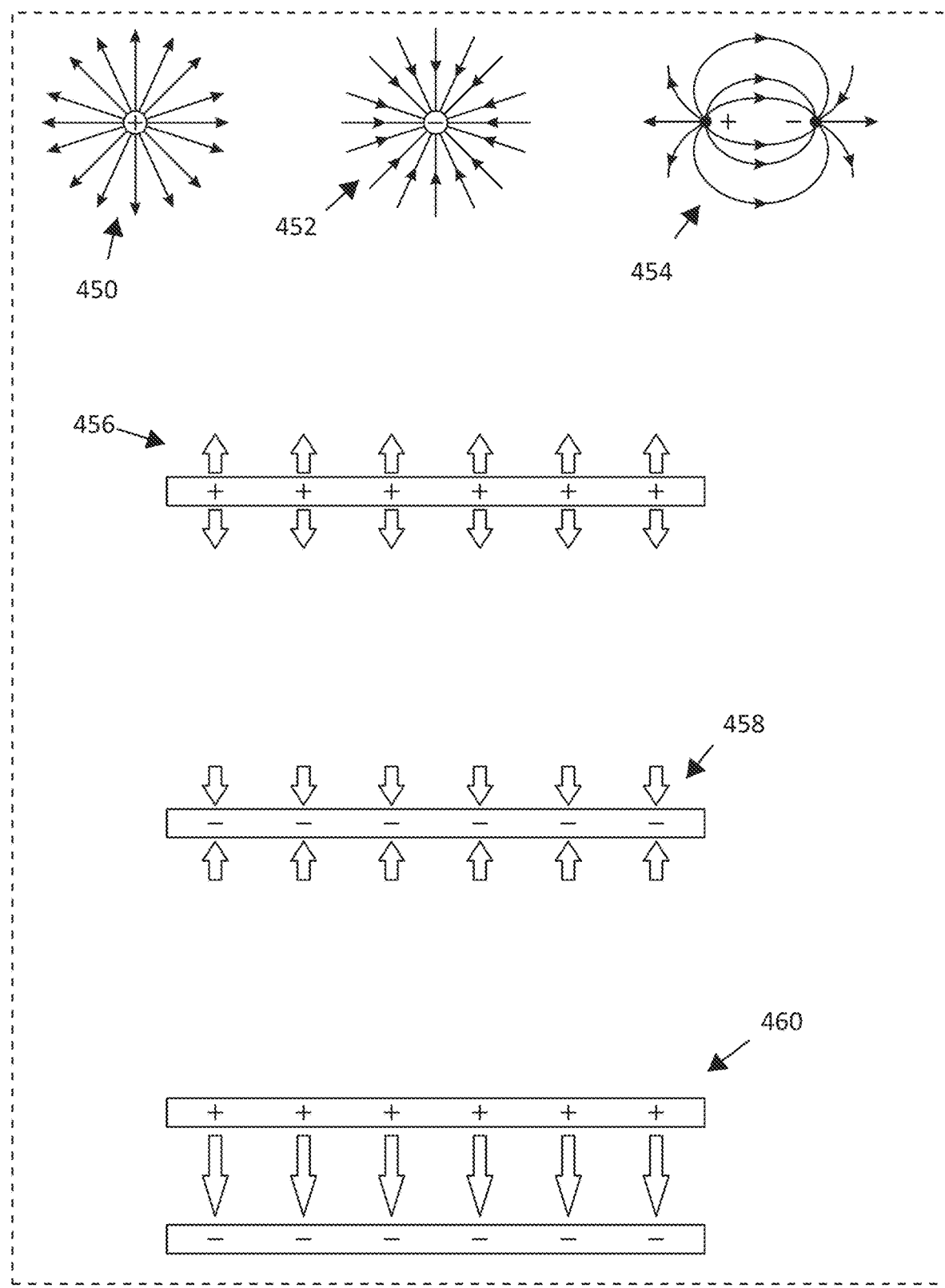
FIG. 4 illustrates, by way of example and not limitation, various examples of electric field shapes that may be generated by different electrode shapes and different charges applied to the electrode shapes.
Figure 5:
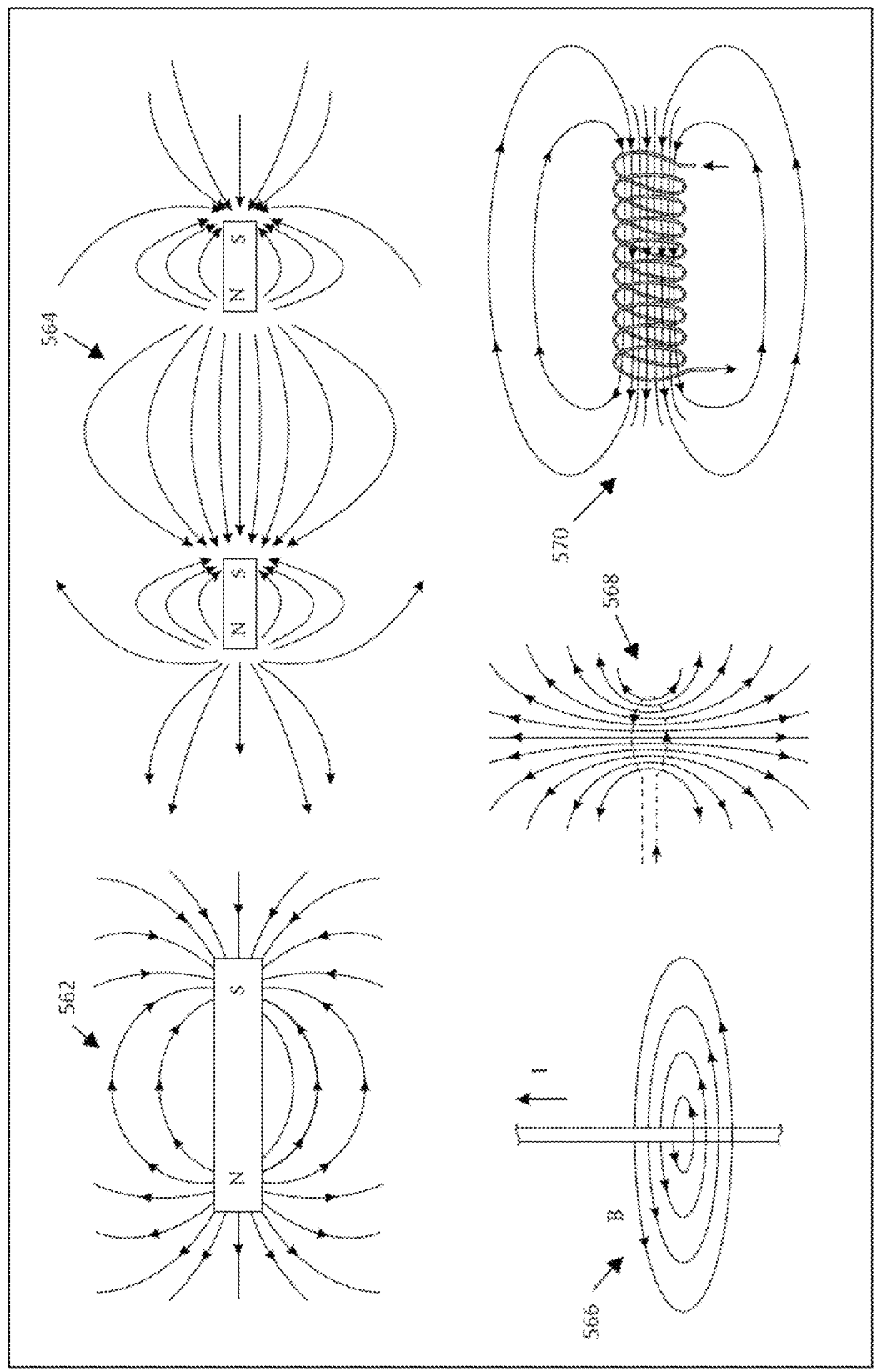
FIG. 5 illustrates, by way of example and not limitation, various examples of magnetic field shapes that may be generated by different magnetic field sources.

The present subject matter delivers MNPEF therapy to achieve the benefits described herein. Electric field source(s) and magnetic field source(s) may be configured and positioned to provide the desired vector fields in the targeted tissue. FIG. 4 illustrates, by way of example and not limitation, various examples of electric field shapes that may be generated by different electrode shapes and different charges applied to the electrode shapes. A small, circular button electrode may produce a similar electric field as a point charge. An electric field for a positive point charge is illustrated at 450, and an electric filed for a negative point charge is illustrated at 452. Some embodiments may provide the electric field in a monopolar configuration in which only one electrode is positioned to provide the electric field to the targeted tissue. The reference/return electrode may be positioned away from the electrode such as on the housing of the stimulator device. An electric field for a dipole, consisting of a positive point charge and a negative point charge, is illustrated at 454. It is noted that the electric field lines between the dipole become more linear. Thus, the dipole may be positioned so that the targeted tissue is generally centered on the dipole. Some embodiments may use one or more plate-shaped electrodes. One positively-charged, plate-shaped electrode is illustrated at 456, and one negatively-charged, plate-shaped electrode is illustrated at 458. the electric field extends generally uniformly from the surface of the plate. Some embodiments may use two oppositely-charged, plate-shaped electrodes to provide a relatively uniform and focused electric field between the two plates, as generally illustrated at 460. The oppositely-charged, plate-shaped electrodes may be placed on opposing sides of the targeted tissue (or on opposing sides of the patient) so that the fields extend through the targeted tissue. FIG. 5 illustrates, by way of example and not limitation, various examples of magnetic field shapes that may be generated by different magnetic field sources. The magnetic source(s) may be, but do not have to be, positioned so that approximately linear magnetic field vectors pass through the targeted tissue. The magnetic field lines for a simple bar-type magnet is illustrated at 562. The vector directions of the magnetic field approximate linear vectors between the two poles and adjacent to the magnet, or adjacent to the two poles on the end of the magnet. The magnetic field lines for two magnets is illustrated at 564. The vector directions of the magnetic field approximate linear vectors between the two magnets. The magnetic field B lines induced by current flow (I) through a conductor is generally illustrated at 566. The induced magnetic field is generally concentric about the wire. The conductor may be positioned and shaped to provide the desired magnetic field to the targeted tissue. For example, current flow through a conductor loop generates a magnetic field as generally illustrated at 568, and current flow through a coiled conductor generates a magnetic field as generally illustrated at 570. A solenoid, for example, uses current flow through a tightly wound coil of wire to provide a magnetic field. Additional materials inside and outside of the coil may be used to further shape the magnetic field.

Figure 6:
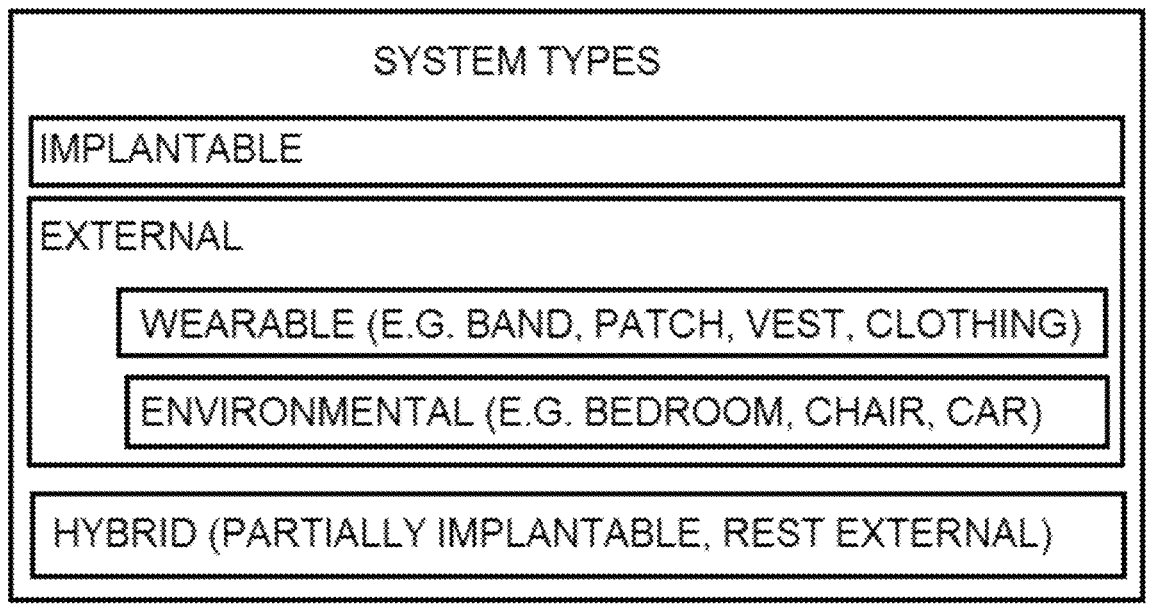
FIG. 6 illustrates different system types for the MNPEF system.

FIG. 6 illustrates different system types for the MNPEF system. The electric field system may be an implantable system including all implantable components, or may be an external system including all external components, or may be a hybrid system where only some of the components are implantable the remainder or external. Similarly, the magnetic field system may be an implantable system including all implantable components, or may be an external system including all external components, or may be a hybrid system where only some of the components are implantable the remainder or external. Implantable systems may be used to deliver the MNPEF therapy to an ambulatory patient. External systems may be wearable systems or environmental systems. A wearable system is configured to be carried by an ambulatory patient. The system may be incorporated into a band or strap that can be secured around a patient or at least a targeted body part of the patient, a patch that can be adhered to the skin or otherwise secured to the patient's body, a vest, a cap, or other article of clothing and a component attached to the clothing. Environmental systems are designed to be set up in an environment that the patient is in on a regular basis. Thus, a bedroom, chair, work station, or car are examples of environments that may be set up with a magnetic field system and an electric field system to deliver the MNPEF therapy. The MNPEF therapy may be externally applied to the ambulatory patient. A hybrid system includes some implantable components. For example, the magnet(s) or current conductors used by the magnetic field system may be implanted to more precisely target the magnetic field to the targeted tissue. Similarly, the electrode(s) used by the electric field system may be implanted to more precisely target the electric field to the targeted tissue. The controller 110 illustrated in FIG. 1 may be implantable, may be external or may be distributed so as to be partially implantable and partially external. An example of a distributed controller may include a separate controller for each of the magnetic field system and electric field system, where each controller performs some of the functions to deliver the MNPEF therapy.

The system may be configured, according to various embodiments, to collect data regarding patient adherence. This data may reflect the duration that the MNPEF therapy is delivered, or another indicator of a delivered therapy dose over time periods. For an environmental system such as a bed, the system may use a sensor to register pressure changes indicating patient is in bed. Other sensor(s) may be used to detect location. The system may track on/off times and/or energy use when the patient is in the environment for the therapy. A wearable device may register current flow or temperature to indicate whether the device is worn properly. Wearable device and implantable devices may track on/off times and energy use. Data can be transmitted to device(s) used by physicians, patient or another party to track patient adherence. Data can be displayed on the device and/or transmitted via near field communication (NFC), Bluetooth, wireless internet or wireless transfer of another kind.

Some system embodiments may include sensor(s) worn by the patient to detect the electric field and/or magnetic field, which may be used to indicate when therapy is being delivered to patient. The sensor data may be stored and/or transmitted to device(s) used by physicians, patient or another party to track patient adherence. The sensor(s) may simply track when the patient is in an environment when the strength of the field(s) are above a threshold. The sensor(s) may also determine and track dosing information. The sensor(s) may also determine and track the strength of the field(s) and/or the absolute and/or relative direction of the field(s). Some embodiments use this information to calibrate the MNPEF therapy for patient. Information from other patients (including dosing information and/or therapeutic effects of the MNPEF therapy) may also be used to calibrate the MNPEF therapy for individual patients. Sensor(s) used to track dosing may be externally worn or may be implanted proximate to the targeted tissue, regardless of whether the fields are internally or externally generated.

Figure 7:
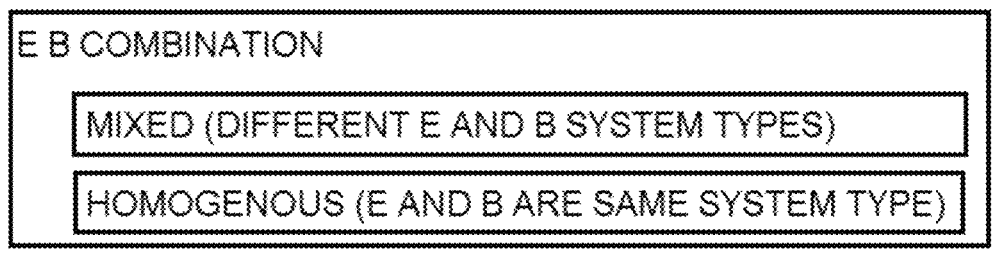
FIG. 7 illustrates combination types for electric field combinations and magnetic field combinations.

FIG. 7 illustrates combination types for electric field combinations and magnetic field combinations. A mixed system combination indicates that one of the electric field system or magnetic field system is one of the implantable, external (wearable or environmental) or hybrid types, and the other one of the electric field system or magnetic field system is another one of the implantable, external (wearable or environmental) or hybrid types. A homogenous system combination indicates that both the electric field system and the magnetic field system are the same system type (implantable, external (wearable or environmental) or hybrid types).

Figure 8:
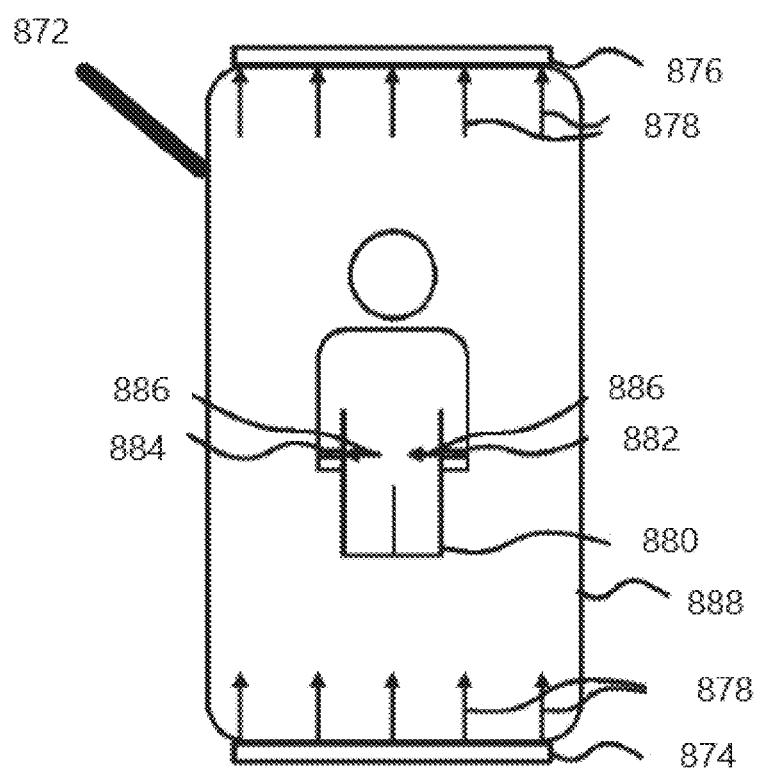
FIG. 8 illustrates, by way of example and not limitation, a schematic diagram illustrating a system for delivering MNPEF.

FIG. 8 illustrates, by way of example and not limitation, a schematic diagram illustrating a system 872 for delivering MNPEF. The system 872 may comprise a direct current (DC) magnetic field system 874, 876 that generates and applies a DC magnetic field 878 to a patient 880; and a DC electric field system 882, 884 that generates and applies a DC electric field 886 to the patient 880 in a field direction substantially orthogonal to a direction of the DC magnetic field 878. The system 872 may be implemented in an environment of a bed 888.

Figure 10B:
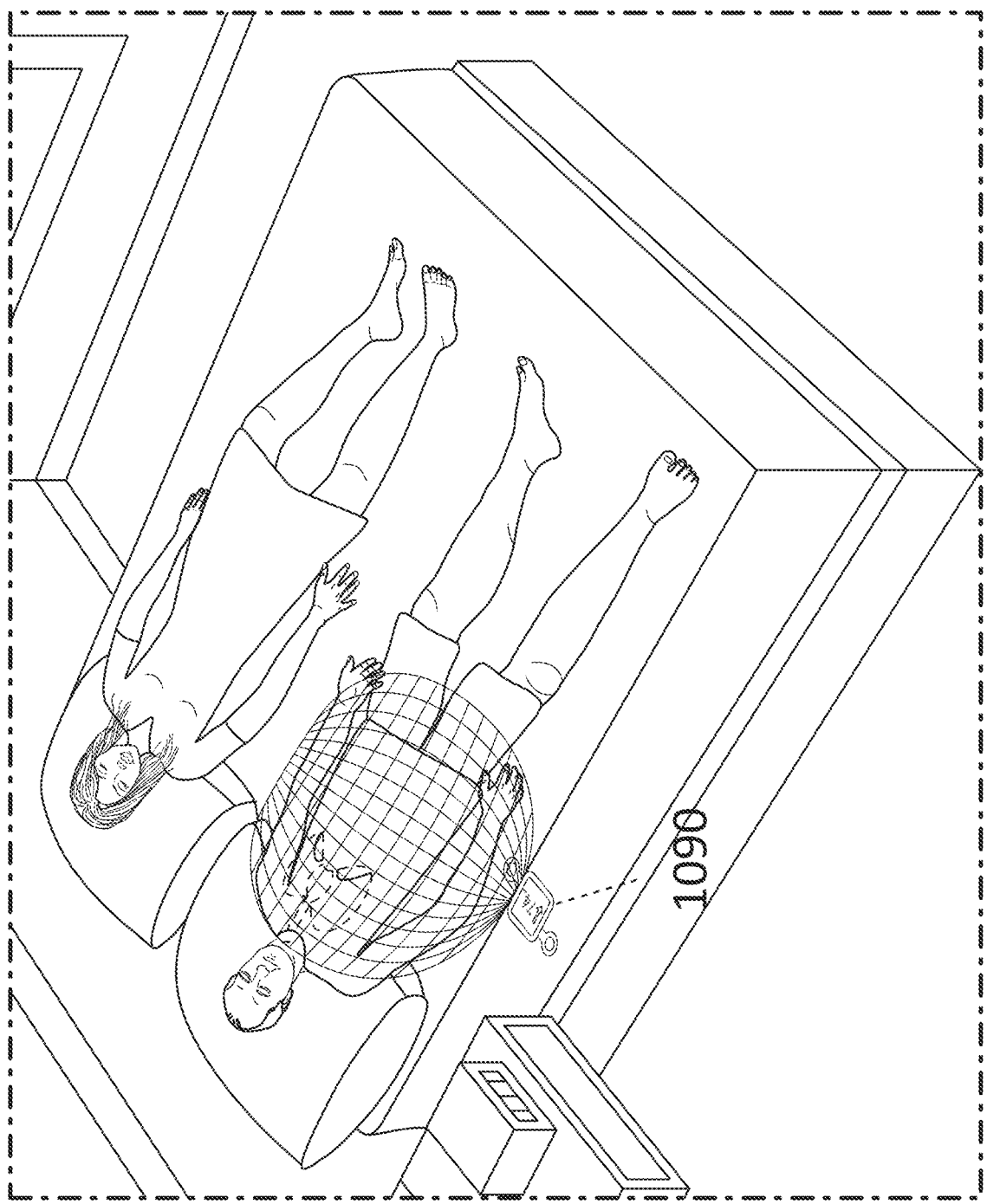

FIGS. 9A-9B illustrate, by way of example and not limitation, embodiments of a system in the form of a patch-like device. The system illustrated in FIG. 9B generally includes the same components as the system in FIG. 9A. The size and shape of the device may be engineered to provide the desired magnetic field and desired electric field. The device 990 may include electrodes 992 that function as part of the electric field source. The device 990 may also include a magnetic field source 994, which may be implemented as a permanent magnets within the device housing or may be implemented as a current-induced magnet within the device. For example, some embodiments using a conductor loop (or coiled conductor) around the perimeter of the device housing to generate a magnetic field generally orthogonal to the major surfaces of the device. The device may be incorporated to perform other functions. For example, the illustrated device provides a blood glucose readout 996, which may be obtained (e.g. via wireless communication) from a glucose sensor (finger prick meter or wearable continuous blood glucose sensor). Some embodiments incorporate a blood-glucose sensor into the device so that the blood glucose sensor may be percutaneously inserted to the patient. FIGS. 10A-10B illustrate the patch-like device of FIG. 9A implemented as a wearable device adhered or otherwise attached directly or indirectly to the patient and as an environmental device under the bed mattress, respectively. Other patient parameter(s) (e.g. biomarker(s)) may be sensed to indicate the state of the disease or patient condition. The patient parameter(s) may be directly indicative of a symptom of the disease or condition, or may be a surrogate of a parameter indicative of a symptom of the disease or condition.

Figures 11A, 11B, 11C:
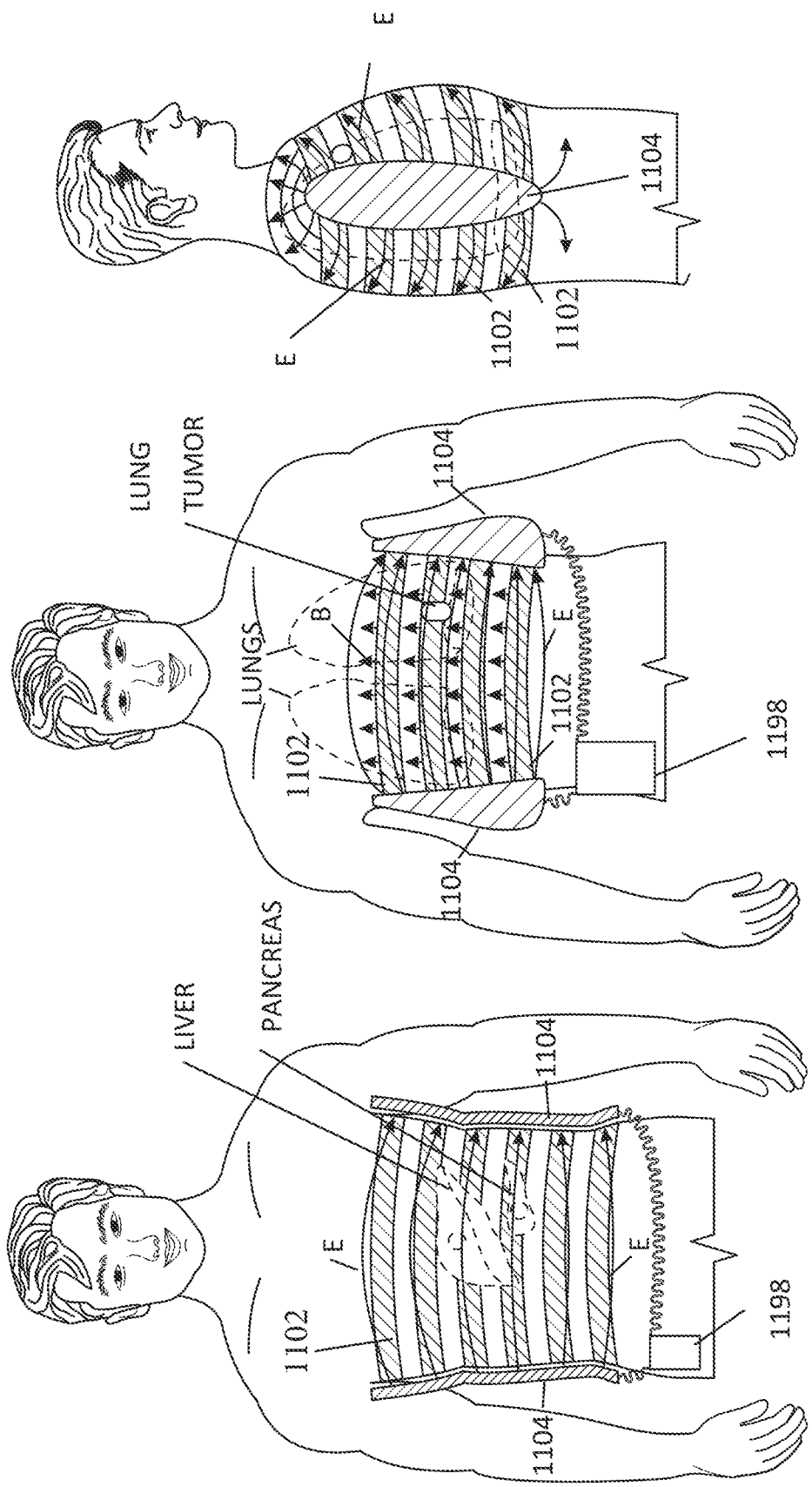
FIGS. 11A-11C illustrate an embodiment of a wearable MNPEF system in the form of vest.

FIGS. 11A-11C illustrate an embodiment of a wearable MNPEF system in the form of vest. FIG. 11A illustrates that the vest is configured to deliver the MNPEF therapy to the liver and/or pancreas such as may be useful as a therapy for diabetes. The depicted embodiment may also be configured to deliver MNPEF therapy to a tumor residing within tissues in the abdomen (e.g. liver, pancreas, stomach, gallbladder, sarcoma, intestines and/or prostate). FIG. 11B illustrates that the vest is configured to deliver the MNPEF therapy to a cancerous tumor in the lung. FIG. 11 C illustrates a side view of the vest. The system may include a power source or sources 1198 to provide electrical power for the electric field system and possibly provide power for the magnetic field system. The magnetic field system may comprise permanent magnets or may comprise a conductor wrapped in a coil 1102 such that the coil surrounds the patient when worn. The magnetic field vector may be in the rostral-caudal direction (e.g. toward the head). The electric field system may include two electrodes 1104 on opposing sides of the patient (e.g. one plate-shaped electrode under each arm) electrically-connected to the power source 1198. The electric field vector may be oriented laterally such that the magnetic and electric fields may be approximately orthogonal. However, the system may be engineered to provide the fields in other non-parallel vector directions.

FIG. 12 illustrates an embodiment of a wearable MNPEF system as an article to be worn on the head. For example, the wearable device may be incorporated into a hat or a head band. Similar to the vest illustrated in FIGS. 11A-11c, the MNPEF system to deliver therapy to the head may include a power source or sources 1198 to provide electrical power for the electric field system and possibly provide power for the magnetic field system. The magnetic field system may comprise permanent magnets or solenoids 1202, and the electric field system may include electrodes 1204. The solenoids or magnets 1202 may be oriented to provide magnetic field vectors in the lateral direction, and the electrodes may be oriented to provide the electric field vectors in the anterior-posterior direction. However, the system may be engineered to provide the fields in other non-parallel vector directions.

FIGS. 13A-B illustrate an embodiment of an implantable MNPEF system, illustrated by way of example and not limitation, around a tumor in an arm. The implantable device 1306 includes a power source or sources 1308, solenoids or magnet(s) 1310 to generate a magnetic field, and plate-shaped electrodes 1312 on opposing sides of the tumor. The solenoids or magnets and the electrodes may be oriented to provide orthogonal, or approximately orthogonal, vector directions. However, the system may be engineered to provide the fields in other non-parallel vector directions.

FIGS. 14A-B illustrate an embodiment of an environmental MNPEF system, illustrated by way of example and not limitation, around a patient's bed. The system includes a power source or sources 1414 to provide electrical power for the electric field system and possibly provide power for the magnetic field system. The magnetic field system may comprise permanent magnets or solenoids 1416 along the sides of the bed (e.g. attached to the bed or bedframe), and the electric field system may include electrodes 1418 above and beneath the patient. The electrodes 1418 beneath the patient may also be beneath a pad or mattress. The solenoids or magnets 1416 may be oriented to provide magnetic field vectors in the lateral direction, and the electrodes 1418 may be oriented to provide the electric field vectors in the vertical direction (e.g. dorsal-ventral if patient is lying on back). However, the system may be engineered to provide the fields in other non-parallel vector directions.

FIGS. 15A-B illustrate an embodiment of an environmental MNPEF system, illustrated by way of example and not limitation, around a patient's bed. The system includes a power source or sources 1514 to provide electrical power for the electric field system and possibly provide power for the magnetic field system. The magnetic field system may comprise permanent magnets or solenoids 1516 along the sides of the bed (e.g. attached to the bed or bedframe), and the electric field system may include electrodes 1518. The solenoids or magnets 1516 may be oriented to provide magnetic field vectors in the lateral direction, and the electrodes 1518 may be oriented to provide the electric field vectors in the longitudinal direction (e.g. superior-inferior or rostral-caudal). However, the system may be engineered to provide the fields in other non-parallel vector directions.

Figure 16:
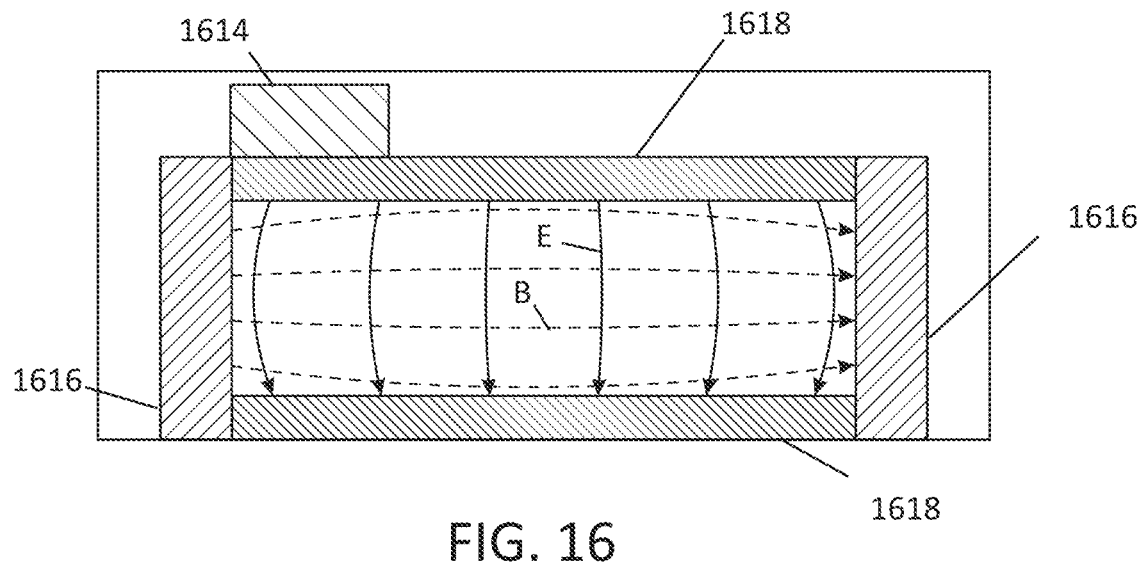
FIG. 16 illustrates an embodiment of an environmental MNPEF system, illustrated by way of example and not limitation, incorporated into furniture such as a couch.

FIG. 16 illustrates an embodiment of an environmental MNPEF system, illustrated by way of example and not limitation, incorporated into furniture such as a couch. FIG. 16 illustrates a top view of the couch. The system includes a power source or sources 1614 to provide electrical power for the electric field system and possibly provide power for the magnetic field system. The magnetic field system may comprise permanent magnets or solenoids 1616 along the sides of the couch, and the electric field system may include electrode(s) 1618 on the back of the couch. The solenoids or magnets 1616 may be oriented to provide magnetic field vectors in the lateral direction, and the electrodes 1618 may be oriented to provide the electric field vectors in a direction from the back of the couch to the front. However, the system may be engineered to provide the fields in other non-parallel vector directions.

Figures 17A, 17B:
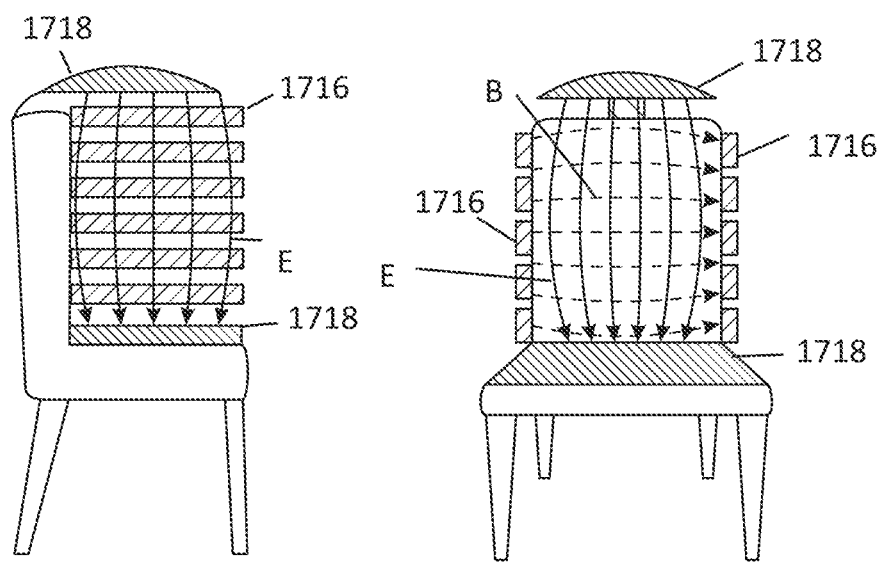
FIGS. 17A-B illustrate an embodiment of an environmental MNPEF system, illustrated by way of example and not limitation, incorporated into furniture such as a chair.

FIGS. 17A-B illustrate an embodiment of an environmental MNPEF system, illustrated by way of example and not limitation, incorporated into furniture such as a chair. The system includes a power source or sources 1714 to provide electrical power for the electric field system and possibly provide power for the magnetic field system. The magnetic field system may comprise permanent magnets or solenoids 1716 along the sides of the backrest of the chair, and the electric field system may include electrode(s) 1718 on the seat of the chair. Some embodiments may further provide electrode(s) over the chair extending off of the backrest. The solenoids or magnets 1716 may be oriented to provide magnetic field vectors in the lateral direction, and the electrodes 1718 may be oriented to provide the electric field vectors in a direction from the top of the chair to the seat. However, the system may be engineered to provide the fields in other non-parallel vector directions.

A system may include a machine in the example form of a computer system, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by one or more processors (e.g., a computer) to individually or jointly execute instructions to perform any one or more of the methodologies discussed herein.

An example of a computer system may include components such as at least one processor (e.g., a central processing unit (CPU), a graphics processing unit (GPU) or both, processor cores, compute nodes, etc.), a main memory and a static memory, which communicate with each other via a link (e.g., bus). Components of a computer system may include a video display unit, an alphanumeric input device (e.g., a keyboard), and a user interface (UI) navigation device (e.g., a mouse). The video display unit, input device and UI navigation device may be incorporated into a touch screen display. Components of a computer system may include a storage device (e.g., a drive unit), a signal generation device (e.g., a speaker), a network interface device, and one or more sensors. It will be understood that other forms of machines or apparatuses (such as IPG, RC, CP devices, and the like) that are capable of implementing the methodologies discussed in this disclosure may not incorporate or utilize every one of these components (e.g. may not incorporate a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media. The term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM) and flash memory devices; magnetic disks such as internal hard disks and removable disks; magneto-optical disks; and CD-ROM and DVD-ROM disks.

The instructions may further be transmitted or received over a communications network using a transmission medium via the network interface device utilizing any one of a number of well-known transfer protocols (e.g., HTTP or Bluetooth®). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

Applications for Magnetic Fields and Non-Orthogonal Electric Fields

As described herein, magnetic and electric fields may be applied (delivered) to an animal, e.g., a vertebrate such as mammal, e.g., a human, to deliver a therapeutic amount of energy to the whole body or a specific area of a body of the animal. In one embodiment, the energy delivered alters ROS and/or RNS amounts or levels in a mammal, e.g., increases the level or amount of ROS and/or RNS in a mammal having a chronic disease such as cancer, diabetes, obesity, or glaucoma, or having neurological disorder or an immune related disorders. In one embodiment, the energy delivered alters ROS and/or RNS amounts or levels in a mammal so as to reduce symptoms of aging. In one embodiment, the energy is delivered to white fat, brown fat, the gall bladder, the stomach, the large intestine, the small intestine, the kidney, the heart, the spleen, the appendix (e.g., for appendicitis based inflammation), the retina or optic nerve (e.g., to treat glaucoma or retinal disease), the brain (e.g., to inhibit or treat neurodegenerative disease or cancer), the bladder, the pancreas, the spleen, the breast, the prostate, or the lung, or any combination thereof of a mammal.

In one embodiment, the energy is delivered to one or more specific regions of the body of a mammal. In one embodiment, the energy is delivered to the entire body of a mammal. In one embodiment, the energy is exogenously delivered. In one embodiment, the energy is delivered via an implantable device. In one embodiment, the energy is delivered via a device which is in contact with the skin of a mammal.

In one embodiment, the strength of magnetic field is from 0 to 0.1 mT. In one embodiment, the strength of magnetic field is from 0.1 mT to 1 mT. In one embodiment, the strength of magnetic field is from 1 to 10 mT. In one embodiment, the strength of magnetic field is from 10 to 100 mT.

In one embodiment, the strength of the externally applied electric field is 0 to 100 V/m. In one embodiment, the strength of the externally applied electric field is 100 to 1000 V/m. In one embodiment, the strength of the externally applied electric field is 1 to 10 kV/m. In one embodiment, the strength of the externally applied electric field is 10 to 100 kV/m. In one embodiment, the strength of the externally applied electric field is 100 to 1000 kV/m. In one embodiment, to inhibit or treat diabetes, the strength of the externally applied electric field is 2 to 30 kV/m. In one embodiment, to inhibit or treat cancer, the strength of the externally applied electric field is 2 to 60 kV/m.

In one embodiment, the frequency of AC magnetic and electric fields (sine or square wave forms) is 0 to 100 Hz. In one embodiment, the frequency of AC magnetic and electric fields is 10 to 100 Hz. In one embodiment, the frequency of AC magnetic and electric fields is 100 to 1000 Hz. In one embodiment, the frequency of AC magnetic and electric fields is 1 to 10 kHz. In one embodiment, the frequency of AC magnetic and electric fields is 10 to 100 kHz. In one embodiment, the frequency of AC magnetic and electric fields is 100 to 1000 kHz.

In one embodiment, the mammal has diabetes or is at risk of developing diabetes (has pre-diabetes). In one embodiment, the energy delivered increases insulin sensitivity, increases insulin secretion, or reduces glucose excretion, e.g., from the kidney, in the mammal. In one embodiment, the energy delivered has an anti-hyperglycemic effect.

In one embodiment, the energy delivered improves cardiovascular outcomes, reduces mild cognitive impairment, reduces dementia, and/or reduces inflammation, e.g., associated with a disease or an infection with a microbe such as a bacteria or virus.

In one embodiment, the energy delivered decreases or inhibits one or more symptoms of neurological diseases including but not limited to Parkinson's disease, Alzheimer's disease or amyotrophic lateral sclerosis (ALS).

In one embodiment, the mammal has diabetes or is at risk of developing diabetes (has pre-diabetes). In one embodiment, the energy delivered increases insulin sensitivity or increases insulin secretion in the mammal. In one embodiment, the energy delivered increases pancreatic beta-cell density. In one embodiment, the energy modulates glucose regulation in the mammal. In one embodiment, the energy improves glycemia or insulin response in the mammal. In one embodiment, the energy delivered improves glucose tolerance in the mammal. In one embodiment, the energy delivered decreases glucose production in the mammal.

In one embodiment, the mammal has cancer. According to various embodiments, the energy delivered to the mammal reduces tumor size or inhibits tumor growth and/or the energy delivered to the mammal improves overall survival. Thus, according to these various embodiments, the energy delivered to the mammal that has cancer may improve overall survival with or without reducing tumor size/inhibiting tumor growth; and the energy may reduce tumor size/inhibit tumor growth with or without improving overall survival.

In one embodiment, a method of preventing, inhibiting or treating one or more symptoms in a mammal of a disease associated with aberrant reactive oxygen species levels is provided. The method includes exogenously applying to one or more organs or tissues of the mammal, an effective amount of a magnetic field in a first direction, wherein the magnetic field is provided by a system that includes at least one magnetic field source that includes at least one permanent magnet, a temporary magnet or electric current flow through a conductor to produce the magnetic field, and an electric field in a second direction, wherein the system includes at least one electric field source to provide the electric field and the second direction is non-parallel to the first direction. In one embodiment, the mammal is a human. In one embodiment, the first and second directions are separated by angle within a range of 30 degrees to 150 degrees. In one embodiment, the first and second directions are separated by angle within a range of 60 degrees to 120 degrees. In one embodiment, the magnetic field and the electric field are applied concurrently. In one embodiment, the magnetic field and the electric field are applied sequentially. In one embodiment, the magnetic field has a strength that is less than 100 mT. In one embodiment, the magnetic field has a strength that is within a range of 1 to 10 mT. In one embodiment, the electric field has a strength that is less than 1000 V/m. In one embodiment, the electric field has a strength within a range of 0.1 to 100 kV/m. In one embodiment, the electric field has a strength that is less than 1000 mV/m. In one embodiment, the electric field has a strength that is less than 1 mV/m. In one embodiment, the magnetic field has a frequency less than 1,000 kHz. In one embodiment, the magnetic field has a frequency within a range between 100 Hz and 10 kHz. In one embodiment, the energy is applied for 1 to 4 hours, 4 to 10 hours, 1 to 10 hours, 2 to 12 hours or 1 to 24 hours or over 1 second.

In one embodiment, a method of inhibiting or treating cancer in a mammal is provided. The method includes exogenously applying to one or more affected organs or tissues of the mammal, an effective amount of a magnetic field in a first direction, wherein the magnetic field is provided by a system that includes at least one magnetic field source that includes at least one permanent magnet, a temporary magnet or electric current flow through a conductor to produce the magnetic field, and an electric field in a second direction, wherein the system includes at least one electric field source to provide the electric field and the second direction is non-parallel to the first direction. In one embodiment, the mammal is a human. In one embodiment, the first and second directions are separated by angle within a range of 10 degrees to 170 degrees or within a range of 5 to 175 degrees. In one embodiment, the first and second directions are separated by angle within a range of 60 degrees to 120 degrees. In one embodiment, the magnetic field and the electric field are applied concurrently. In one embodiment, the magnetic field and the electric field are applied sequentially. In one embodiment, the magnetic field has a strength that is less than 100 mT. In one embodiment, the magnetic field has a strength that is within a range of 1 to 10 mT. In one embodiment, the electric field has a strength that is less than 1000 V/m. In one embodiment, the electric field has a strength within a range of 0.1 to 100 kV/m. In one embodiment, the electric field has a strength that is less than 1000 mV/m. In one embodiment, the electric field has a strength that is less than 1 mV/m. In one embodiment, the magnetic field has a frequency less than 1,000 kHz. In one embodiment, the magnetic field has a frequency within a range between 100 Hz and 10 kHz. In one embodiment, the energy is applied for 1 to 4 hours, 4 to 10 hours, 1 to 10 hours, 2 to 12 hours or 1 to 24 hours. In one embodiment, the energy is applied for 1 to 4 hours, 4 to 10 hours, 1 to 10 hours, 2 to 12 hours or 1 to 24 hours per day. In one embodiment, the method is employed after tumor resection, chemotherapy, biologic therapy, or radiation therapy. It is anticipated that MNPEFs will be effective for cancer with immunotherapy.

In one embodiment, a method of inhibiting or treating diabetes in a mammal is provided. The method includes exogenously applying to the abdomen of the mammal, an effective amount of a magnetic field in a first direction, wherein the magnetic field is provided by a system that includes at least one magnetic field source that includes at least one permanent magnet, a temporary magnet or electric current flow through a conductor to produce the magnetic field, and an electric field in a second direction, wherein the system includes at least one electric field source to provide the electric field and the second direction is non-parallel to the first direction. In one embodiment, the mammal is a human. In one embodiment, the first and second directions are separated by angle within a range of 10 degrees to 170 degrees or within a range of 5 to 175 degree. In one embodiment, the first and second directions are separated by angle within a range of 60 degrees to 120 degrees. In one embodiment, the magnetic field and the electric field are applied concurrently. In one embodiment, the magnetic field and the electric field are applied sequentially. In one embodiment, the magnetic field has a strength that is less than 100 mT. In one embodiment, the magnetic field has a strength that is within a range of 1 to 10 mT. In one embodiment, the electric field has a strength that is less than 1000 V/m. In one embodiment, the electric field has a strength within a range of 0.1 to 100 kV/m. In one embodiment, the electric field has a strength that is less than 1000 mV/m. In one embodiment, the electric field has a strength that is less than 1 mV/m. In one embodiment, the magnetic field has a frequency less than 1,000 kHz. In one embodiment, the magnetic field has a frequency within a range between 100 Hz and 10 kHz. In one embodiment, the energy is applied for 1 to 4 hours, 4 to 10 hours, 1 to 10 hours, 2 to 12 hours or 1 to 24 hours. In one embodiment, the energy is applied for 1 to 4 hours, 4 to 10 hours, 1 to 10 hours, 2 to 12 hours or 1 to 24 hours per day.

In one embodiment, a method of preventing, inhibiting or treating one or more symptoms in a mammal of a disease associated with aberrant reactive oxygen species levels is provided. The method includes applying to one or more organs or tissues of the mammal, via an implantable device an effective amount of a magnetic field in a first direction, wherein the magnetic field is provided by a system that includes at least one magnetic field source that includes at least one permanent magnet, a temporary magnet or electric current flow through a conductor to produce the magnetic field, and an electric field in a second direction, wherein the system includes at least one electric field source to provide the electric field and the second direction is non-parallel to the first direction. In one embodiment, the mammal is a human. In one embodiment, the first and second directions are separated by angle within a range of 30 degrees to 150 degrees. In one embodiment, the first and second directions are separated by angle within a range of 60 degrees to 120 degrees. In one embodiment, the magnetic field and the electric field are applied concurrently. In one embodiment, the magnetic field and the electric field are applied sequentially. In one embodiment, the magnetic field has a strength that is less than 100 mT. In one embodiment, the magnetic field has a strength that is within a range of 1 to 10 mT. In one embodiment, the electric field has a strength that is less than 1000 V/m. In one embodiment, the electric field has a strength within a range of 0.1 to 100 kV/m. In one embodiment, the electric field has a strength that is less than 1000 mV/m. In one embodiment, the electric field has a strength that is less than 1 mV/m. In one embodiment, the magnetic field has a frequency less than 1,000 kHz. In one embodiment, the magnetic field has a frequency within a range between 100 Hz and 10 kHz.

Experiment Results

The MNPEF therapy may be used treat diabetes. In an embodiment, the system comprises: a magnetic field system, such as a direct current (DC) magnetic field system that generates and applies a DC magnetic field to a patient; and an electric field system, such as a DC electric field system that generates and applies a DC electric field to the patient in a field direction non-parallel to a direction of the DC magnetic field. Delivery of the magnetic field and delivery of the electric field may cause the following changes in clinical parameters: reduced hemoglobin A1c (HbA1c), the key clinical marker used to diagnose diabetes and monitor therapy; increased glucose tolerance in the patient; and/or increased insulin sensitivity in the patient. The direction of the applied electric field and the direction of the applied magnetic field in the tissue may be non-parallel to each other.

To study the therapeutic potential of MOEFs in T1D and T2D, two widely used mouse models that are recommended by the FDA for the evaluation of potential diabetes therapies were employed (Guidance for industry. Diabetes mellitus: developing drugs and therapeutic biologics for treatment and prevention. (ed. U.S. Department of Health and Human Services, F.D.A., Center for Drug Evaluation and Research) (2008)).

Type 1 diabetes (T1D) was induced in wild-type (WT) mice by injecting low-dose streptozotocin (STZ) for 5 days as previously described (Furman, B. L. Streptozotocin-Induced Diabetic Models in Mice and Rats. *Current protocols in pharmacology* 70, 5.47.41-20 (2015); King, A. J. F. The use of animal models in diabetes research. *British journal of pharmacology* 166, 877-894 (2012); Qinna, N. A. & Badwan, A. A. Impact of streptozotocin on altering normal glucose homeostasis during insulin testing in diabetic rats compared to normoglycemic rats. *Drug Design, Development and Therapy* 9, 2515-2525 (2015)). STZ is a glucosamine-nitrosourea compound derived from Streptomyces achromogenes that is used clinically as a chemotherapeutic agent in the treatment of pancreatic β cell carcinoma. STZ selectively destroys pancreatic β-cells, (resulting in hypoinsulinemia and hyperglycemia), mimicking the pathophysiology in T1D patients. MOEF$^{DC/DC}$ treatment began 4 weeks after STZ induction when mice reached a fasting blood glucose >200 mg/dL.

Type 2 diabetes (T2D) was studied using the mouse model db/db, which lacks the leptin receptor and develops obesity, insulin resistance and type 2 diabetes and the high fat diet mouse model, fed a 60% fat diet to induce obesity, insulin resistance and type 2 diabetes (Kobayashi, K., et al. The db/db mouse, a model for diabetic dyslipidemia: molecular characterization and effects of Western diet feeding. *Metabolism: clinical and experimental* 49, 22-31 (2000)). Animals were treated after they reached 8 weeks of age.

Postprandial glucose regulation was monitored using Glucose tolerance tests (GTT) and the physiological action of insulin was monitored using Insulin tolerance tests (ITT). Pyruvate tolerance tests (PTT) were used to evaluate hepatic gluconeogenesis.

The GTT tests were performed by giving a 2 mg/kg of body weight bolus of glucose intraperitoneally to mice that had been fasting for 16 hours.

Similarly, insulin tolerance and pyruvate tolerance (PTT) were tested by giving a 0.5 U/kg of body weight bolus of insulin (ITT; Humalin®, Eli Lilly) or 1.0 g/kg pyruvate (Sigma) intraperitoneally following a 5-hour fast.

Metabolic changes were monitored using the following assays. Blood glucose levels were measured using a Freestyle Lite® glucometer (Abbot). Insulin and Hemoglobin A1c were measured using an ELISA kit and A1c Now (PTS Diagnostics). Homeostasis model assessment of insulin resistance (HOMA-IR) was calculated as follows: fasting insulin (microU/L)×fasting blood glucose (nmol/L)/22.5. (Muniyappa, R., et al. Comparison between surrogate indexes of insulin sensitivity/resistance and hyperinsulinemic euglycemic clamp estimates in rats. *American Journal of Physiology—Endocrinology And Metabolism* 297, E1023 (2009)).

Immunofluorescence and western blotting was performed as previously described (Carter, C. S., et al. Abnormal development of NG2+PDGFR–[alpha]+ neural progenitor cells leads to neonatal hydrocephalus in a ciliopathy mouse model. *Nat Med* 18, 1797-1804 (2012)). Mitochondrial complex activity was assayed as previously described (Birch-Machin, M. A., Briggs, H. L., Saborido, A. A., Bindoff, L. A. & Turnbull, D. M. An evaluation of the measurement of the activities of complexes I-IV in the respiratory chain of human skeletal muscle mitochondria. *Biochemical medicine and metabolic biology* 51, 35-42 (1994)). The following antibodies were used: Cell Signal Technologies, phospho-AMPK (2531), total AMPK (2532), phospho-ACC (11818), total ACC (3676), phospho-P38 (4511), total P38 (8690), VDAC (4661), hsp70 (Proteintech, 10995-1-AP), hspa2 (Proteintech, 12797-1-AP), GAPDH (Thermo Fisher) and total OXPHOS rodent WB antibody cocktail (ab110413).

FIGS. 32A-32E show field line plots of exemplary MNPEF$^{DC/DC}$ and prototypes that generate these fields to produce anti-hyperglycemic effects. Anti-hyperglycemic effects were found in both male and female mice following exposure to a 3 mT direct current (DC) magnetic field, and a 1 kV/meter (kV/m) electrostatic field emanating in a non-parallel direction relative to the direction of the DC magnetic field (i.e., MOEF$^{DC/DC}$, FIGS. 32A-32E). Interestingly, treating animals with an alternating current (AC)

magnetic field, 3 mT combined with a 1 kV/m non-parallel electrostatic field, yielded anti-hyperglycemic effects in males but not females. Stronger effects using higher intensity magnetic fields (>3 mT) and electric fields(>1 kV/m) are expected. The length of therapy application may alter treatment efficacy. For example, application of therapy for 6 hours a day for a two-week period provides beneficial results, while shorter or fewer therapy sessions may likely result in less treatment efficacy. Longer or shorter (and/or fewer or greater) treatment sessions may of course be contemplated within the scope of this disclosure.

Figure 32A:
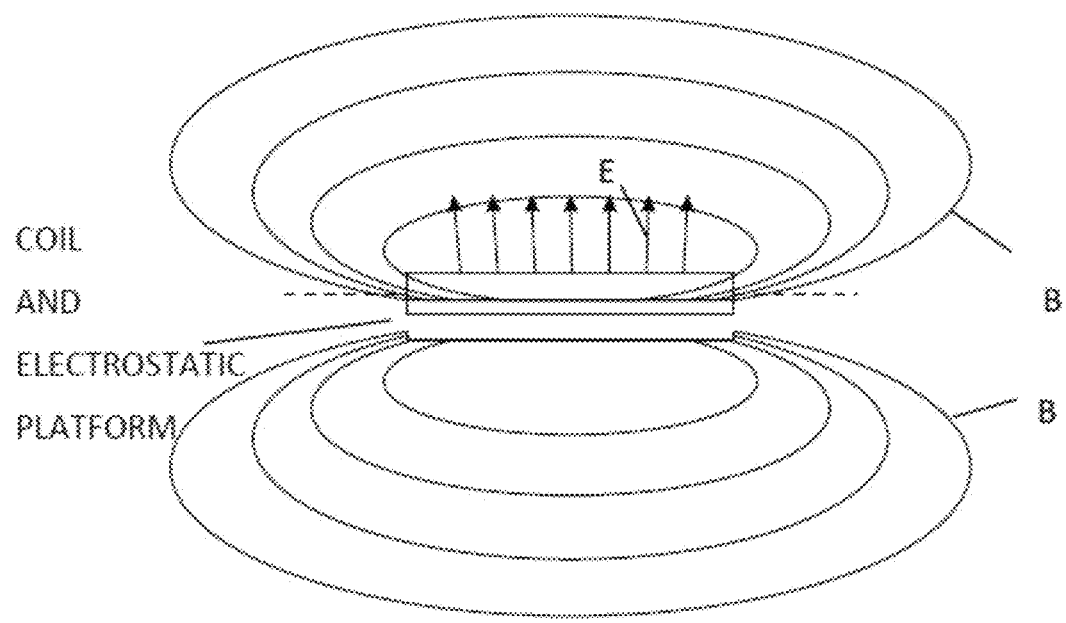
FIGS. 32A-32E show field line plots of exemplary MNPEF$^{DC/DC}$ and prototypes that generate these fields to produce anti-hyperglycemic effects.
Figure 32B:
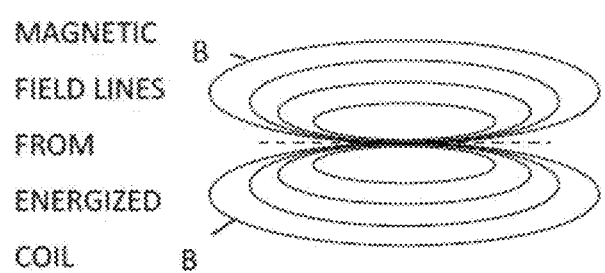
Figure 32C:
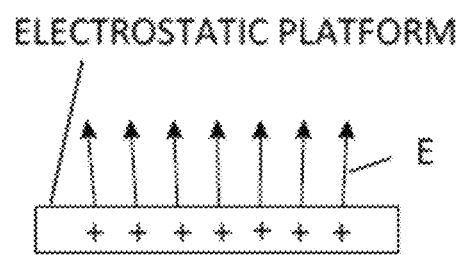
Figure 32D:
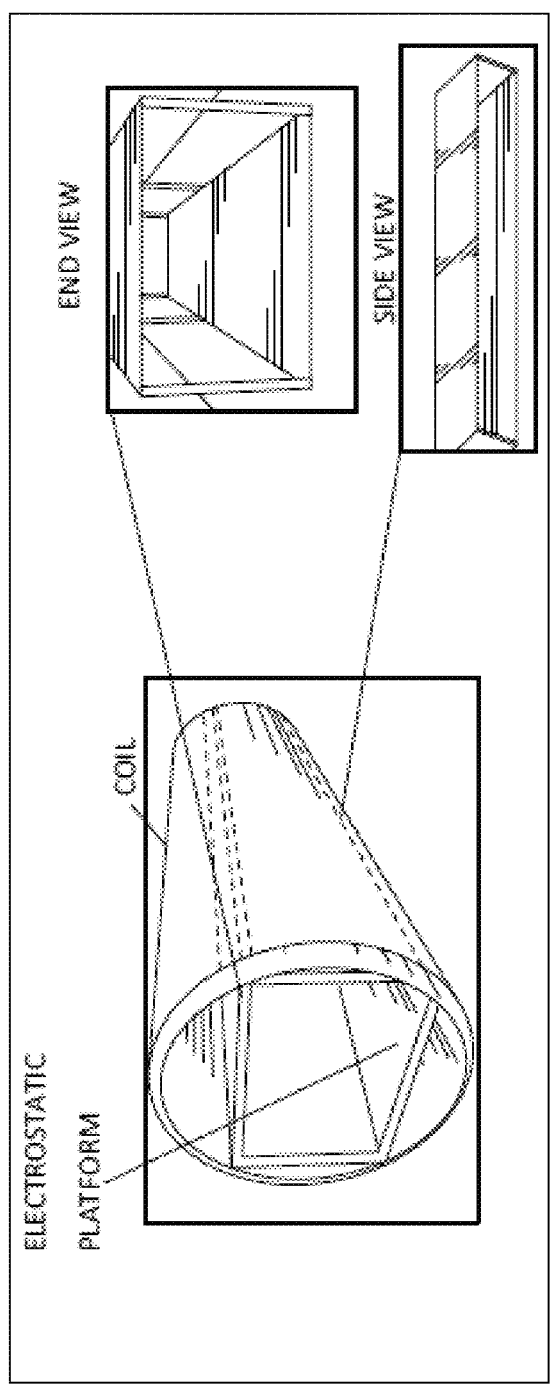
Figure 32E:
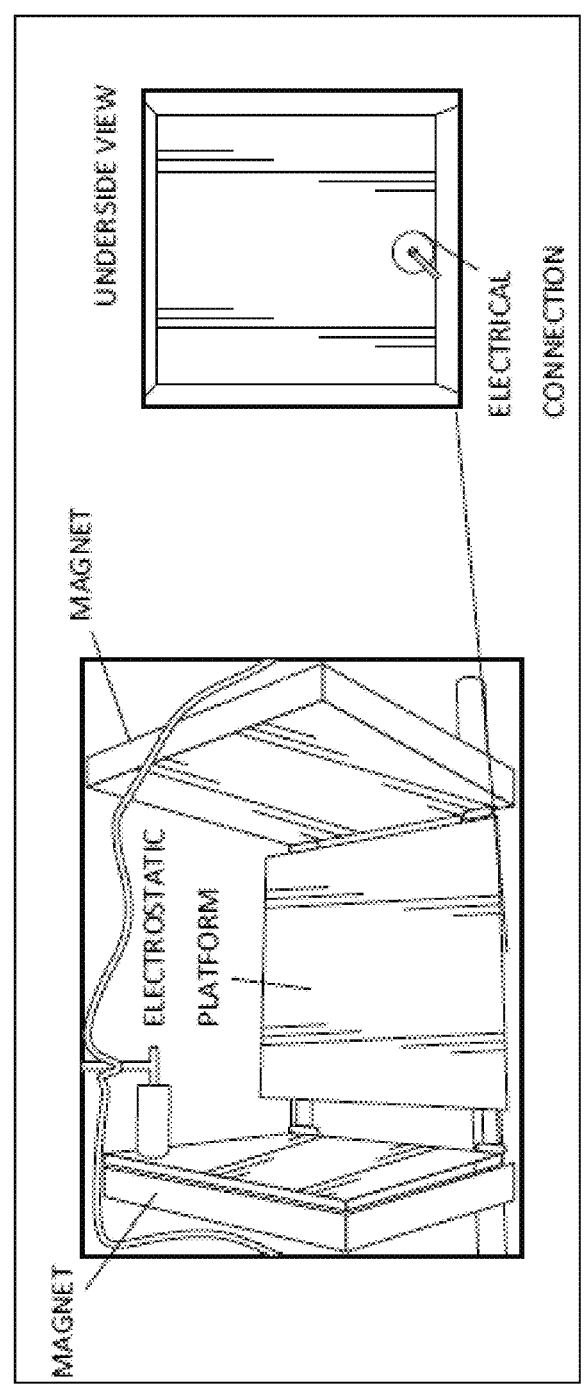

FIG. 32A depicts the magnetic and substantially orthogonal electric fields that underlie the anti-hyperglycemic effects observed. The inventors use DC magnetic fields with an intensity of 3 mT and a 1 kV/m electric field substantially orthogonal relative to the magnetic field. FIG. 32B shows a coil that emits a DC magnetic field that runs through the center of the hollow cylinder. In addition, an electrostatic field is generated in the substantially orthogonal direction relative to the magnetic field lines using an electrostatic platform positioned inside the coil (orange dotted lines in FIG. 32B). The end and side views of the electrostatic platform are shown outside of the coil in FIG. 32C. FIG. 32D shows a miniaturized prototype that emits static magnetic (blue lines in FIG. 32A) and substantially orthogonal electrostatic fields relative to the magnetic field (red lines in FIG. 32A). Permanent magnets arranged on each side of the miniaturized prototype generate a magnetic field with intensities of up to 5 mT (FIG. 32D). The electrostatic field is generated by an electrostatic platform that generates the electrostatic field in the miniaturized prototype (FIGS. 32D and 32E). The electrostatic platforms labeled in FIGS. 32B and 32D use a high voltage power supply to generate electrostatic fields.

Figure 18:
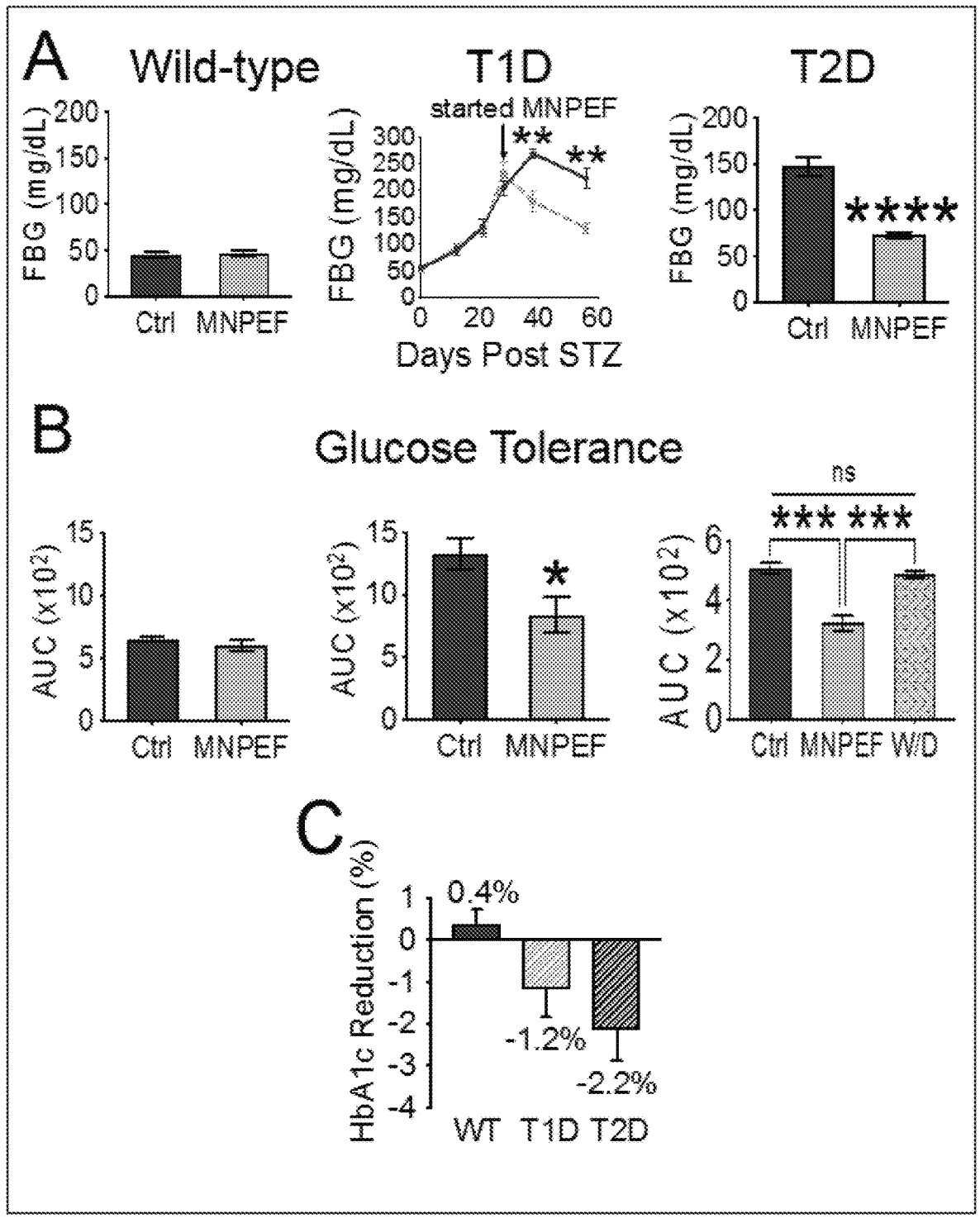
FIG. 18 illustrates experimental data suggesting that MNPEFs (DC/DC) improve glycemia in animal models of type 1 diabetes (T1D) and type 2 diabetes (T2D).

FIG. 18 illustrates experimental data suggesting that MNPEFs (DC/DC) improve glycemia in animal models of type 1 diabetes (T1D) and type 2 diabetes (T2D). To study the glycemic effects of MOEFs, the inventors employed the db/db mouse, an obese-diabetic model of type 2 diabetes, and the streptozotocin non-obese type 1 diabetic model. Both animal models are recommended by the FDA to evaluate the efficacy of therapies for diabetes. Following 2 weeks of MOEF$^{DC/DC}$ treatment, significant improvements in fasting blood glucose (FBG) and glucose tolerance were observed, Data in section A indicates fasting blood glucose (FBG) for wild-type (WT) mice, type 1 diabetic (T1D) mice, type 2 diabetic (T2D) mice. Data in section B indicates glucose tolerance for WT, T1D, and T2D mice, and suggests that MNPEFs improve glucose tolerance in T1D and T2D mice. Additionally when MNPEF therapy is removed (W/D) glucose response rebounds. Data in section C indicates hemoglobin A1c (HbA1c) which is a long-term marker of glucose management is reduced T1D and T2D mice after treatment. No overt changes are seen in WT mice.

Figure 19:
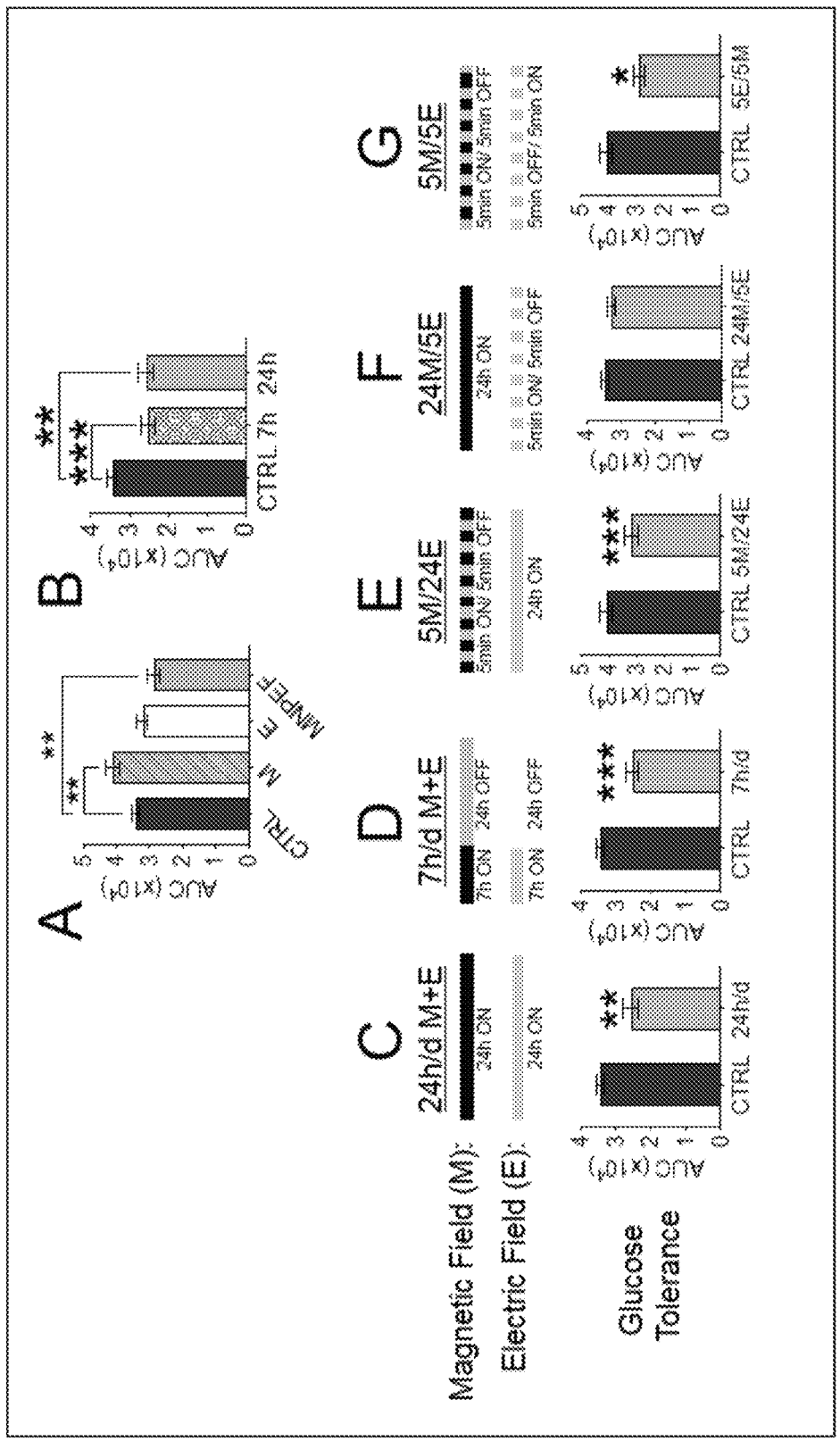
FIG. 19 illustrates experimental data to identify effects of different combinations of MNPEFs (DC/DC) on glucose tolerance in T2D mice.

FIG. 19 illustrates experimental data to identify effects of different combinations of MNPEFs (DC/DC) on glucose tolerance in T2D mice. Section A includes data results when T2D mice were treated with a single magnetic (M), a single electric (E), or combined M and E fields (MNPEF) and assessed for glucose tolerance. Only the MNPEF group show an improvement of glucose tolerance compared to untreated (CTRL) T2D mice. Magnetic field (M) and electric field (E) alone do no improve glucose tolerance. Section B includes data results suggesting that MNPEFs administered for 7 h/d are as effective at improving glycemia as continuous 24 h treatment. Sections C-G include data results when combinations of M and E fields were used to treat T2D mice and their glucose tolerance. Different parameters tested include: 24 h/d E+M (electric & magnetic fields on 24 h per day), 7 h/d E+M (E & M fields on 7 h per day and off 17 h per day), 24E/5M (E field on 24 h/d, M field pulsed 5 min on/5 min off), 5E/24M (E field pulsed 5 min on/5 min off, M field on 24 h/d), and 5E/5M (E field on 5 min [M off], then M field on 5 min [E off], repeat 24 h/d). The 24 h/d E+M, 7 h/d E+M, 24E/5M, and 5E/5M all show efficacy in improving glucose tolerance. However the 5E/24M did not show improvements in glucose tolerance. Tolerance is presented as AUC ("area under the curve").

Figure 20:
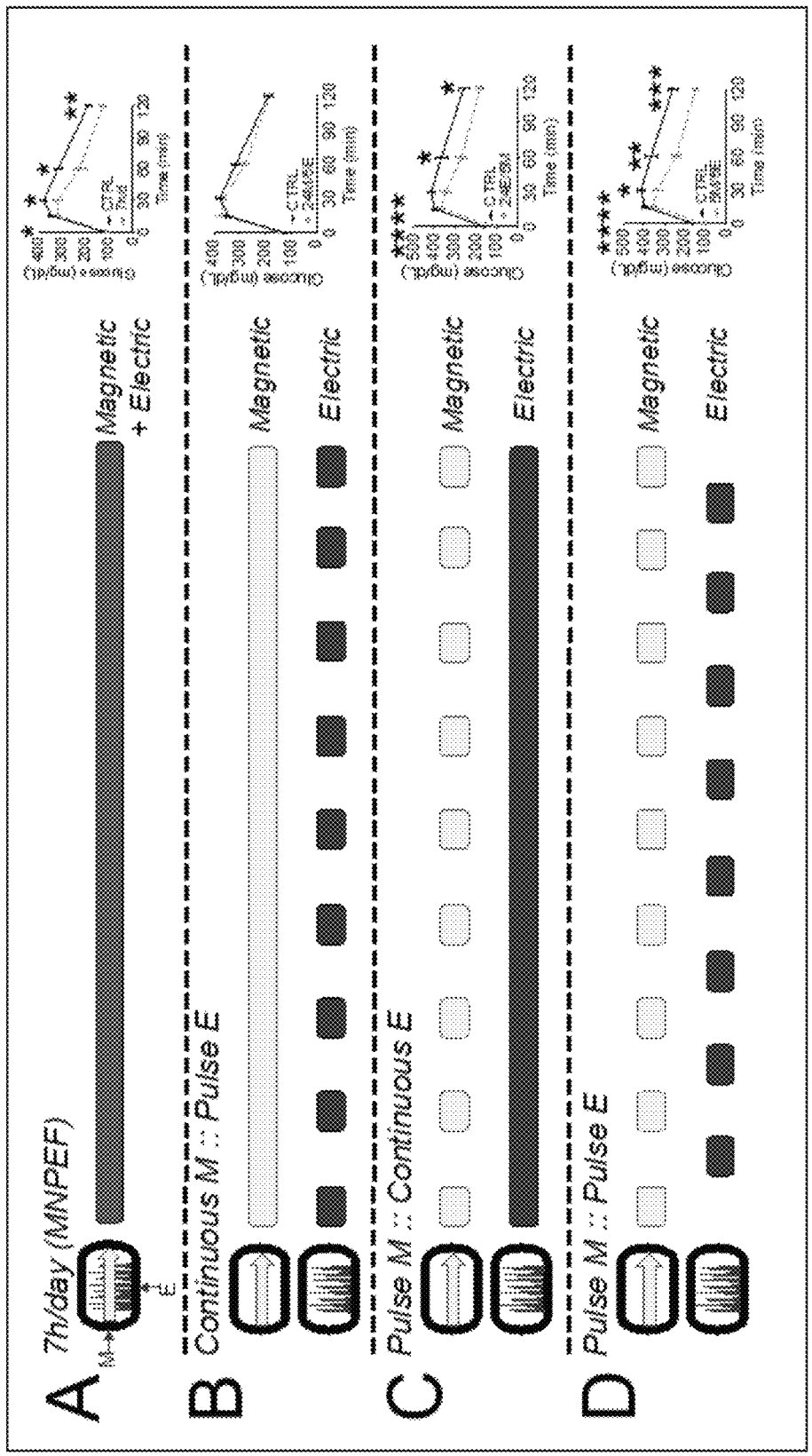
FIG. 20 illustrates experimental data for glucose tolerance presented as blood glucose over time for T2D mice using different combinations of MNPEFs (DC/DC).

FIG. 20 illustrates experimental data for glucose tolerance presented as blood glucose over time for T2D mice using different combinations of MNPEFs (DC/DC). Data in Section A suggests that 7 h/d MNPEF (E & M fields on 7 h per day and off 17 h per day) improves glucose tolerance. Data in Section B suggests that continuous M::Pulse E (M field on 24 h/d, E field pulsed 5 min on/5 min off) does not improve glucose tolerance. Data in Section C suggests that Pulse M::Continuous E (M field pulsed 5 min on/5 min off, E field on 24 h/d) improves glucose tolerance. Data in Section D suggests that Pulse M::Pulse E (E field on 5 min [M off], then M field on 5 min [E off], repeat 24 h/d) improves glucose tolerance.

Figure 21:
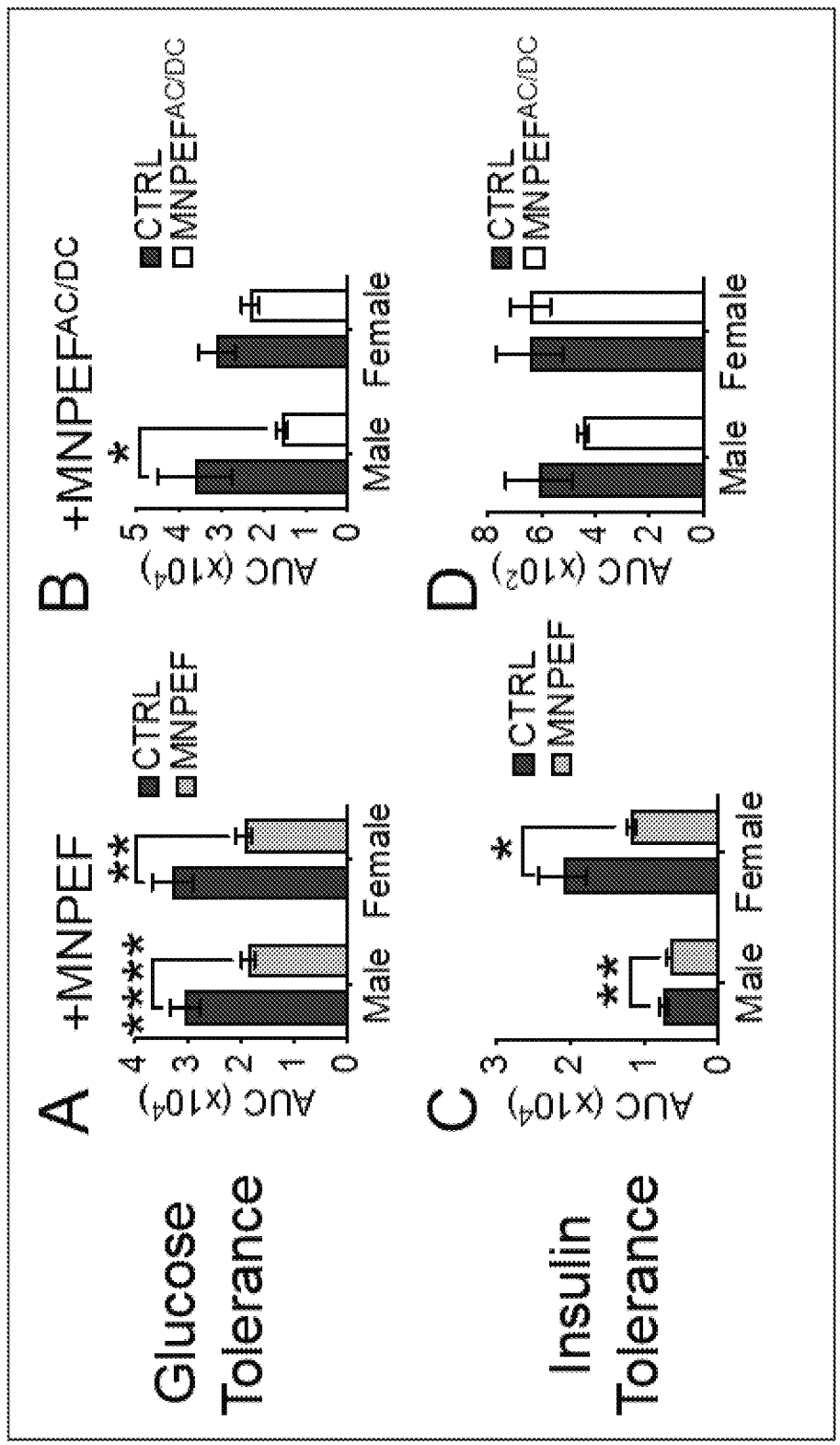
FIG. 21 illustrates experimental data suggesting that AC MNPEFs (AC/DC) improve diabetes in T2D male but not female mice.

FIG. 21 illustrates experimental data suggesting that AC MNPEFs (AC/DC) improve diabetes in T2D male but not female mice. Sections A and C refer to experiments where mice were treated with MNPEF (DC/DC), and Sections B and D refer to experiments where mice were treated with MNPEF (AC/DC). Data in Section A suggests that glucose tolerance improves in male and female T2D mice after MNPEF (DC/DC) treatment. Data in Section B suggests that glucose tolerance improves only in male T2D mice after AC MNPEF (AC/DC) treatment. Data in Section C suggests that insulin tolerance improves in male and female T2D mice after MNPEF (DC/DC) treatment. Data in Section D suggests that insulin tolerance only improves in male T2D mice after AC MNPEF (AC/DC) treatment. This data suggests gender-specific effects of MNPEFs, as MNPEF (DC/DC) effectively treated both males and females, and MNPEF (AC/DC) effectively treated males but did not effectively treat females.

Figure 22:
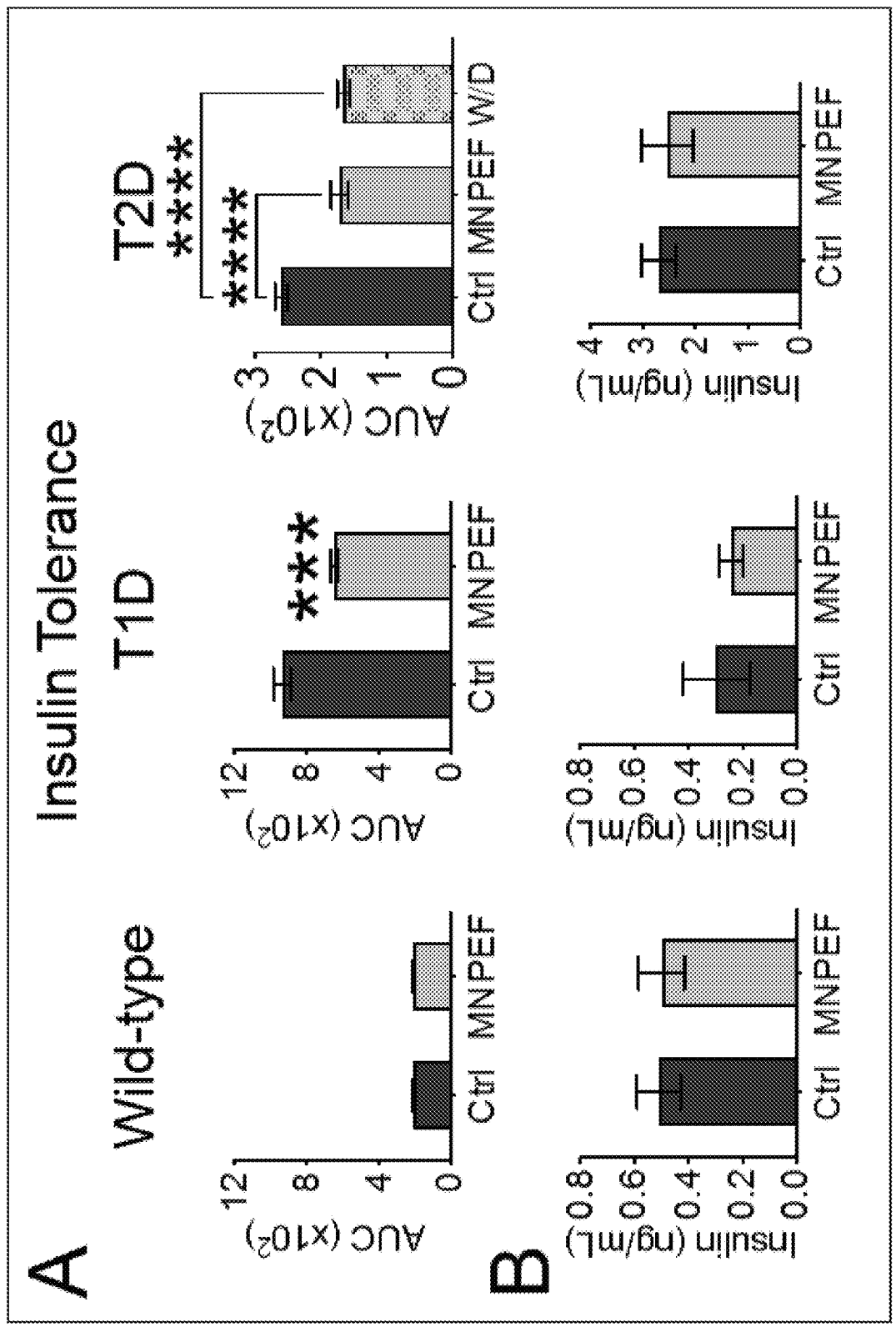
FIG. 22 illustrates experimental data suggesting that MNPEFs improve the body's response to insulin.

FIG. 22 illustrates experimental data suggesting that MNPEFs improve the body's response to insulin. The data suggests that insulin tolerance is improved in T1D and T2D mice while and fasting insulin levels stay the same. Data in Section A suggests that insulin tolerance improved in T1D and T2D mice but not wild-type mice. Moreover, the improved insulin tolerance is long-lasting in T2D mice even after withdrawing treatment (W/D). Data in section B suggests that plasma insulin levels are not changed.

Figure 23:
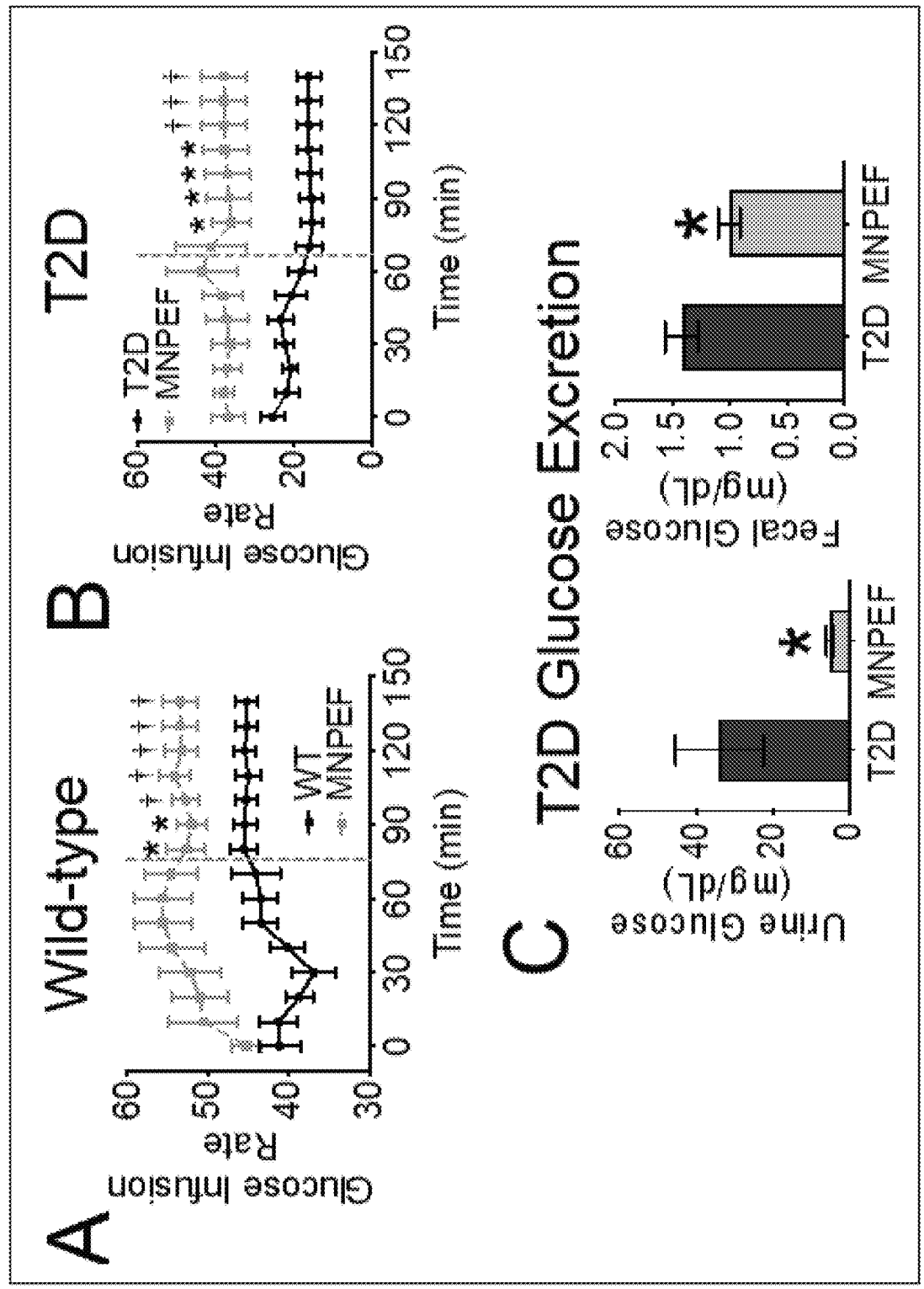
FIG. 23 illustrates experimental data suggesting that MNPEFs improve insulin sensitivity in wild-type and T2D mice.

FIG. 23 illustrates experimental data suggesting that MNPEFs improve insulin sensitivity in wild-type and T2D mice. Euglycemic-hyperinsulinemic clamps are the gold standard assay for assessing the body's response to insulin. These clamps were employed to test insulin sensitivity in mice administered MNPEF. Data was collected to show the amount of glucose that can be infused into mice while maintaining the same blood glucose level (minutes 80-150). Increased insulin sensitivity is correlated with an increased infusion rate of exogenous glucose. Data in Section A suggests that MNPEF treatment improves wild-type mouse insulin sensitivity by 25%. Data in section B suggests that MNPEF treatment improves T2D mouse insulin sensitivity by 50%. Data in section C suggests that the improvement in insulin sensitivity and glycemia in T2D mice is not due to increased excretion of glucose, as glucose levels in urine and feces reflect an improved (lower) blood glucose.

Figure 24:
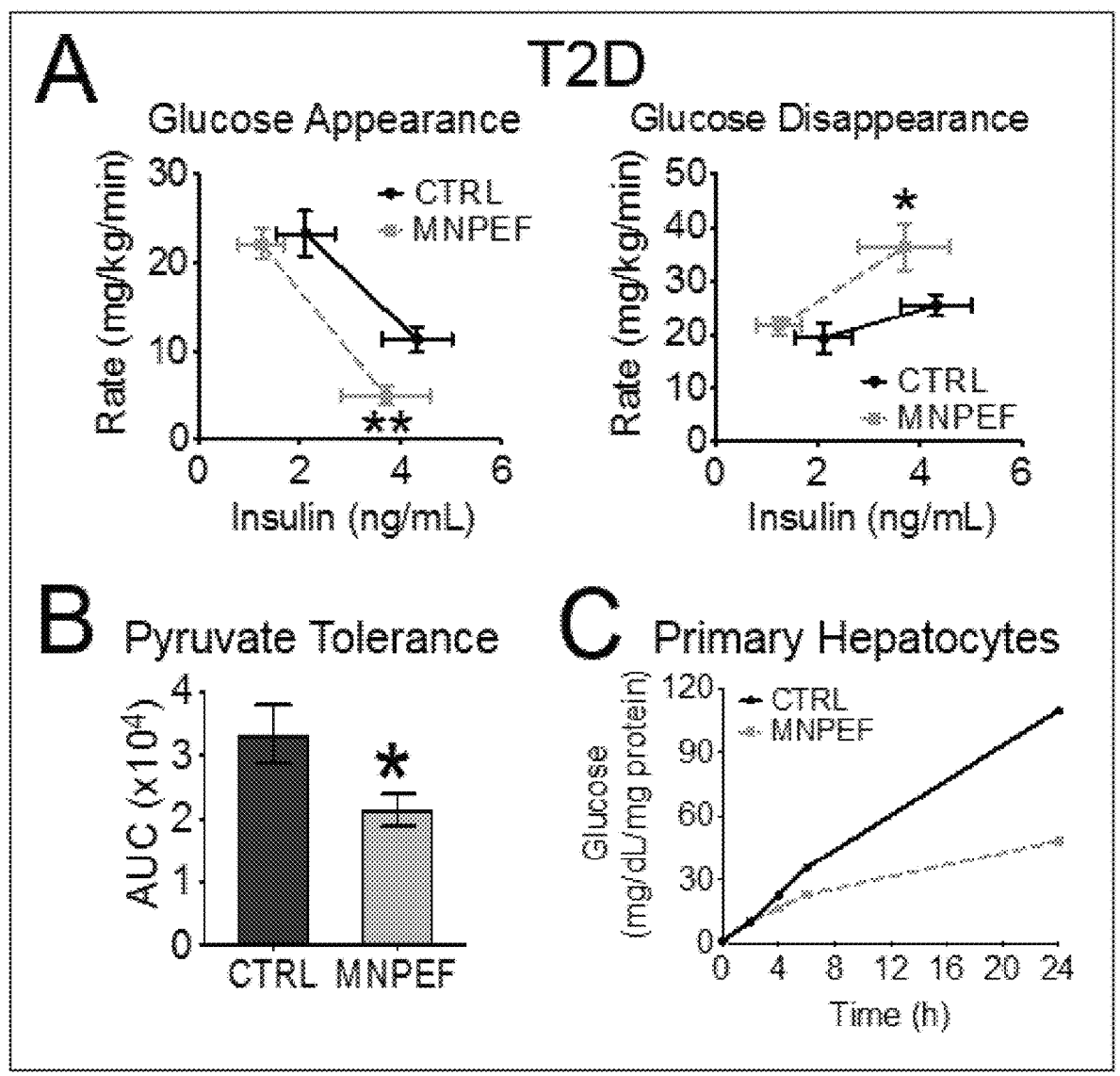
FIG. 24 illustrates experimental data suggesting that MNPEFs improves diabetes by reducing glucose production by the liver.

FIG. 24 illustrates experimental data suggesting that MNPEFs improves diabetes by reducing glucose production by the liver. Data in Section A suggests that MNPEF reduces glucose appearance in the blood, which is indicative of gluconeogenesis and glycogenolysis by the liver, and that MNPEF also increases glucose disappearance from the blood further supporting increased insulin sensitivity in uptake of glucose into tissues. Data in Section B suggests that MNPEF treatment improves pyruvate tolerance, which indicates reduced gluconeogenesis by the liver. Data in Section C suggests that gluconeogenesis by isolated hepatocytes treated with MNPEF is also reduced, suggesting MNPEFs have a direct effect on the liver.

To understand how MNPEFs$^{DC/DC}$ decrease gluconeogenesis, the inventors investigated mitochondria. Mitochondria are primarily involved in generating energy molecules (i.e. adenosine triphosphate, ATP) via a process known as cellular respiration. To generate ATP, mitochondria rely on electron transport through a chain of enzymes collectively called the electron transport chain (ETC). One mechanism by which metformin exerts its therapeutic effects in T2D is by impeding the ETC which inhibits gluconeogenesis, ultimately reducing blood glucose and hemoglobin A1c. Thus, impeding electron transport reduces gluconeogenesis and is known to treat diabetes. Additional mechanisms may underlie the anti-hyperglycemic effects observed.

Figure 25:
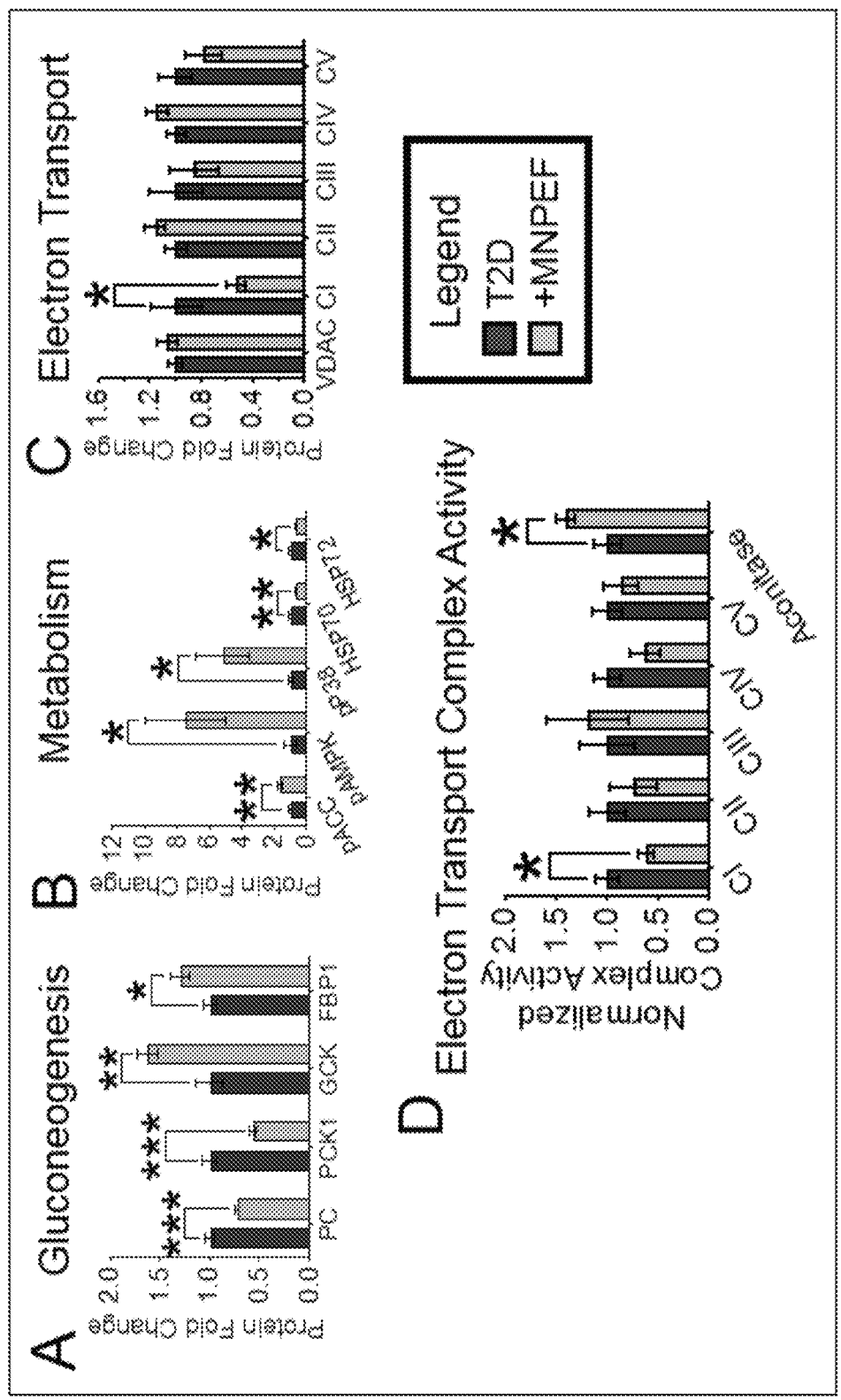
FIG. 25 illustrates experimental data suggesting that MNPEFs regulate metabolism through gluconeogenesis and impeding mitochondrial electron transport.

FIG. 25 illustrates experimental data suggesting that MNPEFs regulate metabolism through gluconeogenesis and impeding mitochondrial electron transport. Data in Section A suggests that MNPEF reduces key regulators of gluconeogenesis (PC and PCK1), which is consistent with reduced glucose production by the liver. Additionally, other enzymes in this pathway (GCK, FBP1) that feed carbons into the pentose phosphate pathway, which is important in regulating the redox state of the cell are increased. Data in Section B suggests that MNPEF increases metabolic proteins important in sensing and generating the energy molecule, adenosine triphosphate (ATP), which is produced through the electron transport chain. Data in Sections C and D suggest that MNPEF specifically reduces protein expression and activity of complex 1 which is the first enzyme in the production of ATP and also a key producer of reactive oxygen species.

Liver is a key organ in regulating glucose in type 2 diabetes (T2D). Reactive oxygen species (ROS) are thought to play a role in regulating glucose metabolism. In order to assess ROS in the diabetic liver, livers were collected from MNPEF treated and untreated T2D mice. Thin liver slices were assessed for ROS by staining liver slices with dihydroethidium (DHE), a dye that binds ROS and turns red.

Figure 26:
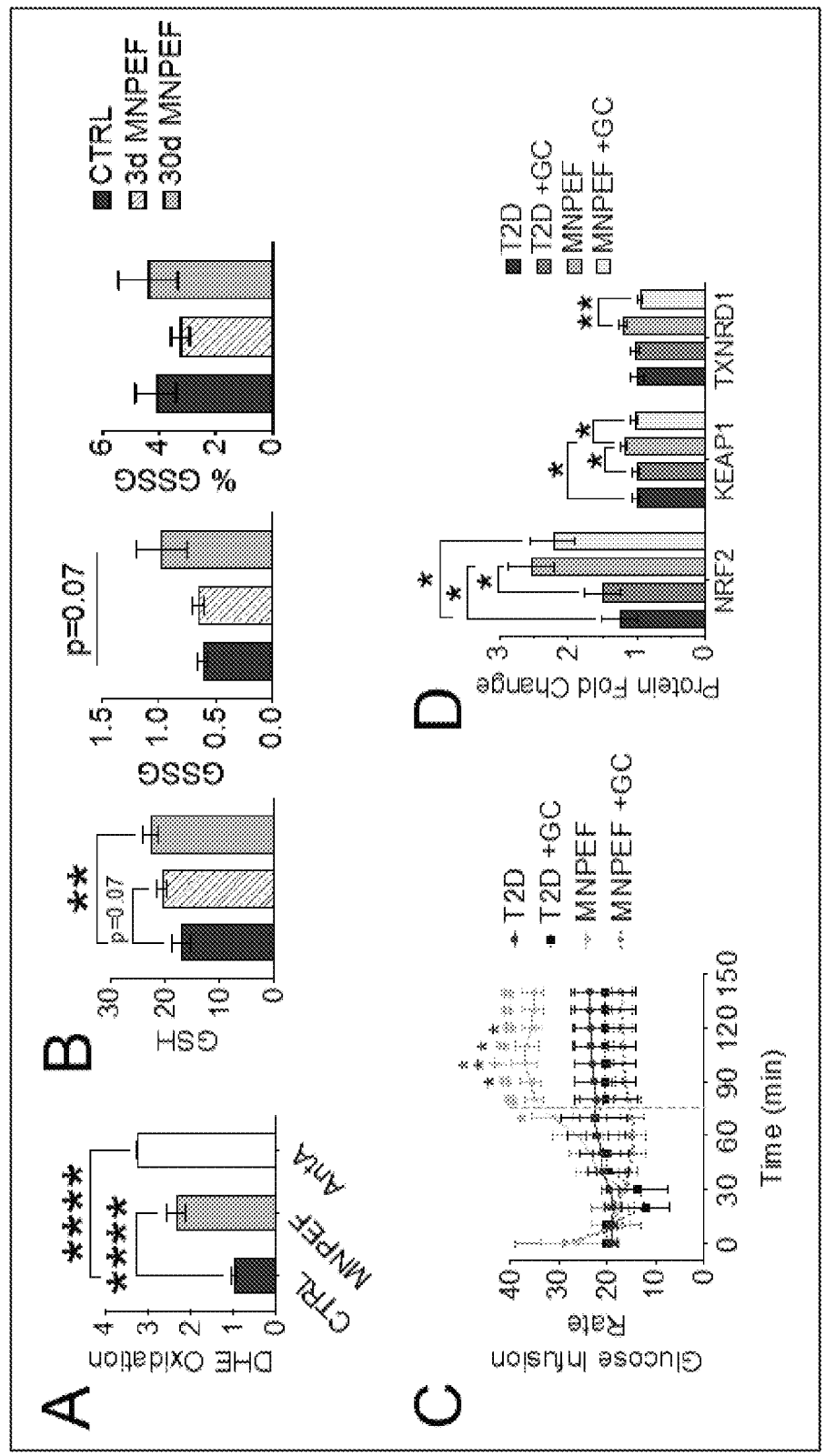
FIG. 26 illustrates experimental data suggesting that MNPEFs elicit anti-diabetic effects through the regulation of reactive oxygen species (ROS) and antioxidant systems.

FIG. 26 illustrates experimental data suggesting that MNPEFs elicit anti-diabetic effects through the regulation of reactive oxygen species (ROS) and antioxidant systems. There is a growing body of literature showing that a small amount of stress via ROS can elicit beneficial changes in the body. We have identified that MNPEFs regulate ROS to improve diabetes. Data in Section A suggests that DHE oxidation (a marker of ROS) is increased in the livers of T2D mice that have improved diabetes after MNPEF treatment. Data in Section B suggests MNPEFs increase glutathione, an antioxidant, after 3 days of treatment and is maximized at 30 days of treatment in the liver of T2D mice. Data in Section C suggests that the improvement in insulin sensitivity elicited by MNPEF treatment is attenuated when ROS is blocked with GC (a compound known to break down ROS). Data in Section D suggests proteins (NRF2, KEAP1) that activate the production of antioxidants (TXNRD1) are elevated after treatment with MNPEF and are blocked from increasing when ROS is blocked with GC.

Figure 27:
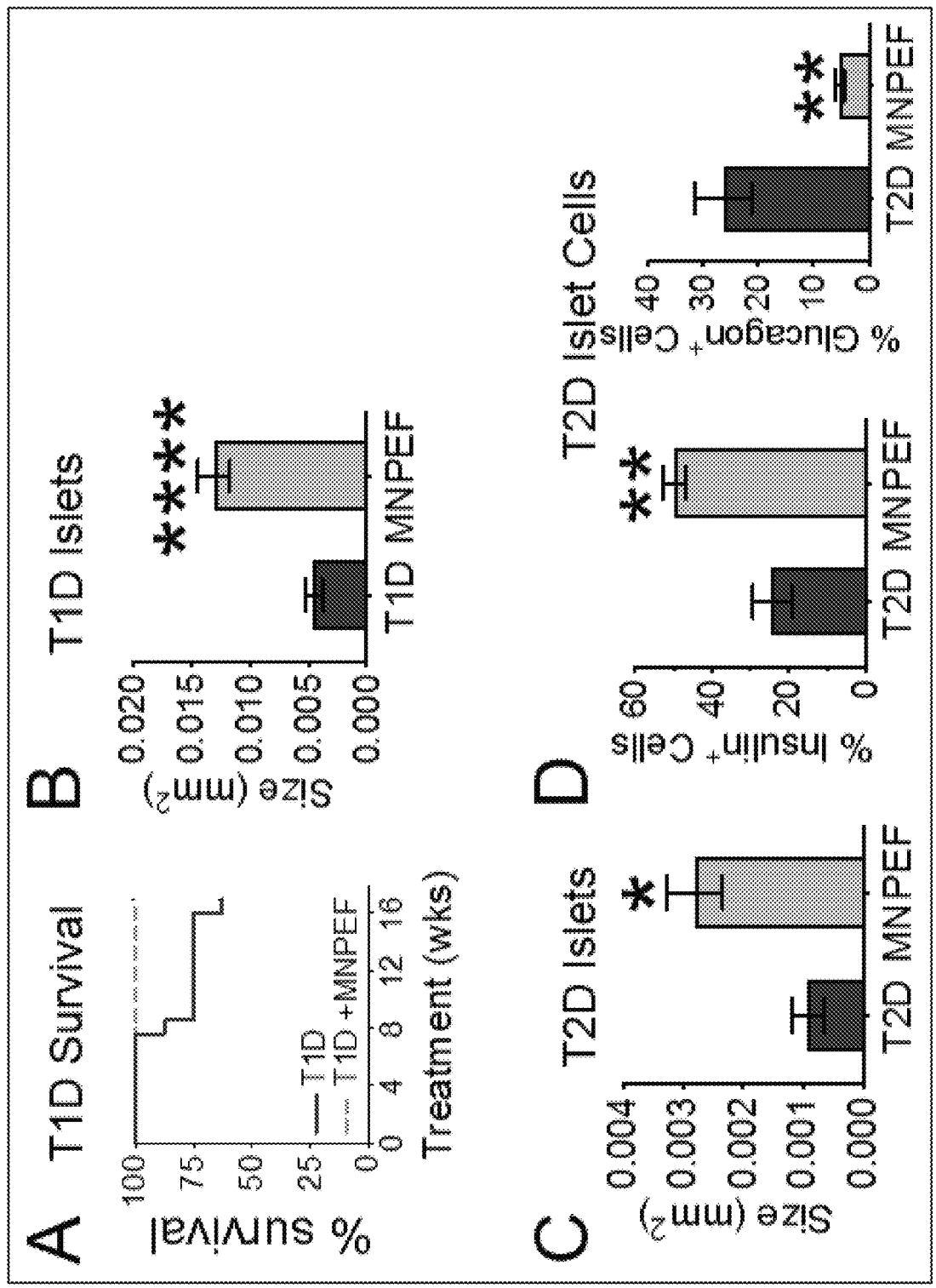
FIG. 27 illustrates experimental data suggesting that MNPEFs increase T1D survival and restores pancreatic islets.

FIG. 27 illustrates experimental data suggesting that MNPEFs increase T1D survival and restores pancreatic islets. Data in Section A suggest that T1D animals treated with MNPEF survive longer compared to their untreated T1D counterparts. Data in Section B suggests that the size of T1D animal pancreatic islets is increased after MNPEF treatment. Data in Section C suggests that Size of T2D animal pancreatic islets is increased after MNPEF treatment. Data in Section D suggests that the percentage of T2D islets expressing insulin (left) is increased and glucagon (right) is decreased after treatment with MNPEF, suggesting a more normal and healthy pancreatic islet.

Figure 28:
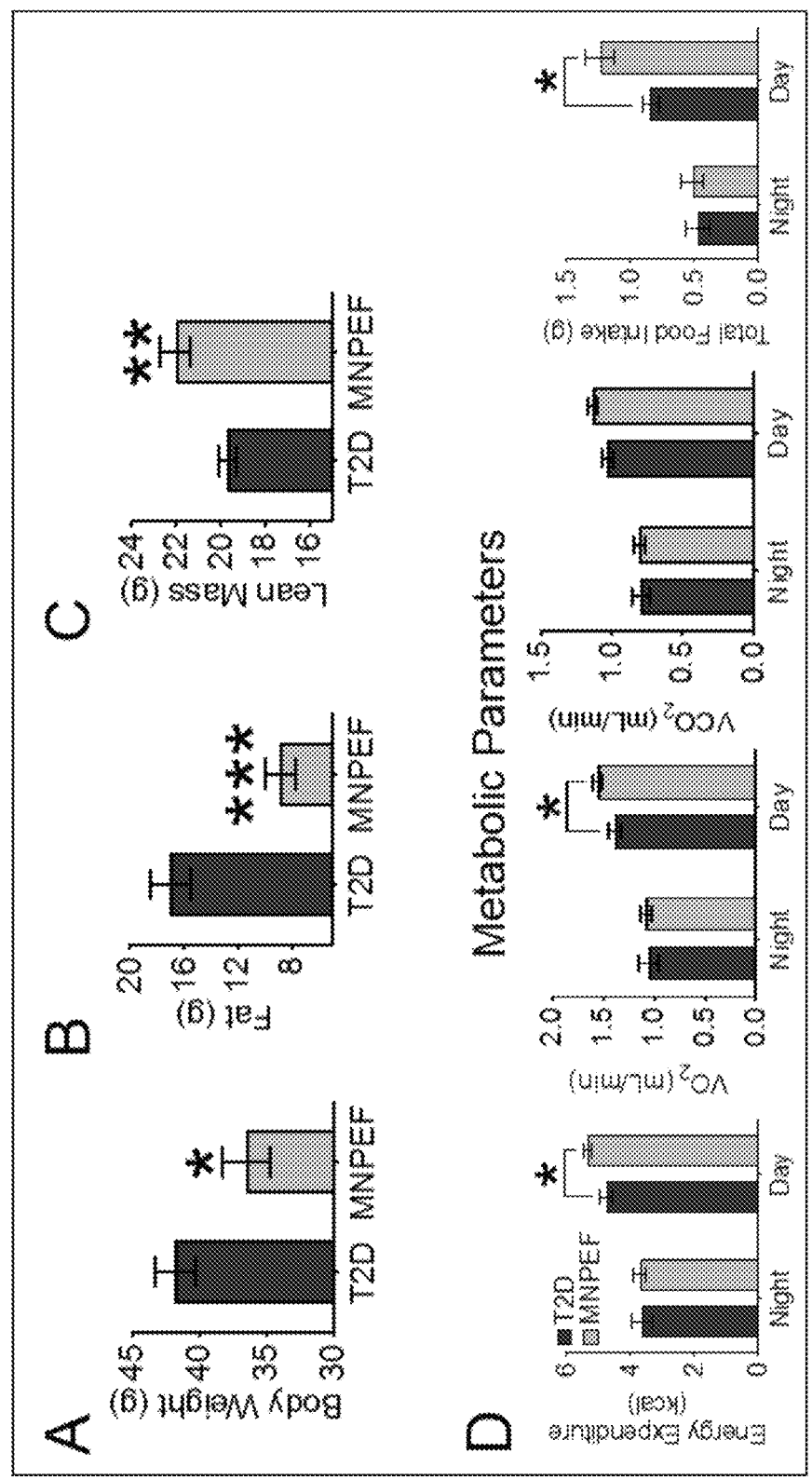
FIG. 28 illustrates experimental data suggesting that MNPEF therapy reduces obesity in T2D mice.

FIG. 28 illustrates experimental data suggesting that MNPEF therapy reduces obesity in T2D mice. Nuclear Magnetic Resonance (NMR) was used to assess body composition of T2D mice treated with MNPEF. Data in Section A suggests that MNPEF treatment reduces total body weight. Data in Section B suggests that MNPEF treatment reduces fat content. Data in Section C suggests that MNPEF treatment increases muscle mass in T2D mice. Metabolic parameters were also assessed in T2D mice treated with and without MNPEF. Data in Section D suggests that, after MNPEF treatment, T2D mice ate more and expended slightly more energy during their awake hours (day), while losing weight and increasing lean mass.

Free radicals are crucial for maintaining health and are potential therapeutic targets in disease states. Since MNPEFs alter the balance of free radicals to treat diabetes and free radicals are at the crux of cancer development and treatment, we treated two common human lung cancers in a gold standard xenograft mouse model with MNPEF therapy. The same parameters of MNPEF therapy that were used for the diabetes Example were used for this example.

Cell lines tested included H292, a human lung carcinoma (slow growing), and H1299, a human lung non-small cell carcinoma (fast growing). For the xenograft studies, all mice with tumors >15 mm in diameter in any one direction for 2 consecutive measurements were euthanized. Therefore, mouse death is determined when tumors reach this criteria.

Figure 29:
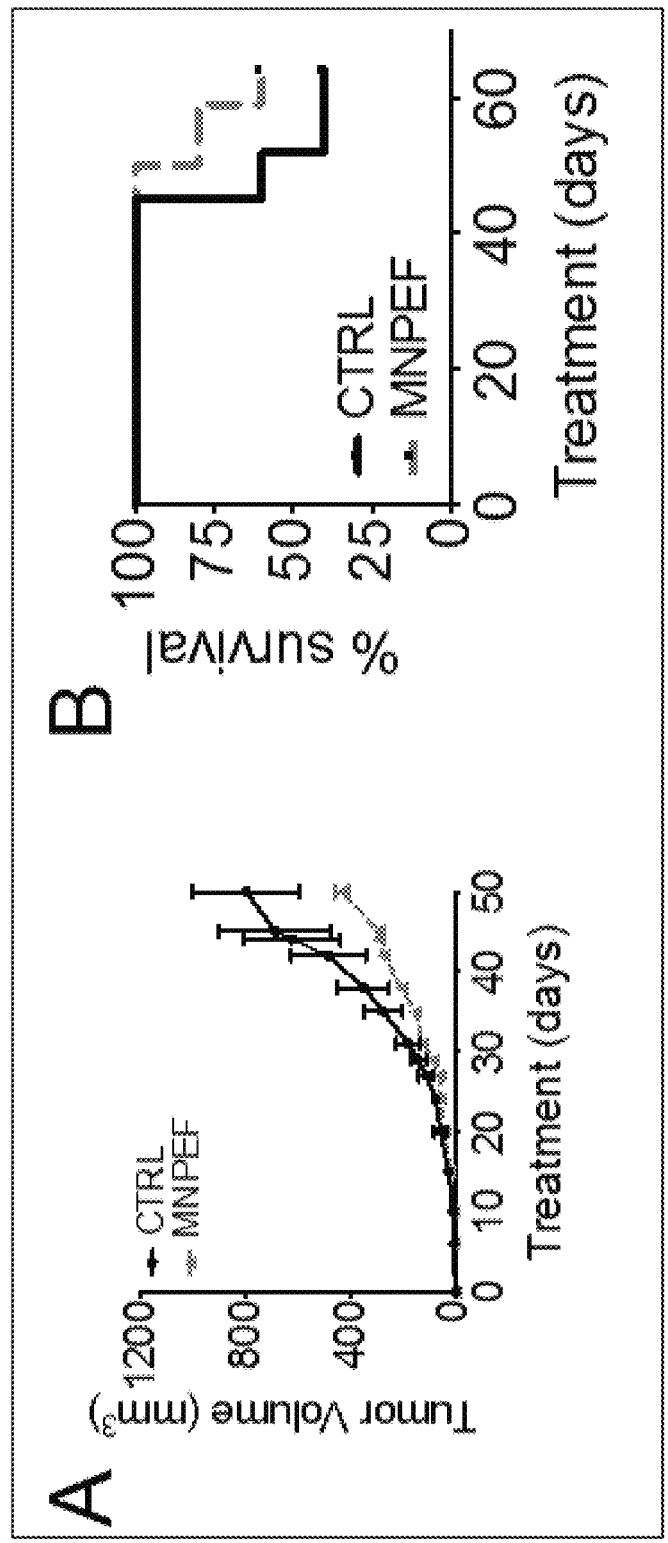
FIG. 29 illustrates experimental data suggesting that MNPEF therapy improves outcomes for mice grafted with a slow growing H292 human lung cancer.

FIG. 29 illustrates experimental data suggesting that MNPEF therapy improves outcomes for mice grafted with a slow growing H292 human lung cancer. Mice were grafted with H292 lung cancer and split into a control group (no standard of care and no MNPEF therapy) and an MNPEF group (magnetic field and orthogonal electric field therapy). Tumor volume was monitored for 50 days. Data in Section A suggests that mice grafted with H292 lung cancer treated with MNPEF had tumors that were 50% smaller than untreated tumors. Data in Section B suggests that MNPEF treatment improved survival of mice grafted with H292 lung cancer by 20%.

Figure 30:
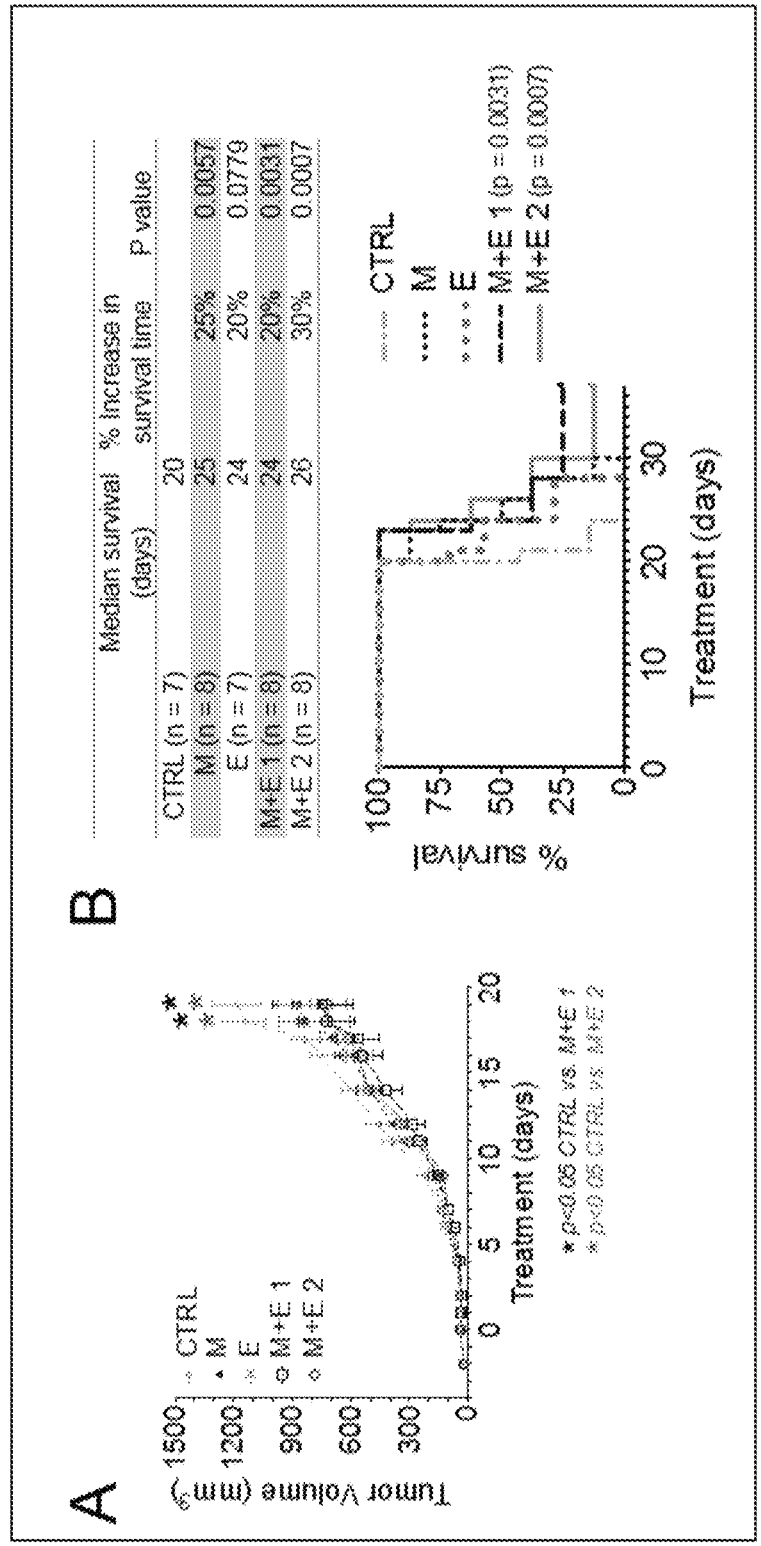
FIG. 30 illustrates experimental data suggesting that MNPEF therapy improves outcomes for mice grafted with a fast growing, H1299 human lung cancer.

FIG. 30 illustrates experimental data suggesting that MNPEF therapy improves outcomes for mice grafted with a fast growing, H1299 human lung cancer. Mice grafted with H1299 lung cancer were split into 5 groups: CTRL (no treatment), M (3 mT magnetic field only), E (3 kV electric field only), M+E 1 (3 mT magnetic field, 3 kV orthogonal electric field), M+E 2 (6 mT magnetic field, 6 kV orthogonal electric field). Data in Section A suggests that the combined magnetic and orthogonal electric fields (M+E 1 and M+E 2) reduced tumor size, and that M field alone or E field alone does not significantly reduce tumor size. Data in Section B suggests that treatments M+E 1 and M+E 2 improves median survival by 4 days and 6 days respectively. The table lists each group, their median survival in days, the improvement in survival time compared to CTRL (no treatment), and the corresponding p-value. M and E fields alone both show a modest improvement in median survival. The combination of both magnetic and electric fields show an even better survival rate with some mice in each M+E 1 and M+E 2 groups surviving over 37 days.

Figure 31:
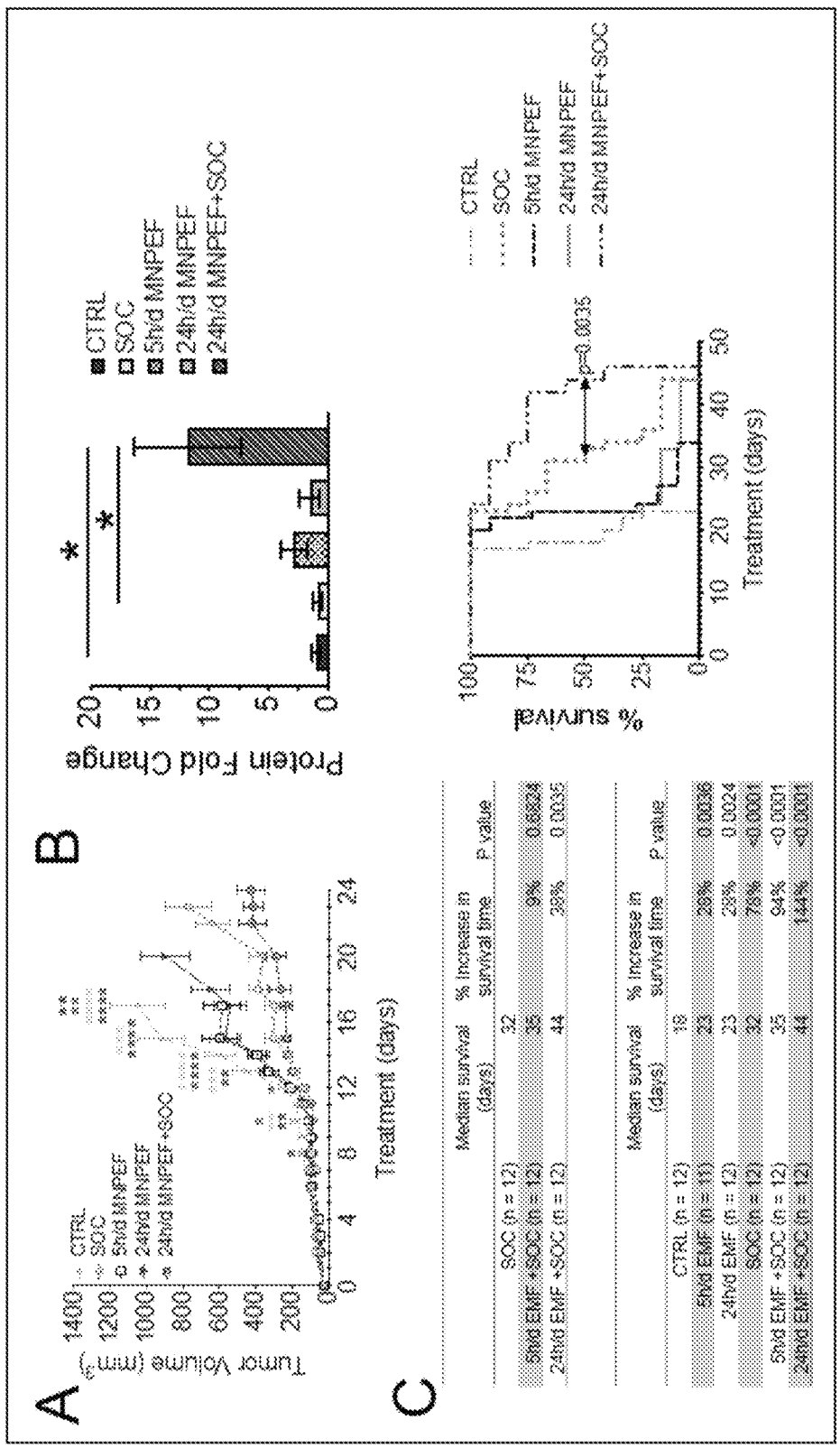
FIG. 31 illustrates experimental data suggesting that MNPEF therapy combined with standard of care is more effective than standard of care alone in treating a fast growing, H1299 human lung cancer.

FIG. 31 illustrates experimental data suggesting that MNPEF therapy combined with standard of care is more effective than standard of care alone in treating a fast growing, H1299 human lung cancer. Mice grafted with H1299 lung cancer were split into 5 groups: CTRL (untreated), 5 h/d (MNPEF therapy only for 5 hours per day), 24 h/d (MNPEF therapy only for 24 hours per day), SOC (standard of care—3 doses of radiation & chemotherapy, cisplatin), and 24 h/d+SOC (24 h/d MNPEF therapy in combination with SOC). Data in Section A suggests that MNPEF therapy alone is effective in reducing tumor size, and MNPEF therapy in combination with SOC is more effective at reducing tumor volume than SOC alone. Cancer cells divide more rapidly, making them more sensitive to DNA damage, and have more disrupted antioxidant systems compared to normal cells. Standard of care (chemotherapy and radiation) takes advantage of this by inducing DNA damage and altering antioxidant systems to kill cancer. To assess whether MNPEFs affect DNA damage, we collected H1299 tumor xenografts and measured protein expression of p-H2A.X, which is a gold standard marker for DNA damage in tumors. This marker was increased 12-fold in the 24 h/d+SOC group compared to SOC. Data in Section B suggests that MNPEFs synergize with SOC to induce and maintain DNA damage to kill cancer cells. Data in Section C suggests that mice treated with a combination of MNPEFs and SOC show a 38% improvement in survival compared to SOC alone. Median survival for mice treated with SOC alone is 32 days. Median survival for mice treated with MNPEFs and SOC is 44 days. Table 1 lists each group, their median survival in days, the improvement in survival time compared to SOC, and corresponding p-values. Table 2 lists the same information with improvement of survival compared to CTRL (no treatment).

The experiments suggest that MNPEFs may improve health by inducing hormesis. Free radicals, including reactive oxygen species (ROS) and reactive nitrogen species (RNS) have been implicated in the pathogenesis of a wide range of chronic diseases. The majority of free radicals are produced in the mitochondria as a result of cellular respiration. Free radicals are also generated in other cellular compartments by various enzymes. Free radicals were once thought to be destructive to the cell, however, there is a growing body of evidence demonstrating that free radicals can induce beneficial changes to cells that improve the health of the organism.

It is well observed that mild environmental stress often causes adaptive responses that lead to beneficial effects on the organism. While higher doses of an environmental stimulus may lead to toxic effects, small doses can promote health. The biphasic of environmental stress is termed "hormesis" and describes the beneficial effects of many stressors, including exercise. Exercise induces the production of ROS and RNS which can be toxic when produced in high quantities. Indeed, the immune system generates free radicals to kill pathogens. However, exercise is beneficial because it induces the generation of low levels of ROS/RNS causing adaptive changes in the cell that make it better prepared to deal with future stress (Radak, Z., Chung, H. Y. & Goto, S. Exercise and hormesis: oxidative stress-related adaptation for successful aging. *Biogerontology* 6, 71-75 (2005)). There is a growing body of evidence showing that the activation of hormesis can be therapeutic in a wide range of diseases or adverse conditions, including diabetes mellitus, obesity, cancer, neurodegenerative disease, inflammation and aging[2-7]. (Radak, Z., Chung, H. Y. & Goto, S. Exercise and hormesis: oxidative stress-related adaptation for successful aging. *Biogerontology* 6, 71-75 (2005); De Haes, W., et al. Metformin promotes lifespan through mitohormesis via the peroxiredoxin PRDX-2. *Proceedings of the National Academy of Sciences* 111, E2501 (2014); Cox, C. S., et al. Mitohormesis in Mice via Sustained Basal Activation of Mitochondrial and Antioxidant Signaling. *Cell metabolism* 28, 776-786.e775 (2018); Dugan, L. L., et al. AMPK dysregulation promotes diabetes-related reduction of superoxide and mitochondrial function. *The Journal of Clinical Investigation* 123, 4888-4899 (2013); Lark, D. S., et al. Enhanced Mitochondrial Superoxide Scavenging Does Not Improve Muscle Insulin Action in the High Fat-Fed Mouse. *PLOS ONE* 10, e0126732 (2015); Luna-López, A., González-Puertos, V. Y., López-Diazguerrero, N. E. & Königsberg, M. New considerations on hormetic response against oxidative stress. *Journal of cell communication and signaling* 8, 323-331 (2014); Pearce, O. M., Läubli, H., Bui, J. & Varki, A. Hormesis in cancer immunology: Does the quantity of an immune reactant matter? *Oncoimmunology* 3, e29312-e29312 (2014).)

Our data suggest that MNPEFs induce ROS formation, particularly superoxide, a highly reactive oxygen species. MNPEF driven induction of ROS leads to hormetic changes that improves the health of the animal. These hormetic changes include enhanced activity of the ROS scavenging enzyme glutathione (GSH), reduced activity and expression of mitochondrial complex I one of the major ROS producers in the cell, activation of the metabolism regulating enzyme, AMPK, and increased expression of the cytoprotective stimulating proteins, nuclear factor erythroid-derived 2-like 2 (Nrf2) and Keap-1. Treating animals with a superoxide specific scavenger throughout MNPEF therapy attenuated the beneficial effects of MNPEFs. These findings suggest that that MNPEFs generate ROS and induce hormesis to elicit beneficial effects on metabolism.

Additional Notes & Examples:

Example 1 includes subject matter (such as a system, a device, apparatus or machine) may deliver a therapy by delivering energy to tissue. The system may comprise a magnetic field system and an electric field system. The magnetic field system may be configured to provide a magnetic field in a first direction to the tissue. The magnetic field system may include at least one magnetic field source to produce the magnetic field. The magnetic field produced by the at least one magnetic field source may include a magnetic field produced by at least one of a permanent magnet, a temporary magnet or electric current flow through a conductor. The electric field system may be configured to provide an electric field in a second direction to the tissue. The electric field system may include at least one electric field source to provide the electric field and the second direction is non-parallel to the first direction.

In Example 2, the subject matter of Example 1 may optionally be configured such that the first and second directions are separated by angle within a range of 10 degrees to 170 degrees.

In Example 2, the subject matter of Example 1 may optionally be configured such that the first and second directions are separated by angle within a range of 10 degrees to 90 degrees.

In Example 3, the subject matter of Example 1 may optionally be configured such that the first and second directions are separated by angle within a range of 30 degrees to 150 degrees.

In Example 4, the subject matter of Example 1 may optionally be configured such that the first and second directions are separated by angle within a range of 30 degrees to 90 degrees.

In Example 5, the subject matter of Example 1 may optionally be configured such that the first and second directions are separated by angle within a range of 45 degrees to 135 degrees.

In Example 6, the subject matter of Example 1 may optionally be configured such that the first and second directions are separated by angle within a range of 45 degrees to 90 degrees.

In Example 7, the subject matter of Example 1 may optionally be configured such that the first and second directions are separated by angle within a range of 60 degrees to 120 degrees.

In Example 8, the subject matter of Example 1 may optionally be configured such that the first and second directions are separated by angle within a range of 60 degrees to 90 degrees.

In Example 9, the subject matter of Example 1 may optionally be configured such that the first and second directions are separated by angle within a range of 80 to 100 degrees.

In Example 10, the subject matter of Example 1 may optionally be configured such that the first and second directions are separated by angle within a range of 1 degree to 30 or an angle within a range of 150 degrees to 179 degrees.

In Example 11, the subject matter of any one or any combination of Examples 1-10 may optionally be configured such that the least one magnetic field source includes one permanent or temporary magnet to produce the magnetic field.

In Example 12, the subject matter of any one or any combination of Examples 1-10 may optionally be configured such that the at least one magnetic field source includes at least two permanent or temporary magnets on opposing sides of the tissue to produce the magnetic field in the first direction to the tissue.

In Example 13, the subject matter of any one or any combination of Examples 1-12 may optionally be configured such that the at least one magnetic field source includes the conductor which is configured to generate the magnetic field in the first direction to the tissue when current flows through the conductor.

In Example 14, the subject matter of Example 13 may optionally be configured such that the conductor includes a coil shape.

In Example 15, the subject matter of any one or any combination of Examples 13-14 may optionally be configured such that the current includes a direct current.

In Example 16, the subject matter of any one or any combination of Examples 13-15 may optionally be configured such that the current includes an alternating current. This may include, for example, an AC on one conductor and a DC on another.

In Example 17, the subject matter of Example 16 may optionally be configured such that the alternating current has a frequency less than 1 kHz.

In Example 18, the subject matter of Example 16 may optionally be configured such that the alternating current has a frequency less than 100 Hz.

In Example 19, the subject matter of any one or any combination of Examples 1-18 may optionally be configured such that the at least one electric field source includes an energy source electrically connected to at least one electrode, wherein the energy source includes one or more of at least one a voltage source or at least one a current source.

In Example 20, the subject matter of Example 19 may optionally be configured such that the at least one electrode is one electrode.

In Example 21, the subject matter of Example 19 may optionally be configured such that the at least one electrode includes at least two electrodes on opposing sides of the tissue to produce the electric field in the second direction to the tissue.

In Example 22, the subject matter of any one of Examples 20-21 may optionally be configured such that the at least one electrode includes at least one a plate-shaped electrode.

In Example 23, the subject matter of any one or any combination of Examples 19-22 may optionally be configured such that one or more of the at least one electric field source is configured to provide a direct current to the at least electrode.

In Example 24, the subject matter of any one or any combination of Examples 19-23 may optionally be configured such that one or more of the at least one electric field source is configured to provide an alternating current to the at least electrode.

In Example 25, the subject matter of any one or any combination of Examples 1-24 may optionally be configured such that at least one of the magnetic field system or the electric field system is an implantable system.

In Example 26, the subject matter of Example 25 may optionally be configured such that both of the magnetic field system and the electric field system include implantable systems (e.g. both are implantable).

In Example 27, the subject matter of any one or any combination of Examples 1-24 may optionally be configured such that at least one of the magnetic field system or the electric field system includes or is an external, wearable system.

In Example 28, the subject matter of Example 27 may optionally be configured such that the external, wearable system includes a vest, and the vest includes both the electric field system and the magnetic field system.

In Example 29, the subject matter of any one or any combination of Examples 27-28 may optionally be configured such that the external, wearable system includes an article configured to worn on a head, and the article includes both the electric field system and the magnetic field system.

In Example 30, the subject matter of any one or any combination of Examples 27-29 may optionally be configured such that the external, wearable system includes at least one patch configured to be attached to skin or a wrap configured to be wrapped around a body part.

In Example 31, the subject matter of any one or any combination of Examples 1-30 may optionally be configured such that may optionally be configured such that the at least one of the magnetic field system or the electric field system is an external, environmental system.

In Example 32, the subject matter of Example 31 may optionally be configured such that the external, environmental system includes a system configured to provide the magnetic field and the electric field to the patient when the patient is in bed.

In Example 33, the subject matter of Example 31 may optionally be configured such that the external, environmental system includes a system configured to provide the magnetic field and the electric field to the patient when the patient is in a chair or other furniture, or in a motor vehicle, or at a work station.

In Example 34, the subject matter of any one or any combination of Examples 1-33 may optionally be configured such that both of the magnetic field system and the electric field system include external wearable systems, or are external, environmental systems.

In Example 35, the subject matter of any one or any combination of Examples 1-34 may optionally be configured to include a controller configured to control timing of at least of the magnetic field or the electric field.

In Example 36, the subject matter of Example 35 may optionally be configured such that the timing is defined by programmed instructions.

In Example 37, the subject matter of any one or any combination of Examples 35-36 may optionally be configured to further include a user interface configured to control at least one of an initiation or a termination for the at least one of the magnetic field or the electric field.

In Example 38, the subject matter of any one or any combination of Examples 35-37 may optionally be configured such that the controller is configured to control a daily duration of a dose for delivering the therapy.

In Example 39, the subject matter of Example 38 may optionally be configured such that the dose is between one second and 24 hours.

In Example 40, the subject matter of Example 39 may optionally be configured such that the duration of the dose is between two hours and 12 hours.

In Example 41, the subject matter of Example 39 may optionally be configured such that the duration of the dose is between 4 hours and 10 hours.

In Example 42, the subject matter of Example 39 may optionally be configured such that the duration of the dose is between 1 second minutes and 4 hours.

In Example 43, the subject matter of Example 39 may optionally be configured such that the duration of the dose is over one second.

In Example 44, the subject matter of any one or any combination of Examples 1-43 may optionally be configured such that the magnetic field system is configured to provide the magnetic field in the first direction with a magnetic field strength less than 100 mT.

In Example 45, the subject matter of any one or any combination of Examples 1-43 may optionally be configured such that the magnetic field system is configured to provide the magnetic field in the first direction with a magnetic field strength within a range of 1 to 10 mT.

In Example 46, the subject matter of any one or any combination of Examples 1-45 may optionally be configured such that the electric field system is an external system configured to provide the electric field in the second direction with an electric field strength less than 1000 kV/m.

In Example 47, the subject matter of any one or any combination of Examples 1-45 may optionally be configured such that the electric field system is an external system configured to provide the electric field in the second direction with an electric field strength within a range of 0.1 to 500 kV/m.

In Example 48, the subject matter of any one or any combination of Examples 1-47 may optionally be configured such that the therapy includes a therapy to treat diabetes, and the electric field system is configured to provide the electric field in the second direction with an electric field strength within a range of 2 kV/m to 30 kV/m.

In Example 49, the subject matter of any one or any combination of Examples 1-48 may optionally be configured such that the therapy includes a therapy to treat cancer, and the electric field system is configured to provide the electric field in the second direction with an electric field strength within a range of 2 kV/m to 60 kV/m.

In Example 49, the subject matter of Example 1 may optionally be configured such that the electric field system is configured to be attached to skin or implanted, and is configured to provide the electric field in the second direction with an electric field strength less than 5 kV/m and/or a current less than 5 mA.

In Example 50, the subject matter of Example 49 may optionally be configured such that the electric field system is configured to provide the electric field in the second direction with an electric field strength less than 500 V/m and/or an electric current less than 100 µA.

In Example 51, the subject matter of any one or any combination of Examples 1-50 may optionally be configured such that the electric field system is configured to provide the electric field or the magnetic field system is configured to provide the magnetic field with a frequency less than 1,000 kHz.

In Example 52, the subject matter of any one or any combination of Examples 1-50 may optionally be configured such that the electric field system is configured to provide the electric field or the magnetic field system is configured to provide the magnetic field with a frequency within a range between 100 Hz and 10 kHz.

An example (e.g. Example 53) of subject matter (e.g. a method, a means for performing acts, or a machine-readable medium including instructions that, when performed by the machine, cause the machine to perform acts) may include delivering a therapy by delivering energy to tissue. Delivering energy to the tissue may include providing a magnetic field in a first direction to the tissue using a magnetic field system including a magnetic field source to produce the magnetic field. The magnetic field produced by the magnetic field source may include a magnetic field produced by at least one of a permanent magnet, a temporary magnet or electric current flow through a conductor. Delivering energy to the tissue may further include providing an electric field in a second direction to the tissue using an electric field system including an electric field source to produce the electric field, wherein the second direction is non-parallel to the first direction.

In Example 54, the subject matter of Example 53 may optionally be configured such that the therapy includes a therapy to treat diabetes, and the delivering the therapy includes delivering energy to liver or pancreatic tissue.

In Example 55, the subject matter of any one or any combination of Examples 53-54 may optionally be configured such that the therapy includes a therapy to treat cancer, and the delivering the therapy includes delivering energy to a tumor.

In Example 56, the subject matter of Example 55 may optionally be configured such that the therapy to treat cancer induces DNA damage with an increase in pH2A.X protein, and is provided after standard of care is given.

In Example 57, the subject matter of any one or any combination of Examples 55-57 may optionally be configured such that the therapy includes a therapy to treat cancer, and the delivering the therapy includes delivering energy to visceral muscle, white fat, brown fat, gall bladder, stomach, large and small intestines, kidney, heart, spleen, appendix, retina and optic nerve or brain.

In Example 58, the subject matter of any one or any combination of Examples 53-57 may optionally be configured such that the therapy includes delivering the therapy to treat a chronic disease.

In Example 59, the subject matter of Example 55 may optionally be configured such that the therapy to treat a chronic disease includes delivering the energy to increase free radical species in the tissue.

In Example 60, the subject matter of Example 53 may optionally be configured such that the therapy includes a therapy for diabetes, cancer, obesity, inflammation, or glaucoma.

An example (Example 61) of subject matter (e.g. a method, a means for performing acts, or a machine-readable medium including instructions that, when performed by the machine, cause the machine to perform acts) may prevent, inhibit or treat one or more symptoms of a disease associated with aberrant reactive oxygen species levels in a mammal. The subject matter may include applying to one or more organs or tissues of the mammal, a magnetic field in a first direction and an electric field in a second direction. The magnetic field may be provided by at least one magnetic field source that includes at least one permanent magnet, a temporary magnet or electric current flow through a conductor to produce the magnetic field. The electric field may be provided by at least one electric field source to provide the electric field and the second direction is non-parallel to the first direction. The electric and magnetic fields are effective to prevent, inhibit or treat the one or more symptoms of the disease in the mammal associated with aberrant reactive oxygen species levels.

In Example 62, the subject matter of Example 61 may optionally be configured such that the magnetic field and the electric field are exogenously applied.

In Example 63, the subject matter of Example 61 may optionally be configured such that an implanted device applies the magnetic field and the electric field are exogenously applied.

In Example 64, the subject matter of any one or any combination of Examples 61-63 may optionally be configured such that the mammal is a human.

In Example 65, the subject matter the subject matter of any one or any combination of Examples 61-64 may optionally be configured such that the disease includes cancer (e.g. liver cancer, pancreatic cancer, bladder cancer, stomach cancer, colon cancer, breast cancer, prostate cancer, lung cancer, brain cancer, melanoma, lymphoma, sarcoma or leukemia).

In Example 66, the subject matter of any one or any combination of Examples 61-64 may optionally be configured such that the disease includes diabetes (e.g. Type 1 or Type 2).

In Example 67, the subject matter the subject matter of any one or any combination of Examples 62-64 may optionally be configured such that the disease includes obesity.

In Example 68, the subject matter the subject matter of any one or any combination of Examples 61-67 may optionally be configured such that the first and second directions are separated by angle within a range of 10 degrees to 170 degrees.

In Example 69, the subject matter the subject matter of any one or any combination of Examples 61-67 may optionally be configured such that the first and second directions are separated by angle within a range of 60 degrees to 120 degrees.

In Example 70, the subject matter the subject matter of any one or any combination of Examples 61-69 may optionally be configured such that the magnetic field and the electric field are applied concurrently.

In Example 71, the subject matter the subject matter of any one or any combination of Examples 61-69 may optionally be configured such that the magnetic field and the electric field are applied sequentially.

In Example 72, the subject matter the subject matter of any one or any combination of Examples 61-71 may optionally be configured such that the magnetic field and the electric field are applied using a wearable device.

In Example 73, the subject matter the subject matter of any one or any combination of Examples 61-72 may optionally be configured such that the magnetic field has a strength that is less than 100 mT.

In Example 74, the subject matter the subject matter of any one or any combination of Examples 61-72 may optionally be configured such that the magnetic field has a strength that is within a range of 1 to 10 mT.

In Example 75, the subject matter the subject matter of any one or any combination of Examples 61-72 may optionally be configured such that the electric field has a strength that is less than 1000 V/m.

In Example 76, the subject matter the subject matter of any one or any combination of Examples 61-72 may optionally be configured such that the electric field has a strength within a range of 0.1 to 100 kV/m.

In Example 77, the subject matter the subject matter of any one or any combination of Examples 61-72 may optionally be configured such that the electric field has a strength that is less than 5 kV/m or 5 mA.

In Example 78, the subject matter the subject matter of any one or any combination of Examples 61-72 may optionally be configured such that the electric field has a strength that is less than 500 V/m or 100 µA.

In Example 79, the subject matter the subject matter of any one or any combination of Examples 61-72 may optionally be configured such that the magnetic field has a frequency less than 1,000 kHz.

In Example 80, the subject matter the subject matter of any one or any combination of Examples 61-72 may optionally be configured such that the magnetic field has a frequency within a range between 100 Hz and 10 kHz.

An example (e.g. Example 81) of subject matter (e.g. a method, a means for performing acts, or a machine-readable medium including instructions that, when performed by the machine, cause the machine to perform acts) may include delivering a therapy by delivering energy to tissue. Delivering energy to the tissue may include providing a magnetic field in a first direction to the tissue. The therapy may be cancer. Our cancer data shows that a magnetic field alone (3 mT) is capable of reducing tumor size and improving overall survival.

The above detailed description is intended to be illustrative, and not restrictive. The scope of the disclosure should, therefore, be determined with references to the appended claims, along with the full scope of equivalents to which such claims are entitled.

What is claimed is:

1. A system for delivering a therapy to a patient on a surface of a bed, comprising:
    a magnetic system configured to provide a magnetic field in a first direction over the surface of the bed; and an electric field system configured to provide an electric field in a second direction over the surface of the bed, the second direction being non-parallel to the first direction,
wherein the electric field system includes at least a first electrode and at least a second electrode configured to be positioned on opposing first and second sides of the bed, both the first electrode and the second electrode are plate-shaped electrodes configured to be positioned substantially parallel to each other to provide the electric field with uniformity between the plate-shaped electrodes and over the surface of the bed, and with approximately linear electric field vectors in the second direction from the first side of the bed to the second side of the bed.

2. The system of claim 1, wherein the first direction is substantially orthogonal to the second direction.

3. The system of claim 2, wherein the electric field system is configured for the first electrode to be positioned over the surface of the bed and the second electrode to be positioned beneath the surface of the bed.

4. The system of claim 2, wherein the electric field system is configured for the first electrode to be positioned adjacent a head end of the bed and the second electrode to be adjacent a foot end of the bed opposite the head end of the bed.

5. The system of claim 2, wherein the magnetic system is configured to provide the magnetic field between a head end of the bed and a foot end of the bed opposite the head end of the bed.

6. The system of claim 2, wherein the magnetic system is configured to provide the magnetic field between opposing left and right sides of the bed.

7. The system of claim 1, wherein the magnetic system includes at least a first magnetic source and at least a second magnetic source configured to be positioned on opposing sides of the bed to provide approximately linear magnetic field vectors in the first direction over the surface of the bed.

8. The system of claim 1, wherein the magnetic field is produced by at least one of a permanent magnet, a temporary magnet, or electric current flow through a conductor.

9. The system of claim 1, wherein the magnetic system includes at least one coil configured to provide the magnetic field in the first direction.

10. The system of claim 1, further comprising a controller configured to control delivery of the therapy, and a user interface operably connected to the controller and configured for use by a user to send commands to the controller.

11. The system of claim 10, wherein the user interface includes at least one control configured for use by the user to:
  start or stop delivery of at least a portion of the therapy;
  adjust at least one parameter for generating the electric field for the therapy;
  adjust at least one parameter for generating the magnetic field for the therapy; or
  create a schedule for use by the controller to control timing for delivering at least one of the magnetic field or the electric field.

12. The system of claim 10, wherein the controller is configured to be programmed with one or more therapy programs, wherein each of the one or more therapy programs has a corresponding set of parameters used to generate at least one of the magnetic field or the electric field.

13. The system of claim 1, wherein the system is configured to collect data indicative of delivered therapy.

14. The system of claim 1, further comprising at least one sensor configured to sense at least one biomarker, the at least one biomarker being indicative of a state of a disease, a condition of a patient, a symptom of the disease or the condition, or a surrogate of a parameter indicative of the symptom.

15. The system of claim 1, further comprising at least one of a position sensor, a motion sensor, a clock/timer, a sensor configured for detecting an electric field, or a sensor for detecting a magnetic field for use to monitor the delivering of the therapy.

16. The system of claim 15, further comprising at least one of:
  a load sensor configured to detect pressure on the bed;
  a temperature sensor;
  an accelerometer;
  an impedance sensor;
  a sound sensor;
  a heart rate sensor;
  a respiration sensor; or
  an activity sensor.

17. The system of claim 1, wherein the electric field system is configured to provide the electric field with a frequency less than 10 kHz.

18. The system of claim 1, wherein the magnetic system is configured to immerse the patient on the surface in the magnetic field and the electric field system is configured to immerse the patient on the surface in the electric field.

19. A method for delivering a therapy to a patient on a surface of a bed, comprising:
  providing a magnetic field in a first direction over the surface of the bed; and
  providing an electric field in a second direction over the surface of the bed, wherein the electric field is provided using substantially parallel, plate-shaped electrodes positioned on opposing first and second sides of the bed to provide the electric field with uniformity between the plate-shaped electrodes and over the surface of the bed, and with approximately-linear electric field vectors from the first side of the bed to the second side of the bed, wherein the first direction is substantially orthogonal to the second direction.

20. The method of claim 19, further comprising:
  using a controller to control delivery of the therapy;
  using a user interface to send commands to the controller, including at least one of:
  start or stop delivery of at least a portion of the therapy;
  adjust at least one parameter for generating the electric field for the therapy;
  adjust at least one parameter for generating the magnetic field for the therapy; or
  create a schedule for use by the controller to control timing for delivering at least one of the magnetic field or the electric field; and
  collecting data indicative of delivered therapy.

21. The method of claim 19, wherein the electric field is provided with a frequency less than 10 kHz.

22. The method of claim 19, wherein the patient on the surface is immersed in the magnetic field and immersed in the electric field.

* * * * *